(12) United States Patent
Weiske et al.

(10) Patent No.: US 11,161,825 B2
(45) Date of Patent: Nov. 2, 2021

(54) 4-OXO-2,3,4,5-TETRAHYDRO-1H-1,5-BENZ-ODIAZEPINE-7-CARBOXAMIDES

(71) Applicants: Bayer Aktiengesellschaft, Leverkusen (DE); Bayer Pharma Aktiengesellschaft, Berlin (DE)

(72) Inventors: Jörg Weiske, Berlin (DE); Carlo Stresemann, Berlin (DE); Stefan Nikolaus Gradl, Berlin (DE); Ulrike Röhn, Berlin (DE); Clara Christ, Berlin (DE); Holger Steuber, Berlin (DE); Manfred Husemann, Hohen Neuendorf (DE); Norbert Schmees, Berlin (DE); Kai Thede, Berlin (DE); Stephan Siegel, Berlin (DE); Antonius Ter Laak, Berlin (DE)

(73) Assignees: Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 16/638,683

(22) PCT Filed: Aug. 9, 2018

(86) PCT No.: PCT/EP2018/071649
§ 371 (c)(1),
(2) Date: Feb. 12, 2020

(87) PCT Pub. No.: WO2019/034532
PCT Pub. Date: Feb. 21, 2019

(65) Prior Publication Data
US 2020/0199083 A1 Jun. 25, 2020

(30) Foreign Application Priority Data

Aug. 15, 2017 (EP) ..................... 17186334
Feb. 2, 2018 (EP) ..................... 18154895
May 30, 2018 (EP) ..................... 18175162

(51) Int. Cl.
| | |
|---|---|
| *C07D 243/12* | (2006.01) |
| *C07D 401/06* | (2006.01) |
| *C07D 403/06* | (2006.01) |
| *C07D 409/06* | (2006.01) |
| *C07D 413/06* | (2006.01) |

(52) U.S. Cl.
CPC ......... *C07D 243/12* (2013.01); *C07D 401/06* (2013.01); *C07D 403/06* (2013.01); *C07D 409/06* (2013.01); *C07D 413/06* (2013.01)

(58) Field of Classification Search
CPC ..... C07D 243/12; C07D 243/24; A61K 31/55
See application file for complete search history.

(56) References Cited

U.S. PATENT DOCUMENTS

| | | | | |
|---|---|---|---|---|
| 6,239,131 B1* | 5/2001 | Shinozaki | ............ | C07D 409/12 514/221 |
| 2005/0054633 A1* | 3/2005 | Flohr | ................... | C07D 313/14 514/212.04 |
| 2016/0221972 A1* | 8/2016 | Zheng | ..................... | A61P 3/00 |

FOREIGN PATENT DOCUMENTS

| | | |
|---|---|---|
| CN | 106831614 A | 6/2017 |
| EP | 0945445 A1 | 9/1999 |

OTHER PUBLICATIONS

Simone, Oncology: Introduction, Cecil Textbook of Medicine, 20th Edition, vol. 1, pp. 1004-1010, 1996.*
Acute Leukemia, Merck Manual (Online Edition) 6 pages, pp. 1-6 (2013).*
Pearce et al., Failure modes in anticancer drug discovery and development, Cancer Drug Design and Discovery Edited by Stephen Neidle, Chapter 18, pp. 424-435 (2008).*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431, 2001.*
Damasio, Alzheimer's Disease and related dementias, Cecil Textbook of Medicine, 20th Edition, vol. 2, pp. 1992-1996, 1996.*
Layzer, Degenerative diseases of the nervous system, Cecil Textbook of Medicine, 20th Edition, vol. 2, pp. 2050-2057, 1996.*
Aiello, L. et al. (1994). "Vascular Endothelial Growth Factor in Ocular Fluid of Patients with Diabetic Retinopathy and Other Retinal Disorders," New Engl. J. Med. 331(22):1480-1487.

(Continued)

*Primary Examiner* — Deepak R Rao
(74) *Attorney, Agent, or Firm* — Morrison & Foerster LLP

(57) ABSTRACT

The present invention covers 4-oxo-2,3,4,5-tetrahydro-1H-1,5-benzodiazepine-7-carboxamide compounds of general formula (I): in which $R^1$, $R^{2a}$, $R^{2b}$, $R^{2c}$, $R^{3a}$, $R^{3b}$, $R^{4a}$, $R^{4b}$, $R^5$ and X are as defined herein, methods of preparing said compounds, intermediate compounds useful for preparing said compounds, pharmaceutical compositions and combinations comprising said compounds and the use of said compounds for manufacturing pharmaceutical compositions for the treatment or prophylaxis of diseases, in particular of cancer, as a sole agent or in combination with other active ingredients.

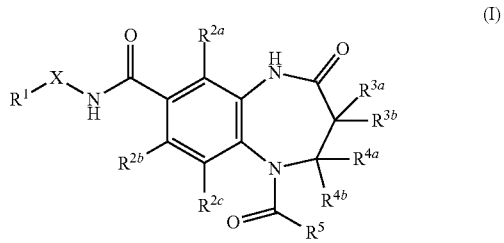

(I)

13 Claims, No Drawings

Specification includes a Sequence Listing.

(56) References Cited

OTHER PUBLICATIONS

Benayoun, B.A. et al. (2009). "A post-translational modification code for transcription factors: sorting through a sea of signals," Trends in Cell Biology 19(5): 189-197.
Cock-Rada, A.M. et al. (2012). "SMYD3 Promotes Cancer Invasion by Epigenetic Upregulation of the Metalloproteinase MMMP-9," Cancer Res 72(3): 810-820.
Database WPI Week 201758, Thomson Scientific, London, GB; AN 2017-472300, XP002785439.
Fu, W. et al. (2016). "Structural Basis for Substrate Preference of SMYD3, a SET Domain-containing Protein Lysine Methyltransferase," The Journal of Biological Chemistry 291(17): 9173-9180.
Goel, H.L. (2103). "VEGF targets the tumour cell," Nature Reviews Cancer 13(12): 871-882.
Hamamoto, R. et al. (2004). "SMYD3 encodes a histone methyltransferase involved in the proliferation of cancer cells," Nature Cell Biology 6(8): 731-740.
Hamamoto, R. et al. (2006) "Enhanced SMYD3 expression is essential for the growth of breast cancer cells," Cancer Sci 97(2): 113-118.
Hamamoto, R. et al. (2015). "Critical roles of non-histone protein lysine methylation in human tumorigenesis," Nature Reviews Cancer 15(2): 110-124.
Hamamoto, R. et al. (2016). "Dysregulation of protein methyltransferases human cancer: An emerging target class for anticancer therapy," Cancer Sci 107: 377-384.
He, C. et al. (2012). "High expression of trimethylated histone H3 lysine 4 is associated with poor prognosis in hepatocellular carcinoma," Human Pathology 43: 1425-1435.
Huang, J. et al. (2008). "The emerging field of dynamic lysine methylation of non-histone proteins," Current Opinion in Genetics & Development 18: 152-158.
Huang, L. et al. (2015). "CD147 and MMP-9 expressions in type II/III adenocarcinoma of esophagogastric junction and their clinicaopathological significances," Int J Clin Exp Pathol 8(2): 1929-1937.
International Search Report dated Oct. 22, 2018 for PCT Application No. PCT/EP2018/071649 filed Aug. 9, 2018, 5 pages.
Kim, H. et al. (2009). "Requirement of Histone Methyltransferase SMYD3 for Estrogen Receptor-mediated Transcription," The Journal of Biological Chemistry 284(30): 19867-19877.
Kunizaki, M. et al. (2007). "The Lysine 831 of Vascular Endothelial Growth Factor Receptor 1 is a Novel Target of Methylation by SMYD3," Cancer Res 67(22): 10759-10765.
Lanouette, S. et al. (2014). "The functional diversity of protein lysine methylation," Mol Syst Biol. 10: 724 (26 pages).
Liu, C. et al.(2007). "The Telomerase Reverse Transcriptase (hTERT) Gene is Target of the Histone Methyltransferase SMYD3," Cancer Res 67(6): 2626-2631.
Liu, C. et al. (2013). "SMYD3 as an Oncogenic Driver in Prostate Cancer by Stimulation of Androgen Receptor Transcription," J Natl Cancer Inst 105: 1719-1728.
Liu, Y. et al. (2015). "SMYD3 overexpression was a risk factor in the biological behavior and prognosis of gastric carcinoma," Tumor Biol. 36: 2685-2694.
Lopez, P. et al. (1996). "Transdifferentiated Retinal Pigment Epithelial Cells are Immunoreactive for Vascular Endothelial Growth Factor in Surgically Excised Age-Related Macular Degeneration—Related Choroidal Neovascular Membranes," Invest. Opththalmol. Vis. Sci. 37(5):855-868.
Luo, X.-G. et al.(2014). "Histone methyltransferase SMYD3 promotes MRTF-A-mediated transactivation of MYL9 and migration of MCF-7 breast cancer cells," Cancer Letters 344: 129-137.
Mair, B. et al. (2014). "Exploiting epigenetic vulnerabilities for cancer therapeutics," Trends in Pharmacological Sciences 35(3) 136-145.
Mazur, P.K. et al. (2014). "SMYD3 links lysine methylation of MAP3K2 to Ras-driven cancer," Nature 510(7504): 283-285 and supplemental pages.
Mitchell, L. H. (2016). "Novel Oxindole Sulfonamides and Sulfamides: EPZ031686, the First Orally Bioavailable Small Molecule SMYD3 Inhibitor," ACS Med. Chem. Lett. 7(2): 134-138.
Nagata, D. (2014). "Epigenetic control of Foxp3 by SMYD3 H3K4 histone methlytransferase controls iTreg development and regulates pathogenic T-cell responses during pulmonary viral infection," Mucosa Immunology 8(5): 1131-1143.
Pe'er, J. et al. (Jun. 1995). Hypoxia-Induced Expression of Vascular Endothelial Growth Factor by Retinal Cells is a Common Factor Neovascularizing Ocular Diseases, Lab Invest. 72(6): 638-645.
Peserico, A. et al. (2015). "A SMYD3 Small-Molecule Inhibitor Impairing Cancer Cell Growth," J Cell Physiol., 230 (10): 2447-2460.
Sims, R. J. (Oct. 2008). "Is there a code embedded in proteins that is based on post-translational modifications?" Nat Rev Mol Cell Biol., 9: 815-820.
Tsuge, M. (2005). "A variable number of tandem repeats polymorphism in an E2F-1 binding element in the 5' flanking region of SMYK3 is a risk factor for human cancers," Nat Genet. 37(10): 1104-1107.
Van Aller, G.S. (2012). "Smyd3 regulates cancer cell phenotypes and catalyzes histone H4 lysine 5 methylation," Epigenetics 7(4): 340-343.
Wagner, T. et al. (2012). "New lysine methyltransferase drug targets in cancer," Nat Biotechnol., 30(7): 622-623.
Wang, H. et al. (2008). "Association of the variable number of tandem repeats polymorphism in the promoter region of the SMYD3 gene with risk of esophageal squamous cell carcinoma in relation to tobacco smoking," Cancer Sci., 99(4): 787-791.
Wang, S-Z et al. (2008). "Knockdown of SMYKD3 by RNA interference inhibits cervical carcinoma cell growth and invasion in vitro," BMB Rep., 41(4): 294-299.
Wu, C-Y, et al. (2002). "Soluble Polymer-Supported Synthesis of Benzodiazepinones," Bioorganic & Medicinal Chemistry Letters 12: 959-962.
Ying et al. (2014). "Cancer signaling: when phosphorylation meets methylation," Cell Research 24(11): 1282-1283.
Zeng, B. et al. (2012). "Epigenetic regulation of miR-124 by Hepatitis C Virus core protein promotes migration and invasion of intrahepatic cholangiocarcinoma cells by targeting SMYD3," FEBS Lett., 586(19): 3271-3278.
Zhu, Y. et al (2016). "SMYD3 stimulates EZR and LOXL2 transcription to enhance proliferation, migration, and invasion in esophageal squamous cell carcinoma," Human Pathology 52: 153-163.
Zou, J-N. et al. (2009). "Knockdown of SMYD3 by RNA interference down-regulates c-Met expression and inhibits cell migration and invasion induced by HGF," Cancer Letters 280: 78-85.

\* cited by examiner

SEQUENCE LISTING

<160> NUMBER OF SEQ ID NOS: 1

<210> SEQ ID NO 1
<211> LENGTH: 26
<212> TYPE: PRT
<213> ORGANISM: Artificial Sequence
<220> FEATURE:
<223> OTHER INFORMATION: biotinylated peptide derived from MAP3K2

<400> SEQUENCE: 1

```
Asp Tyr Asp Asn Pro Ile Phe Glu Lys Phe Gly Lys Gly Gly Thr Tyr
1               5                   10                  15

Pro Arg Arg Tyr His Val Ser Tyr His Lys
            20                  25
```

4-OXO-2,3,4,5-TETRAHYDRO-1H-1,5-BENZO-DIAZEPINE-7-CARBOXAMIDES

CROSS REFERENCE TO RELATED APPLICATIONS

This application is a national stage application under 35 U.S.C. § 371 of International Application No. PCT/EP2018/071649, filed internationally on Aug. 9, 2018, which claims the benefit of priority to European Application No. 17186334.3, filed Aug. 15, 2017; European Application No. 18154895.9, filed Feb. 2, 2018; and European Application No. 18175162.9, filed May 30, 2018.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052040400SEQLIST.TXT, date recorded: Feb. 10, 2020, size: 1 KB).

The present invention covers 4-oxo-2,3,4,5-tetrahydro-1H-1,5-benzodiazepine-7-carboxamide compounds of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular cancer, as a sole agent or in combination with other active ingredients.

BACKGROUND

A large body of evidence has indicated that protein lysine methyltransferases dysregulation is involved in the development and progression of various diseases, including cancer, and these enzymes are considered to be potential therapeutic targets (Lanouette et al., Mol Syst Biol., 2014, 10:724). Although most studies on this enzyme family have focused on histone methylation, many reports have revealed that these enzymes also regulate the methylation dynamics of non-histone proteins (Hamamto et al., Nat Rev Cancer, 2015, 15(2):110-24; Huang and Berger, Curr Opin Genet Dev., 2008, 18(2):152-8). Lysine methylation has been shown to regulate protein-protein interactions, stability, localization, and/or enzymatic activities of those proteins (Sims and Reinberg, Nat Rev Mol Cell Biol., 2008, 9:815-20). Therefore post translational modification of non-histone proteins (e.g. transcription factors) can substantially alter protein function, extending the regulatory role of lysine methylation to multiple cellular pathways (Benayoun and Veitia, Trends Cell Biol., 2009, 19(5):189-97). Accordingly, lysine was shown to influence different pathways directly linked to oncogenic transformation, providing a rationale for the involvement of lysine methylation in cancer and for developing inhibitors for therapeutic intervention (Hamamoto and Nakamura, Cancer Sci., 2016, 107(4):377-84; Mair et al., Trends Pharmacol Sci., 2014, 35(3):136-45; Wagner and Jung, Nat Biotechnol., 2012, 30(7):622-3).

In the present invention, inhibitors directed against the lysine specific methyltransferase SET and MYND domain-containing protein 3 (SMYD3) are described. SMYD3 is a catalytic SET domain containing protein methyltransferase reported to methylate several lysine residues on histone and non-histone proteins. In cancers, several studies detected abnormally high expression of SMYD3. Originally SMYD3 has been identified as an overexpressed gene in colorectal and hepatocellular carcinomas (Hamamoto et al., Nat Cell Biol., 2004, 6(8):731-40; He et al., Hum Pathol., 2012, 43(9):1425-35). Upregulation of SMYD3 was connected to variable number of tandem repeats polymorphism in the promoter region. The tandem repeat motive is an E2F-1 binding element and number variation is leading to differences in SMYD3 protein expression. Those differences were proposed as susceptibility factor for developing hepatocellular, colorectal, or breast carcinomas (Tsuge et al., Nat Genet. 2005, 37(10):1104-7). Additional studies reported overexpression of SMYD3 in cancer cell lines as well as in esophageal squamous cell carcinoma (ESCC) and gastric cancer tumors. (Wang et al., Cancer Sci., 2008, 99(4):787-91; Zhu et al., Hum Pathol., 2016, 52:153-63; Liu et al., Tumour Biol., 2015, 36(4):2685-94). Notably higher SMYD3 expression in gastric cancer patients is significantly associated with primary tumor size, lymph node metastasis, and TNM stage, and identified as a significantly independent negative prognostic factor of the overall survival (OS), further indicating an oncogenic role of SMYD3 (Liu et al., Tumour Biol., 2015, 36(4):2685-94). In validation experiments, knockdown of SMYD3 in breast cancer, ESCC, pancreatic adenocarcinoma, cholangiocarcinoma, and cervical carcinoma cancer cell line models significantly reduced cell proliferation (Hamamoto et al., Cancer Sci., 2006, 97(2):113-8; Mazur et al., Nature, 2014, 510(7504):283-7; Wang et al., BMB Rep., 2008, 41(4):294-9; Zeng et al., FEBS Lett., 2012, 586(19):3271-8; Zhu et al., Hum Pathol., 2016, 52:153-63).

Mechanistically SMYD3 was characterized to bi/tri-methylate H3 lysine 4 (H3K4) (Hamamoto et al., Nat Cell Biol., 2004, 6(8):731-40) a chromatin mark associated with active gene promotors. In addition histone 4 was reported to be methylated by SMYD3 at lysine 5 (Aller et al., Epigenetics, 2012, 4:340-3), but functional consequences for gene expression remains to be elusive. Methylation of H3K4 by SMYD3 has been connected to an aberrant increased transcription of cancer promoting genes in cell line models. Examples for genes regulated directly by SMYD3 involved in growth, adhesion and migration of cancer cells are the proto-oncogene c-MET (Zou et al., Cancer Lett., 2009, 280:78-85), matrix metalloproteinase 9 (MMP9) (Huang et al., Int J Clin Exp Pathol., 2015, 8:1929-1937; Cock-Rada et al., Cancer Res., 2012, 72(3):810-20), the androgen receptor (AR) (Liu et al., J Natl Cancer Inst., 2013, 105(22):1719-28), telomerase reverse transcriptase (hTERT) (Liu et al., Cancer Res., 2007, 67(6):2626-31), and myosin regulatory light chain 9 (MYL9) (Luo et al., Cancer Lett., 2014, 344(1):129-137). In breast cancer models SMYD3 activity on histone methylation has been identified as an essential cofactor mechanism of estrogen receptor dependent transcription (Kim et al., J Biol Chem., 2009, 284(30):19867-77). H3K4 methylation by SMYD3 has also been described in immune cell differentiation regulation. SMYD3 is critical important for the generation of regulatory T cells, and modulation of proinflammatory cytokine production by controlling the expression of the transcription factor Foxp3 (Nagata et al., Mucosal Immunol., 2015, 8(5):1131-43).

In addition to the function of SMYD3 in transcriptional regulation, several studies uncovered an important role of SMYD3 methylation activity on non-histone proteins closely connected to cancer. For example, the vascular endothelial growth factor receptor 1 (VEGFR1) was also found to be methylated by SMYD3 at lysine 831. VEGFR1 is a receptor tyrosine kinase which mediates signaling that is involved in cell proliferation and angiogenesis in cancer (Goel and Mercurio, Nat Rev Cancer., 2013, 13(12):871-82). The methylated lysine is located in the kinase domain and methylation of VEGFR1 and methylation enhanced its kinase activity in cancer cell line models (Kunizaki et al., Cancer Res., 2007, 67(22):10759-65; Fu et al., J Biol Chem., 2016, 291(17):9173-80).

MAP3K2 (MEKK2), a member of the serine/threonine protein kinase family is another reported target of SMYD3 mediated methylation. Methylation of MAP3K2 at lysine 260 has been validated to activate the RAS-RAF-MEK-ERK signaling module by blocking away the PP2A phosphatase complex which is a negative regulator of the MAPK pathway (Mazur et al., Nature, 2014, 510(7504):283-7). In the same study it has been demonstrated that tumor development in response to oncogenic Ras was inhibited by abrogating SMYD3 catalytic activity in mouse models for pancreatic ductal and lung adenocarcinomas. Those findings suggest SMYD3 as a potential therapeutic target to treat pancreatic and lung cancers driven by RAS, as well as potentially other RAS-driven tumors (Ying and DePinho, Cell Res., 2014, 24(11):1282-3). These studies indicate that the SMYD3 proteins play an essential role in various pathologies. It would therefore be desirable to find potent and selective inhibitors which prevent the SMYD3 methylation activity. First inhibitors for SMYD3 have been described and are so far only tested in few pre-clinical experiments (Mitchell et al., ACS Med Chem Lett., 2015, 7(2):134-8; Peserico et al., J Cell Physiol., 2015, 230(10): 2447-60). Novel inhibitors should also have suitable pharmacokinetic properties which allow inhibition of these interactions in vivo, i.e. in patients.

The present invention covers 4-oxo-2,3,4,5-tetrahydro-1H-1,5-benzodiazepine-7-carboxamide compounds of general formula (I) which inhibit SMYD3 and can be prophylactically and therapeutically used in a wide range of diseases, especially in hyperproliferative diseases, and more especially in cancer, respectively tumor treatment.

DESCRIPTION OF THE INVENTION

In accordance with a first aspect, the present invention covers compounds of general formula (I):

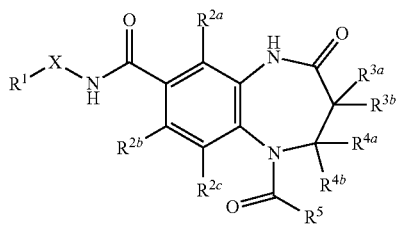

in which:
X represents $C_2$-$C_3$-alkylen;
$R^1$ represents $C_3$-$C_5$-cycloalkyl;
$R^{2a}$ represents hydrogen, hydroxy, halogen, cyano, $C_1$-$C_3$-alkyl, $C_1$-$C_3$-haloalkyl, $C_1$-$C_3$-alkoxy or $C_1$-$C_3$-haloalkoxy;
$R^{2b}$ represents hydrogen, hydroxy, halogen, cyano, $C_1$-$C_3$-alkyl, $C_1$-$C_3$-haloalkyl, $C_1$-$C_3$-alkoxy or $C_1$-$C_3$-haloalkoxy;
$R^{2c}$ represents hydrogen, hydroxy, halogen, cyano, $C_1$-$C_3$-alkyl, $C_1$-$C_3$-haloalkyl, $C_1$-$C_3$-alkoxy or $C_1$-$C_3$-haloalkoxy;
$R^{3a}$ represents hydrogen or $C_1$-$C_3$-alkyl;
$R^{3b}$ represents hydrogen or $C_1$-$C_3$-alkyl or
together with the carbon atom to which they are attached $R^{3a}$ and $R^{3b}$ form a $C_3$-$C_6$-cycloalkyl group which is optionally substituted one, two or three times, independently of each other, with halogen;
$R^{4a}$ represents hydrogen or $C_1$-$C_3$-alkyl;
$R^{4b}$ represents hydrogen or $C_1$-$C_3$-alkyl or
together with the carbon atom to which they are attached $R^{4a}$ and $R^{4b}$ form a $C_3$-$C_6$-cycloalkyl group which is optionally substituted one, two or three times, independently of each other, with halogen;
$R^5$ represents phenyl, wherein said phenyl is optionally substituted one, two or three times, independently of each other, with $R^{2b}$,
5- to 6-membered heteroaryl, wherein said 5- to 6-membered heteroaryl is optionally substituted one, two or three times, independently of each other, with $R^{2c}$, $NR^6R^7$ or
5- to 8-membered nitrogen containing heterocyclic ring, to which nitrogen the ring is attached, said ring optionally containing one additional heteroatom selected from O, S, NH, $NR^a$ in which $R^a$ represents a $C_1$-$C_4$-alkyl, $C_1$-$C_4$-haloalkyl or $C_2$-$C_4$-hydroxyalkyl group and the ring being optionally substituted one, two or three times, independently of each other, with halogen, $NR^8R^9$ or an oxo group;
$R^6$, $R^7$ represent, independently from each other, hydrogen, $C_1$-$C_4$-alkyl, $C_1$-$C_4$-haloalkyl, $C_3$-$C_6$-cycloalkyl or a 5- to 8-membered nitrogen containing heterocyclic ring, which ring is attached to a carbon atom, said ring optionally contains one additional heteroatom selected from O, S, NH, $NR^a$ in which $R^a$ represents a $C_1$-$C_4$-alkyl, $C_1$-$C_4$-haloalkyl or $C_2$-$C_4$-hydroxyalkyl group and the ring being optionally substituted with halogen, $C_1$-$C_3$-alkyl, $C_1$-$C_4$-haloalkyl, $NR^8R^9$ or an oxo group;
$R^8$, $R^9$ represent, independently from each other, hydrogen, $C_1$-$C_4$-alkyl, $C_1$-$C_4$-haloalkyl;
and stereoisomers, tautomers, N-oxides, hydrates, solvates, and salts thereof, and mixtures of same.

DEFINITIONS

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

The term "comprising" when used in the specification includes "consisting of".

The terms as mentioned in the present text have the following meanings:

The term "halogen", respectively "halogen atom" means a fluorine, chlorine or bromine atom, particularly a fluorine or chlorine atom.

The term "$C_1$-$C_4$-alkyl" means a linear or branched, saturated, monovalent hydrocarbon group having 1, 2, 3 or 4 carbon atoms, e.g. a methyl, ethyl, propyl, isopropyl, butyl, sec-butyl, isobutyl or tert-butyl. Particularly, said group has 1, 2 or 3 carbon atoms ("$C_1$-$C_3$-alkyl"), e.g. a methyl, ethyl, propyl or isopropyl group, more particularly 1 or 2 carbon atoms ("$C_1$-$C_2$-alkyl"), e.g. a methyl or ethyl group.

The term "oxo group means a doubly attached oxygen atom =O. Oxo may be attached to atoms of suitable valency, for example to a saturated carbon atom. Preference is given to binding to carbon with formation of a carbonyl group —C(=O)—.

The term "$C_2$-$C_4$-hydroxyalkyl" means a linear or branched, saturated, monovalent hydrocarbon group having 2, 3 or 4 carbon atoms, e.g. a ethyl, propyl, isopropyl, butyl, sec-butyl, isobutyl or tert-butyl, and in which 1 hydrogen atom is replaced with a hydroxy group, e.g. a 2-hydroxyethyl, 3-hydroxypropyl, 2-hydroxypropyl, 3-hydroxy-2-methyl-propyl, 2-hydroxy-2-methyl-propyl group.

The term "$C_1$-$C_4$-haloalkyl" means a linear or branched, saturated, monovalent hydrocarbon group in which the term "$C_1$-$C_4$-alkyl" is as defined supra, and in which one or more of the hydrogen atoms are replaced, identically or differently, with a halogen atom. Particularly, said halogen atom is a fluorine atom. Said $C_1$-$C_4$-haloalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

The term "$C_1$-$C_3$-alkoxy" means a linear or branched, saturated, monovalent group of formula ($C_1$-$C_3$-alkyl)-O—, in which the term "$C_1$-$C_3$-alkyl" is as defined supra, e.g. a methoxy, ethoxy, n-propoxy or isopropoxy.

The term "$C_1$-$C_3$-haloalkoxy" means a linear or branched, saturated, monovalent $C_1$-$C_3$-alkoxy group, as defined supra, in which one or more of the hydrogen atoms is replaced, identically or differently, with a halogen atom. Particularly, said halogen atom is a fluorine atom. Said $C_1$-$C_3$-haloalkoxy group is, for example, fluoromethoxy, difluoromethoxy, trifluoromethoxy, 2,2,2-trifluoroethoxy or pentafluoroethoxy.

The term "$C_3$-$C_6$-cycloalkyl" means a saturated, monovalent, mono- or bicyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl group.

The term "$C_2$-$C_3$-alkylene" means a linear, saturated, bivalent hydrocarbon group having 2 or 3 carbon atoms, e.g. an ethylene or propylene group. Particularly, said group has 2 carbon atoms ("$C_2$-alkylene"), e.g. an ethylene group.

The term "heteroaryl" means a monovalent, monocyclic, bicyclic or tricyclic aromatic ring having 5, 6, 8, 9, 10, 11, 12, 13 or 14 ring atoms (a "5- to 14-membered heteroaryl" group), particularly 5, 6, 9 or 10 ring atoms, which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl; or a tricyclic heteroaryl group, such as, for example, carbazolyl, acridinyl or phenazinyl; or a 9-membered heteroaryl group, such as, for example, benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, such as, for example, quinolinyl, quinazolinyl, isoquinolinyl, cinnolinyl, phthalazinyl, quinoxalinyl or pteridinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "5-membered heteroaryl" means a monovalent, monocyclic aromatic ring having 5 ring atoms, which contains at least one ring heteroatom and optionally one, two or three further ring heteroatoms from the series: N, O and/or S, and which is bound via a ring carbon atom or optionally via a ring nitrogen atom (if allowed by valency).

Said 5-membered heteroaryl group can be, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl.

Particularly, the heteroaryl group is a oxazolyl group.

The term "5- to 8-membered nitrogen containing heterocyclic ring", is to be understood as meaning a saturated or partially unsaturated, monovalent, mono- or bicyclic hydrocarbon ring which contains 4, 5, 6 or 7 carbon atoms, and one nitrogen atom, optionally containing one further heteroatom (or a heteroatom-containing group) selected from the group consisting of O, S, NH and NR$^a$.

The term "$C_1$-$C_4$", as used in the present text, e.g. in the context of the definition of "$C_1$-$C_4$-alkyl" or "$C_1$-$C_4$-haloalkyl" means an alkyl group having a finite number of carbon atoms of 1 to 4, i.e. 1, 2, 3 or 4 carbon atoms.

Further, as used herein, the term "$C_1$-$C_3$", as used in the present text, e.g. in the context of the definition of "$C_1$-$C_3$-alkyl" or "$C_1$-$C_3$-haloalkyl", means an alkyl group having a finite number of carbon atoms of 1 to 3, i.e. 1, 2 or 3 carbon atoms.

Further, as used herein, the term "$C_2$-$C_4$", as used in the present text, e.g. in the context of the definition of "$C_2$-$C_4$-hydroxyalkyl", means a hydroxyalkyl group having a finite number of carbon atoms of 2 to 4, i.e. 2, 3 or 4 carbon atoms.

When a range of values is given, said range encompasses each value and sub-range within said range.

For example:

"$C_1$-$C_4$" encompasses $C_1$, $C_2$, $C_3$, $C_4$, $C_1$-$C_4$, $C_1$-$C_3$, $C_1$-$C_2$, $C_2$-$C_4$, $C_2$-$C_3$ and $C_3$-$C_4$;

"$C_2$-$C_4$" encompasses $C_2$, $C_3$, $C_4$, $C_2$-$C_4$, $C_2$-$C_3$ and $C_3$-$C_4$;

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)-sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{125}$I, $^{129}$I and $^{131}$I respectively.

With respect to the treatment and/or prophylaxis of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3$H or $^{14}$C, are incorporated are useful e.g. in drug and/or substrate tissue distribution studies. These isotopes are particularly preferred for the ease of their incorporation and detectability. Positron emitting isotopes such as $^{18}$F or $^{11}$C may be incorporated into a compound of general formula (I). These isotopic variants of the compounds of general formula (I) are useful for in vivo imaging applications. Deuterium-containing and $^{13}$C-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from D$_2$O can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome P$_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethylglucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x $CF_3COOH$", "x Na", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

In accordance with a second embodiment of the first aspect, the present invention covers compounds of general formula (I), supra, in which:

X represents $C_2$-$C_3$-alkylen;
$R^1$ represents $C_3$-$C_4$-cycloalkyl;
$R^{2a}$ represents hydrogen, hydroxy, halogen, cyano, $C_1$-$C_3$-alkyl, $C_1$-$C_3$-haloalkyl, $C_1$-$C_3$-alkoxy or $C_1$-$C_3$-haloalkoxy;
$R^{2b}$ represents hydrogen, hydroxy, halogen, cyano, $C_1$-$C_3$-alkyl, $C_1$-$C_3$-haloalkyl, $C_1$-$C_3$-alkoxy or $C_1$-$C_3$-haloalkoxy;
$R^{2c}$ represents hydrogen, hydroxy, halogen, cyano, $C_1$-$C_3$-alkyl, $C_1$-$C_3$-haloalkyl, $C_1$-$C_3$-alkoxy or $C_1$-$C_3$-haloalkoxy;
$R^{3a}$ represents hydrogen or $C_1$-$C_2$-alkyl;
$R^{3b}$ represents hydrogen or $C_1$-$C_2$-alkyl or
together with the carbon atom to which they are attached $R^{3a}$ and $R^{3b}$ form a cyclopropyl group which is optionally substituted one, two or three times, independently of each other, with halogen;
$R^{4a}$ represents hydrogen or $C_1$-$C_2$-alkyl;
$R^{4b}$ represents hydrogen or $C_1$-$C_2$-alkyl or
together with the carbon atom to which they are attached $R^{4a}$ and $R^{4b}$ form a cyclopropyl group which is optionally substituted one, two or three times, independently of each other, with halogen;
$R^5$ represents phenyl, wherein said phenyl is optionally substituted one or two times, independently of each other, with $R^{2b}$,
5- to 6-membered heteroaryl, wherein said 5- to 6-membered heteroaryl is optionally substituted one or two times, independently of each other, with $R^{2c}$, $NR^6R^7$ or
5- to 7-membered nitrogen containing heterocyclic ring, to which nitrogen the ring is attached, said ring optionally containing one additional heteroatom selected from O, NH, $NR^a$ in which $R^a$ represents a $C_1$-$C_4$-alkyl, $C_1$-$C_4$-haloalkyl or $C_2$-$C_4$-hydroxyalkyl group and the ring being optionally substituted one or two times, independently of each other, with halogen or $NR^8R^9$;
$R^6$, $R^7$ represent, independently from each other, hydrogen, $C_1$-$C_4$-alkyl, $C_3$-$C_6$-cycloalkyl or 5- to 6-membered nitrogen containing heterocyclic ring, which ring is attached to a carbon atom, said ring optionally containing one additional heteroatom selected from O, NH, $NR^a$ in which $R^a$ represents a $C_1$-$C_4$-alkyl, $C_1$-$C_4$-haloalkyl or $C_2$-$C_4$-hydroxyalkyl group and the ring being optionally substituted with halogen, $C_1$-$C_3$-alkyl, $C_1$-$C_4$-haloalkyl or $NR^8R^9$;
$R^8$, $R^9$ represent, independently from each other, hydrogen, $C_1$-$C_3$-alkyl, $C_1$-$C_3$-haloalkyl;

and stereoisomers, tautomers, N-oxides, hydrates, solvates, and salts thereof, and mixtures of same.

In accordance with a third embodiment of the first aspect, the present invention covers compounds of general formula (I), supra, in which:

X represents ethylen;
$R^1$ represents $C_3$-$C_4$-cycloalkyl;
$R^{2a}$ represents hydrogen;
$R^{2b}$ represents hydrogen;
$R^{2c}$ represents hydrogen or methyl;
$R^{3a}$ represents hydrogen or methyl;
$R^{3b}$ represents hydrogen or methyl
$R^{4a}$ represents hydrogen or methyl;
$R^{4b}$ represents hydrogen or methyl;
$R^5$ represents phenyl,
3-methyl-1,2-oxazol-4-yl
$NR^6R^7$ or
5- to 7-membered nitrogen containing heterocyclic ring, to which nitrogen the ring is attached, said ring optionally containing one additional heteroatom selected from NH, $NR^a$ in which $R^a$ represents ethyl, 2,2,2-trifluoroethyl or 2-hydroxyethyl and the ring being optionally substituted once with $NH_2$ or $NH—CH_2CF_3$ and twice with fluoro;
$R^6$, $R^7$ represent, independently from each other, hydrogen, methyl or 6-membered nitrogen containing heterocyclic ring, which ring is attached to a carbon atom and optionally substituted with ethyl or 2,2,2-trifluoroethyl;

and stereoisomers, tautomers, N-oxides, hydrates, solvates, and salts thereof, and mixtures of same.

In a further embodiment of the first aspect, the present invention covers compounds of formula (I), supra, in which:
X represents $C_2$-$C_3$-alkylen;
and stereoisomers, tautomers, N-oxides, hydrates, solvates, and salts thereof, and mixtures of same.

In a further embodiment of the first aspect, the present invention covers compounds of formula (I), supra, in which:
X represents ethylen;
and stereoisomers, tautomers, N-oxides, hydrates, solvates, and salts thereof, and mixtures of same.

In a further embodiment of the first aspect, the present invention covers compounds of formula (I), supra, in which:
$R^1$ represents $C_3$-$C_5$-cycloalkyl;
and stereoisomers, tautomers, N-oxides, hydrates, solvates, and salts thereof, and mixtures of same.

In a further embodiment of the first aspect, the present invention covers compounds of formula (I), supra, in which:
$R^1$ represents $C_3$-$C_4$-cycloalkyl;
and stereoisomers, tautomers, N-oxides, hydrates, solvates, and salts thereof, and mixtures of same.

In a further embodiment of the first aspect, the present invention covers compounds of formula (I), supra, in which:
$R^{2a}$ represents hydrogen, hydroxy, halogen, cyano, $C_1$-$C_3$-alkyl, $C_1$-$C_3$-haloalkyl, $C_1$-$C_3$-alkoxy or $C_1$-$C_3$-haloalkoxy;
and stereoisomers, tautomers, N-oxides, hydrates, solvates, and salts thereof, and mixtures of same.

In a further embodiment of the first aspect, the present invention covers compounds of formula (I), supra, in which:
$R^{2a}$ represents hydrogen;
and stereoisomers, tautomers, N-oxides, hydrates, solvates, and salts thereof, and mixtures of same.

In a further embodiment of the first aspect, the present invention covers compounds of formula (I), supra, in which:
$R^{2b}$ represents hydrogen, hydroxy, halogen, cyano, $C_1$-$C_3$-alkyl, $C_1$-$C_3$-haloalkyl, $C_1$-$C_3$-alkoxy or $C_1$-$C_3$-haloalkoxy;
and stereoisomers, tautomers, N-oxides, hydrates, solvates, and salts thereof, and mixtures of same.

In a further embodiment of the first aspect, the present invention covers compounds of formula (I), supra, in which:
$R^{2b}$ represents hydrogen;
and stereoisomers, tautomers, N-oxides, hydrates, solvates, and salts thereof, and mixtures of same.

In a further embodiment of the first aspect, the present invention covers compounds of formula (I), supra, in which:
$R^{2c}$ represents hydrogen, hydroxy, halogen, cyano, $C_1$-$C_3$-alkyl, $C_1$-$C_3$-haloalkyl, $C_1$-$C_3$-alkoxy or $C_1$-$C_3$-haloalkoxy;
and stereoisomers, tautomers, N-oxides, hydrates, solvates, and salts thereof, and mixtures of same.

In a further embodiment of the first aspect, the present invention covers compounds of formula (I), supra, in which:
$R^{2c}$ represents hydrogen or methyl;
and stereoisomers, tautomers, N-oxides, hydrates, solvates, and salts thereof, and mixtures of same.

In a further embodiment of the first aspect, the present invention covers compounds of formula (I), supra, in which:
$R^{2c}$ represents hydrogen;
and stereoisomers, tautomers, N-oxides, hydrates, solvates, and salts thereof, and mixtures of same.

In a further embodiment of the first aspect, the present invention covers compounds of formula (I), supra, in which:
$R^{3a}$ represents hydrogen or $C_1$-$C_3$-alkyl;
and stereoisomers, tautomers, N-oxides, hydrates, solvates, and salts thereof, and mixtures of same.

In a further embodiment of the first aspect, the present invention covers compounds of formula (I), supra, in which:
$R^{3a}$ represents hydrogen or $C_1$-$C_2$-alkyl;
and stereoisomers, tautomers, N-oxides, hydrates, solvates, and salts thereof, and mixtures of same.

In a further embodiment of the first aspect, the present invention covers compounds of formula
$R^{3a}$ represents hydrogen or methyl;
and stereoisomers, tautomers, N-oxides, hydrates, solvates, and salts thereof, and mixtures of same.

In a further embodiment of the first aspect, the present invention covers compounds of formula (I), supra, in which:
$R^{3b}$ represents hydrogen or $C_1$-$C_3$-alkyl;
and stereoisomers, tautomers, N-oxides, hydrates, solvates, and salts thereof, and mixtures of same.

In a further embodiment of the first aspect, the present invention covers compounds of formula (I), supra, in which:
$R^{3b}$ represents hydrogen or $C_1$-$C_2$-alkyl;
and stereoisomers, tautomers, N-oxides, hydrates, solvates, and salts thereof, and mixtures of same.

In a further embodiment of the first aspect, the present invention covers compounds of formula
$R^{3b}$ represents hydrogen or methyl;
and stereoisomers, tautomers, N-oxides, hydrates, solvates, and salts thereof, and mixtures of same.

In a further embodiment of the first aspect, the present invention covers compounds of formula
$R^{3a}$ and $R^{3b}$ together with the carbon atom to which they are attached $R^{3a}$ and $R^{3b}$ form a $C_3$-$C_6$-cycloalkyl group which is optionally substituted one, two or three times, independently of each other, with halogen;
and stereoisomers, tautomers, N-oxides, hydrates, solvates, and salts thereof, and mixtures of same.

In a further embodiment of the first aspect, the present invention covers compounds of formula
$R^{3a}$ and $R^{3b}$ together with the carbon atom to which they are attached $R^{3a}$ and $R^{3b}$ form a cyclopropyl group which is optionally substituted one, two or three times, independently of each other, with halogen;
and stereoisomers, tautomers, N-oxides, hydrates, solvates, and salts thereof, and mixtures of same.

In a further embodiment of the first aspect, the present invention covers compounds of formula (I), supra, in which:
$R^{4a}$ represents hydrogen or $C_1$-$C_3$-alkyl;
and stereoisomers, tautomers, N-oxides, hydrates, solvates, and salts thereof, and mixtures of same.

In a further embodiment of the first aspect, the present invention covers compounds of formula (I), supra, in which:
$R^{4a}$ represents hydrogen or $C_1$-$C_2$-alkyl;
and stereoisomers, tautomers, N-oxides, hydrates, solvates, and salts thereof, and mixtures of same.

In a further embodiment of the first aspect, the present invention covers compounds of formula
$R^{4a}$ represents hydrogen or methyl;
and stereoisomers, tautomers, N-oxides, hydrates, solvates, and salts thereof, and mixtures of same.

In a further embodiment of the first aspect, the present invention covers compounds of formula (I), supra, in which:
$R^{4b}$ represents hydrogen or $C_1$-$C_3$-alkyl;
and stereoisomers, tautomers, N-oxides, hydrates, solvates, and salts thereof, and mixtures of same.

In a further embodiment of the first aspect, the present invention covers compounds of formula (I), supra, in which:
$R^{4b}$ represents hydrogen or $C_1$-$C_2$-alkyl;
and stereoisomers, tautomers, N-oxides, hydrates, solvates, and salts thereof, and mixtures of same.

In a further embodiment of the first aspect, the present invention covers compounds of formula
$R^{4b}$ represents hydrogen or methyl;
and stereoisomers, tautomers, N-oxides, hydrates, solvates, and salts thereof, and mixtures of same.

In a further embodiment of the first aspect, the present invention covers compounds of formula
$R^{4a}$ and $R^{4b}$ together with the carbon atom to which they are attached $R^{3a}$ and $R^{3b}$ form a $C_3$-$C_6$-cycloalkyl group which is optionally substituted one, two or three times, independently of each other, with halogen;
and stereoisomers, tautomers, N-oxides, hydrates, solvates, and salts thereof, and mixtures of same.

In a further embodiment of the first aspect, the present invention covers compounds of formula
$R^{4a}$ and $R^{4b}$ together with the carbon atom to which they are attached $R^{3a}$ and $R^{3b}$ form a cyclopropyl group which is optionally substituted one, two or three times, independently of each other, with halogen;
and stereoisomers, tautomers, N-oxides, hydrates, solvates, and salts thereof, and mixtures of same.

In a further embodiment of the first aspect, the present invention covers compounds of formula (I), supra, in which:
$R^5$ represents phenyl, wherein said phenyl is optionally substituted one, two or three times, independently of each other, with $R^{2b}$,
5- to 6-membered heteroaryl, wherein said 5- to 6-membered heteroaryl is optionally substituted one, two or three times, independently of each other, with $R^{2c}$, $NR^5R^7$ or
5- to 8-membered nitrogen containing heterocyclic ring, to which nitrogen the ring is attached, said ring optionally contains one additional heteroatom selected from O, S, NH, $NR^a$ in which $R^a$ represents a $C_1$-$C_4$-alkyl, $C_1$-$C_4$-haloalkyl or $C_2$-$C_4$-hydroxyalkyl group and the ring being optionally substituted one, two or three times, independently of each other, with halogen, $NR^8R^9$ or an oxo group;
and stereoisomers, tautomers, N-oxides, hydrates, solvates, and salts thereof, and mixtures of same.

In a further embodiment of the first aspect, the present invention covers compounds of formula (I), supra, in which:
$R^5$ represents phenyl, wherein said phenyl is optionally substituted one or two times, independently of each other, with $R^{2b}$,
5- to 6-membered heteroaryl, wherein said 5- to 6-membered heteroaryl is optionally substituted one or two times, independently of each other, with $R^{2c}$, $NR^6R^7$ or
5- to 7-membered nitrogen containing heterocyclic ring, to which nitrogen the ring is attached, said ring optionally containing one additional heteroatom selected from O, NH, $NR^a$ in which $R^a$ represents a $C_1$-$C_4$-alkyl, $C_1$-$C_4$-haloalkyl or $C_2$-$C_4$-hydroxyalkyl group and the ring being optionally substituted one or two times, independently of each other, with halogen or $NR^8R^9$;
and stereoisomers, tautomers, N-oxides, hydrates, solvates, and salts thereof, and mixtures of same.

In a further embodiment of the first aspect, the present invention covers compounds of formula (I), supra, in which:
$R^5$ represents phenyl,
3-methyl-1,2-oxazol-4-yl
$NR^6R^7$ or
5- to 7-membered nitrogen containing heterocyclic ring, to which nitrogen the ring is attached, said ring optionally containing one additional heteroatom selected from NH, $NR^a$ in which $R^a$ represents ethyl, 2,2,2-trifluoroethyl or 2-hydroxyethyl and the ring being optionally substituted once with $NH_2$ or NH—$CH_2CF_3$ and twice with fluoro;
and stereoisomers, tautomers, N-oxides, hydrates, solvates, and salts thereof, and mixtures of same.

In a further embodiment of the first aspect, the present invention covers compounds of formula (I), supra, in which:
$R^6$, $R^7$ represent, independently from each other, hydrogen, $C_1$-$C_4$-alkyl, $C_1$-$C_4$-haloalkyl, $C_3$-$C_6$-cycloalkyl or a 5- to 8-membered nitrogen containing heterocyclic ring, which ring is attached to a carbon atom, said ring optionally contains one additional heteroatom selected from O, S, NH, $NR^a$ in which $R^a$ represents a $C_1$-$C_4$-alkyl, $C_1$-$C_4$-haloalkyl or $C_2$-$C_4$-hydroxyalkyl group and the ring being optionally substituted with halogen, $C_1$-$C_3$-alkyl, $C_1$-$C_4$-haloalkyl, $NR^8R^9$ or an oxo group;
and stereoisomers, tautomers, N-oxides, hydrates, solvates, and salts thereof, and mixtures of same.

In a further embodiment of the first aspect, the present invention covers compounds of formula (I), supra, in which:
$R^6$, $R^7$ represent, independently from each other, hydrogen, $C_1$-$C_4$-alkyl, $C_3$-$C_6$-cycloalkyl or 5- to 6-membered nitrogen containing heterocyclic ring, which ring is attached to a carbon atom, said ring optionally containing one additional heteroatom selected from O, NH, $NR^a$ in which $R^a$ represents a $C_1$-$C_4$-alkyl, $C_1$-$C_4$-haloalkyl or $C_2$-$C_4$-hydroxyalkyl group and the ring being optionally substituted with halogen, $C_1$-$C_3$-alkyl, $C_1$-$C_4$-haloalkyl or $NR^8R^9$;
and stereoisomers, tautomers, N-oxides, hydrates, solvates, and salts thereof, and mixtures of same.

In a further embodiment of the first aspect, the present invention covers compounds of formula (I), supra, in which:
$R^6$, $R^7$ represent, independently from each other, hydrogen, methyl or 6-membered nitrogen containing heterocyclic ring, which ring is attached to a carbon atom and optionally substituted with ethyl or 2,2,2-trifluoroethyl;
and stereoisomers, tautomers, N-oxides, hydrates, solvates, and salts thereof, and mixtures of same.

In a further embodiment of the first aspect, the present invention covers compounds of formula (I), supra, in which:
$R^8$, $R^9$ represent, independently from each other, hydrogen, $C_1$-$C_4$-alkyl, $C_1$-$C_4$-haloalkyl;
and stereoisomers, tautomers, N-oxides, hydrates, solvates, and salts thereof, and mixtures of same.

In a further embodiment of the first aspect, the present invention covers compounds of formula (I), supra, in which:
$R^8$, $R^9$ represent, independently from each other, hydrogen, $C_1$-$C_3$-alkyl, $C_1$-$C_3$-haloalkyl;
and stereoisomers, tautomers, N-oxides, hydrates, solvates, and salts thereof, and mixtures of same.

In a particular further embodiment of the first aspect, the present invention covers combinations of two or more of the above mentioned embodiments under the heading "further embodiments of the first aspect of the present invention".

The present invention covers any sub-combination within any embodiment or aspect of the present invention of compounds of general formula (I), supra.

The present invention covers any sub-combination within any embodiment or aspect of the present invention of intermediate compounds of general formula (V), (VIII) and (XIII). The present invention covers the compounds of general formula (I) which are disclosed in the Example Section of this text, infra.

The compounds according to the invention of general formula (I) can be prepared according to the following schemes 1 and 2. The schemes and procedures described below illustrate synthetic routes to the compounds of general formula (I) of the invention and are not intended to be limiting. It is clear to the person skilled in the art that the order of transformations as exemplified in schemes 1 and 2 can be modified in various ways. The order of transformations exemplified in these schemes is therefore not intended to be limiting. In addition, interconversion of any of the substituents can be achieved before and/or after the exemplified transformations. These modifications can be such as the introduction of protecting groups, cleavage of protecting groups, reduction or oxidation of functional groups, halogenation, alkylation, acylation, metallation or substitution known to the person skilled in the art. These transformations include those which introduce a functionality which allows for further interconversion of substituents. Appropriate protecting groups and their introduction and cleavage are well-known to the person skilled in the art. Specific examples are described in the subsequent paragraphs.

General Synthetic Routes

Scheme 1: Route 1

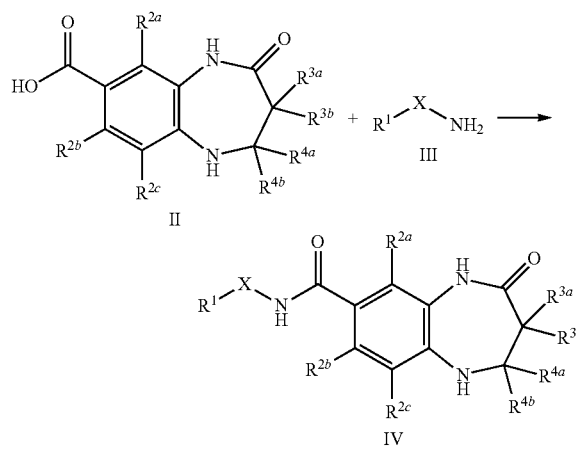

4-oxo-2,3,4,5-tetrahydro-1H-1,5-benzodiazepine-7-carboxylic acids (II) are synthesized in analogy to the procedure outlined by Wu et al (Bioorganic & Medicinal Chemistry Letters, 2002, Pages 959-962). The carboxylic acids (II) are converted to 4-oxo-2,3,4,5-tetrahydro-1H-1,5-benzodiazepine-7-carboxylic amides (IV) using the appropriate amine (III) and amide coupling reagents known to the person skilled in the art, such as but not limited to, T3P, HATU, or CDI, or via activation of the carboxylic acid to the acid chloride.

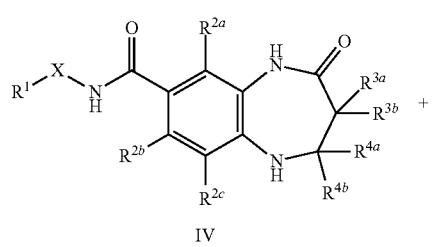

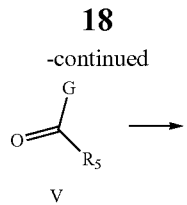

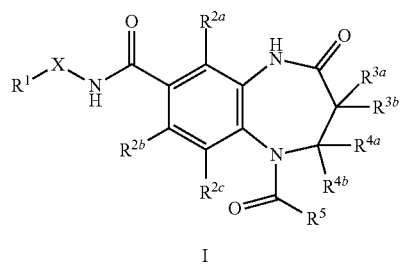

Compounds of the general formula (I) are synthesized by treating the amides (IV) with an appropriate acid chloride (V, G=Cl, $R^5$=phenyl, heteroaryl) or a carbamoyl chloride (V, G=Cl, $R^5$=$NR^6R^7$) in the presence of a base, such as pyridine. Alternatively the appropriate acid chloride is activated in situ from the corresponding acid (V, G=OH) by treatment with oxalyl chloride or 1-chloro-1-dimethylamino-2-methyl-1-propene prior to reacting them with amides (IV). Carbamoyl chlorides are generated in situ from the appropriate amine and an activating agent, such as phosgene.

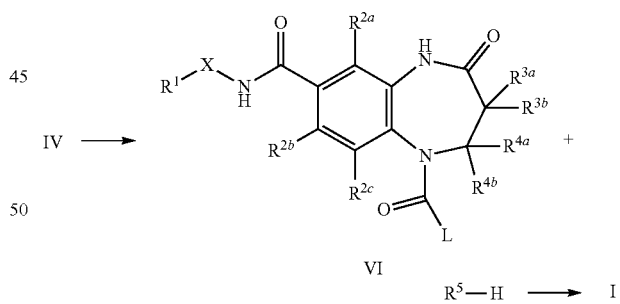

Alternatively, amides (IV) are activated to yield intermediates (VI, L=Cl or p-$NO_2$-phenoxide) using reagents, such as triphosgene or nitrophenyl chloroformate, in the presence of a base, such as N,N-diisopropylethylamine. It may be advantageous to isolate and purify these intermediates using isolation techniques known to the person skilled in the art.

It may be advantageous to synthesize the amides (IV) using a modified version of route 1 shown below.

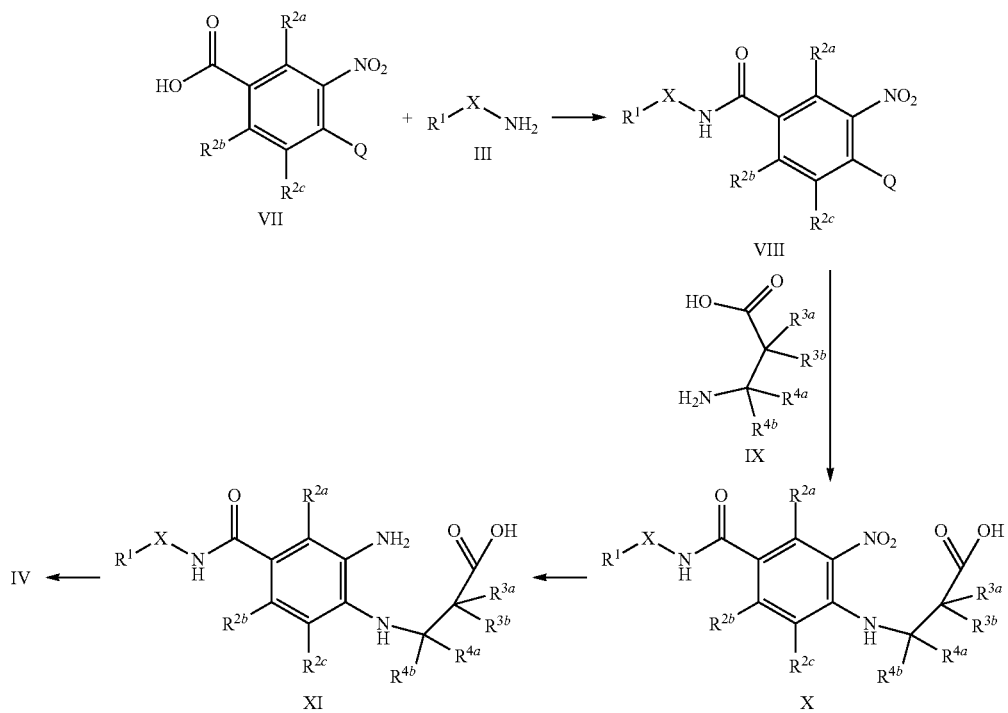

Nitro-carboxylic acids (VII, typically derived from nitration of the des-nitro carboxylic acids using standard nitration conditions) are reacted with amines (III) under standard amid coupling conditions outlined above to yield nitro-amides (VIII). Nitro-carboxylic acids containing a leaving group Q, where Q is preferably a fluoro atom, are treated with β-amino acids in the presence of a base, such as potassium carbonate, to yield nitro-compounds (X). Nitro-compounds (X) are reduced to the corresponding diamine (XI) using reducing conditions, such as palladium on carbon under an atmosphere of hydrogen. Diamines (XI) are cyclized using standard amide coupling reagents, such as T3P, to yield amides (IV).

Scheme 2: Route 2

Alternatively, compounds of general formula (I) are synthesized using synthetic route 2 outlined below.

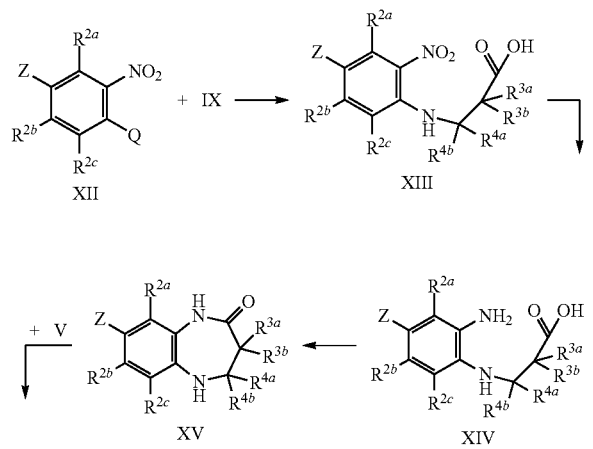

-continued

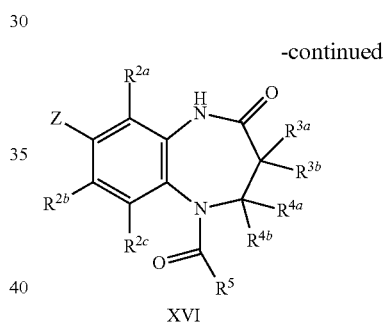

Nitro-compounds (XII), wherein Q is a leaving group, preferably a fluoro atom, and Z is a carboxylic acid precursor, such as an alkyl ester or a cyano group, are synthesized by nitration of the des-nitro compounds using standard nitration conditions or esterification of nitro acids (VII). These nitro-compounds (XII) are treated with β-amino acids in the presence of a base, such as potassium carbonate, to yield nitro-compounds (XIII). Nitro-compounds (XIII) are reduced to the corresponding diamines (XIV) using reducing conditions, such as palladium on carbon under an atmosphere of hydrogen. Diamines (XIV) are cyclized using standard amide coupling reagents, such as T3P, to yield 4-oxo-2,3,4,5-tetrahydro-1H-1,5-benzodiazepines of general formula (XV).

Compounds of general formula (XV) are acylated with an appropriate acid chloride (V, G=Cl, $R^5$=phenyl, heteroaryl) or a carbamoyl chloride (V, G=Cl, $R^5$=$NR^6R^7$) in the presence of a base, such as pyridine, to yield compounds of general formula (XVI). Alternatively the appropriate acid chloride is activated in situ from the corresponding acid (V, G=OH) by treatment with oxalyl chloride or 1-chloro-1-dimethylamino-2-methyl-1-propene prior to reaction with compounds of general formula (XV).

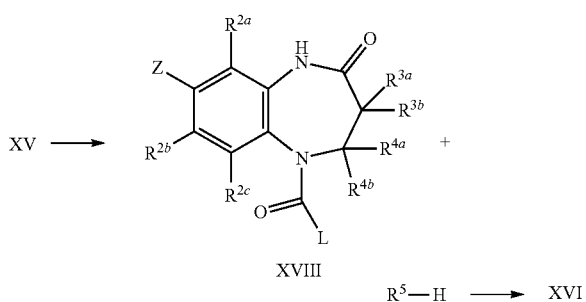

Alternatively, compounds of general formula (XV) are activated to yield intermediates (XVIII, L=Cl or p-NO$_2$-phenoxide) using reagents, such as triphosgene or nitrophenyl chloroformate, in the presence of a base, such as N,N-diisopropylethylamine. It may be advantageous to isolate and purify these intermediates using isolation techniques known to the person skilled in the art.

Acid precursors (XVI) are reacted under standard conditions known to a person skilled in the art to yield acids (XVII). For example, esters (XVI, Z=alkyl ester) are hydrolyzed using aqueous base, such as lithium hydroxide, to yield acids (XVII).

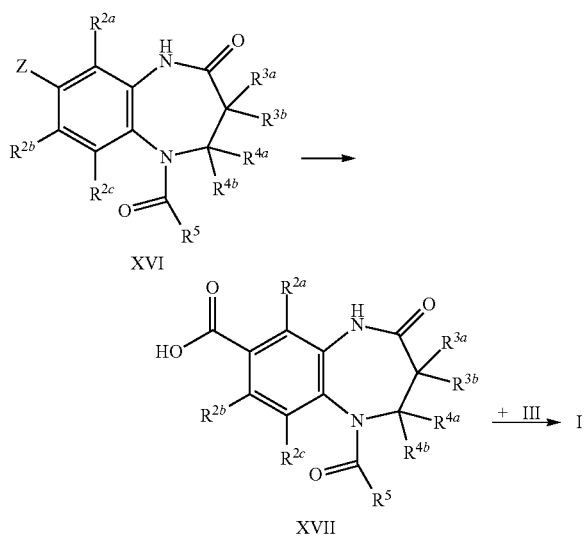

Acids (XVII) are then treated with amines (III) under conditions described above to yield compounds of general formula (I).

The compounds are either commercially available or can be prepared according to procedures available from the public domain, as understandable to the person skilled in the art. Specific examples are described in the Experimental Section.

The present invention covers methods of preparing compounds of the present invention of general formula (I), said methods comprising the steps as described in the Experimental Section herein.

The present invention covers the intermediate compounds which are disclosed in the Example Section of this text, infra.

The present invention covers any sub-combination within any embodiment or aspect of the present invention of intermediate compounds of general formula (V), (VIII) and (XIII), supra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Compounds of the present invention can be utilized to inhibit the interaction between menin and MLL-1 and decrease cell proliferation and/or cell division, and/or produce apoptosis. This method comprises administering to a mammal in need thereof, including a human, an amount of a compound of general formula (I) of the present invention, or a pharmaceutically acceptable salt, isomer, polymorph, metabolite, hydrate, solvate or ester thereof, which is effective to treat the disorder.

Hyperproliferative disorders include, but are not limited to, for example: psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancers include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, medulloblastoma, ependymoma, as well as neuroectodermal and pineal tumour.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Tumours of the digestive tract include, but are not limited to, anal, colon, colorectal, oesophageal, gallbladder, gastric, pancreatic, rectal, small-intestine, and salivary gland cancers.

Tumours of the urinary tract include, but are not limited to, bladder, penile, kidney, renal pelvis, ureter, urethral and human papillary renal cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, oropharyngeal cancer, lip and oral cavity cancer and squamous cell.

Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute myeloid leukemia, acute lymphoblastic leukemia, chronic lymphocytic leukemia, chronic myelogenous leukemia, and hairy cell leukemia.

The present invention also provides methods of treating angiogenic disorders including diseases associated with excessive and/or abnormal angiogenesis.

Inappropriate and ectopic expression of angiogenesis can be deleterious to an organism. A number of pathological conditions are associated with the growth of extraneous blood vessels. These include, for example, diabetic retinopathy, ischemic retinal-vein occlusion, and retinopathy of prematurity [Aiello et al., New Engl. J. Med., 1994, 331, 1480; Peer et al., Lab. Invest., 1995, 72, 638], age-related macular degeneration (AMD) [Lopez et al., Invest. Opthhalmol. Vis. Sci., 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of general formula (I) of the present invention can be utilized to treat and/or prevent any of the aforementioned angiogenesis disorders, for example by inhibiting and/or reducing blood vessel formation; by inhibiting, blocking, reducing, decreasing, etc. endothelial cell proliferation, or other types involved in angiogenesis, as well as causing cell death or apoptosis of such cell types.

These disorders have been well characterized in humans, but also exist with a similar etiology in other mammals, and can be treated by administering pharmaceutical compositions of the present invention.

The term "treating" or "treatment" as stated throughout this document is used conventionally, for example the management or care of a subject for the purpose of combating, alleviating, reducing, relieving, improving the condition of a disease or disorder, such as a carcinoma.

The compounds of the present invention can be used in particular in therapy and prevention, i.e. prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention will serve to:

1. yield better efficacy in reducing the growth of a tumour or even eliminate the tumour as compared to administration of either agent alone,
2. provide for the administration of lesser amounts of the administered chemotherapeutic agents,
3. provide for a chemotherapeutic treatment that is well tolerated in the patient with fewer deleterious pharmacological complications than observed with single agent chemotherapies and certain other combined therapies,
4. provide for treating a broader spectrum of different cancer types in mammals, especially humans,
5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other cancer agent combinations produce antagonistic effects.

In addition, the compounds of general formula (I) of the present invention can also be used in combination with radiotherapy and/or surgical intervention.

In a further embodiment of the present invention, the compounds of general formula (I) of the present invention may be used to sensitize a cell to radiation, i.e. treatment of a cell with a compound of the present invention prior to radiation treatment of the cell renders the cell more susceptible to DNA damage and cell death than the cell would be in the absence of any treatment with a compound of the present invention. In one aspect, the cell is treated with at least one compound of general formula (I) of the present invention.

Thus, the present invention also provides a method of killing a cell, wherein a cell is administered one or more compounds of the present invention in combination with conventional radiation therapy.

The present invention also provides a method of rendering a cell more susceptible to cell death, wherein the cell is treated with one or more compounds of general formula (I) of the present invention prior to the treatment of the cell to cause or induce cell death. In one aspect, after the cell is treated with one or more compounds of general formula (I) of the present invention, the cell is treated with at least one compound, or at least one method, or a combination thereof, in order to cause DNA damage for the purpose of inhibiting the function of the normal cell or killing the cell.

In other embodiments of the present invention, a cell is killed by treating the cell with at least one DNA damaging agent, i.e. after treating a cell with one or more compounds of general formula (I) of the present invention to sensitize the cell to cell death, the cell is treated with at least one DNA damaging agent to kill the cell. DNA damaging agents useful in the present invention include, but are not limited to, chemotherapeutic agents (e.g. cis platin), ionizing radiation (X-rays, ultraviolet radiation), carcinogenic agents, and mutagenic agents.

In other embodiments, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of general formula (I) of the present invention is administered to a cell prior to the radiation or other induction of DNA damage in the cell. In another aspect of the invention, a compound of general formula (I) of the present invention is administered to a cell concomitantly with the radiation or other induction of DNA damage in the cell. In yet another aspect of the invention, a compound of general formula (I) of the present invention is administered to a cell immediately after radiation or other induction of DNA damage in the cell has begun.

In another aspect, the cell is in vitro. In another embodiment, the cell is in vivo.

Compounds of the present invention can be utilized to inhibit the interaction between menin and MLL-1. This method comprises administering to a mammal in need thereof, including a human, an amount of a compound of this invention, or a pharmaceutically acceptable salt, isomer, polymorph, metabolite, hydrate, solvate or ester thereof; which is effective to treat the disorder.

These disorders have been well characterized in humans, but also exist with a similar etiology in other mammals, and can be treated by administering pharmaceutical compositions of the present invention.

The term "treating" or "treatment" as used in the present text is used conventionally, e.g., the management or care of a subject for the purpose of combating, alleviating, reducing, relieving, improving the condition of a disease or disorder, such as a carcinoma.

The compounds of the present invention can be used in particular in therapy and prevention, i.e. prophylaxis, of cancer.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prophylaxis of diseases, in particular cancer.

The pharmaceutical activity of the compounds according to the invention can be explained by their activity as inhibitors of the interaction between menin and MLL-1.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, for the treatment or prophylaxis of diseases, in particular cancer, particularly acute myeloid leukemia, prostate and breast carcinoma, and hepatocellular carcinoma.

In accordance with a further aspect, the present invention covers the use of a compound of formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of diseases, in particular cancer, particularly acute myeloid leukemia, prostate and breast carcinoma, and hepatocellular carcinoma.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prophylaxis of diseases, in particular cancer, particularly acute myeloid leukemia, prostate and breast carcinoma, and hepatocellular carcinoma.

In accordance with a further aspect, the present invention covers use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular cancer disorders, particularly acute myeloid leukemia, prostate and breast carcinoma, and hepatocellular carcinoma.

In accordance with a further aspect, the present invention covers a method of treatment or prophylaxis of diseases, in particular cancer disorders, particularly acute myeloid leukemia, prostate and breast carcinoma, and hepatocellular carcinoma, using an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers pharmaceutical compositions, in particular a medicament, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore covers pharmaceutical compositions, in particular medicaments, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropyl-cellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropyl-methylcellulose phthalate, cellulose acetate, cellulose acetate phthalate, polyacrylates, polymethacrylates such as, for example, Eudragit®)), capsule materials (for example gelatine, hydroxypropyl-methylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention covers pharmaceutical combinations, in particular medicaments, comprising at least one compound of general formula (I) of the present invention and at least one or more further active ingredients, in particular for the treatment and/or prophylaxis of cancer, more specifically acute myeloid leukemia, prostate and breast carcinoma, and hepatocellular carcinoma.

Particularly, the present invention covers a pharmaceutical combination, which comprises:

one or more first active ingredients, in particular compounds of general formula (I) as defined supra, and one or more further active ingredients, in particular cancer, more specifically acute myeloid leukemia, prostate and breast carcinoma, and hepatocellular carcinoma.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with known cancer agents.

Examples of cancer agents include:

131I-chTNT, abarelix, abiraterone, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, atezolizumab, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumab, pentetreotide, nilotinib, nilutamide, nimorazole, nimotuzumab, nimustine, nintedanib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, roniciclib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Based upon standard laboratory techniques known to evaluate compounds useful for the treatment of cancer, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

The $^1$H-NMR data of the examples are listed in the form of $^1$H-NMR peaklists. For each signal peak the δ value in ppm is given, followed by the signal intensity, reported in round brackets. The δ value-signal intensity pairs from different peaks are separated by commas. Therefore, a peaklist is described by the general form: $δ_1$ (intensity$_1$), $δ_2$ (intensity$_2$), . . . , $δ_i$ (intensity$_i$), . . . , $δ_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of target compounds (also the subject of the invention), and/or peaks of impurities. The peaks of stereoisomers, and/or peaks of impurities are typically displayed with a lower intensity compared to the peaks of the target compounds (e.g., with a purity of >90%). Such stereoisomers and/or impurities may be typical for the particular manufacturing process, and therefore their peaks may help to identify the reproduction of our manufacturing process on the basis of "by-product fingerprints". An expert who calculates the peaks of the target compounds by known methods (MestReC, ACD simulation, or by use of empirically evaluated expectation values), can isolate the peaks of target compounds as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. Research Disclosure Database Number 605005, 2014, 1 Aug. 2014, or http://www.researchdisclosure.com/searching-disclosures). In the peak picking routine, as described in the Research Disclosure Database Number 605005, the parameter "MinimumHeight" can be adjusted between 1% and 4%. Depending on the chemical structure and/or depending on the concentration of the measured compound it may be reasonable to set the parameter "MinimumHeight"<1%.

Chemical names were generated using the ACD/Name software from ACD/Labs. In some cases generally accepted names of commercially available reagents were used in place of ACD/Name generated names.

The following table 1 lists the abbreviations used in this paragraph and in the Examples section as far as they are not explained within the text body. Other abbreviations have their meanings customary per se to the skilled person.

TABLE 1

Abbreviations
The following table lists the abbreviations used herein.

| Abbreviation | Meaning |
| --- | --- |
| Boc | tert-butoxycarbonyl |
| c | Concentration |
| DAD | diode array detector |
| DBU | 1,8-diazabicyclo(5.4.0)undec-7-ene |
| DIPEA | Diisopropylethylamine |
| DMF | N,N-dimethylformamide |
| DMSO | Dimethylsulfoxide |
| ELSD | Evaporative Light Scattering Detector |
| ent | Enantiomer |
| ESI | electrospray (ES) ionisation |
| h | hour(s) |
| HPLC | high performance liquid chromatography |
| LC-MS | liquid chromatography mass spectrometry |
| min | minute(s) |
| M | Molar |
| MS | mass spectrometry |
| NMP | 1-methylpyrrolidin-2-one |
| NMR | nuclear magnetic resonance spectroscopy: chemical shifts (δ) are given in ppm. The chemical shifts were corrected by setting the DMSO signal to 2.50 ppm unless otherwise stated. |
| PDA | Photo Diode Array |
| Pd/C | palladium on activated charcoal |
| prep. | Preparative |
| PyBOP | (benzotriazol-1-yloxy)tripyrrolidinophosphonium hexafluorophosphate |
| r.t. or rt or RT | room temperature |
| Rt | retention time (as measured either with HPLC or UPLC) in minutes |
| SQD | Single-Quadrupole-Detector |
| T3P | Propylphosphonic anhydride |
| THF | Tetrahydrofuran |
| UPLC | ultra performance liquid chromatography |

Other abbreviations have their meanings customary per se to the skilled person.

The various aspects of the invention described in this application are illustrated by the following examples which are not meant to limit the invention in any way.

The example testing experiments described herein serve to illustrate the present invention and the invention is not limited to the examples given.

EXPERIMENTAL SECTION—GENERAL PART

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

Analytical LC-MS methods:

Analytical UPLC-MS was performed as described below. The masses (m/z) are reported from the positive mode electrospray ionisation unless the negative mode is indicated (ESI−). In most of the cases method 1 is used. If not, it is indicated.

Method A (HPLC-MS):
Instrument: Waters Acquity UPLCMS SingleQuad; Column: Acquity UPLC BEH C18 1.7 µm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Method B (HPLC-MS):
Instrument: Waters Acquity UPLCMS SingleQuad; Column: XBridge BEH C18 2.5 µm, 50×2.1 mm; eluent A: 10 mM aqueous ammonium bicarbonate solution (pH10), eluent B: acetonitrile; gradient: 0-0.8 min 2-98% B, 0.8-1.3 min 98% B; flow 0.8 ml/min; temperature not controlled.

Method C (HPLC-MS):
Instrument: Waters Acquity UPLCMS SingleQuad; Column: XBridge BEH C18 2.5 µm, 50×2.1 mm; eluent A: 10 mM aqueous ammonium bicarbonate solution (pH10), eluent B: acetonitrile; gradient: 0-4 min 2-98% B, 4.0-4.7 min 98% B; flow 0.8 ml/min; temperature not controlled.

EXPERIMENTAL SECTION—INTERMEDIATES

Intermediate 1

N-(2-cyclopropylethyl)-2-methyl-4-oxo-2,3,4,5-tetrahydro-1H-1,5-benzodiazepine-7-carboxamide (racemic)

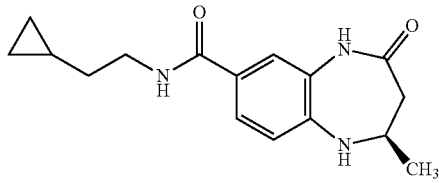 [SMILES: C[C@@H]1CC(=O)Nc2cc(C(=O)NCCC3CC3)ccc2N1]

Commercially available 2-methyl-4-oxo-2,3,4,5-tetrahydro-1H-1,5-benzodiazepine-7-carboxylic acid (500 mg, 2.27 mmol) was dissolved in DMF (8.0 ml), N,N-diisopropylethylamine (1.6 ml, 9.1 mmol) and 2-cyclopropylethanamine (260 µl, 2.7 mmol) were added, followed by T3P (Propylphosphonic anhydride solution, ~50% in DMF, 1.6 ml, 2.7 mmol). The mixture was stirred at room temperature overnight. LCMS indicated complete conversion. The reaction mixture was concentrated and purified using preparative HPLC (water/acetonitrile gradient) to yield the desired intermediate 430 mg (98% purity, 65% yield).

LC-MS (Method A): $R_t$=0.84 min; MS (ESIpos): m/z=288 [M+H]$^+$ $^1$H-NMR (400 MHz, DMSO-d6) δ[ppm]: 0.000 (2.09), 0.010 (7.25), 0.014 (7.40), 0.022 (7.88), 0.026 (7.31), 0.036 (2.80), 0.353 (2.59), 0.363 (6.30), 0.367 (7.10), 0.374 (3.63), 0.378 (3.31), 0.383 (7.46), 0.388 (7.17), 0.398 (2.87), 0.647 (0.80), 0.659 (1.48), 0.666 (1.37), 0.671 (1.22), 0.679 (2.28), 0.687 (1.20), 0.690 (1.31), 0.699 (1.35), 1.180 (15.58), 1.196 (16.00), 1.339 (2.74), 1.356 (6.30), 1.375 (6.37), 1.393 (2.89), 1.887 (0.61), 2.068 (1.48), 2.254 (2.02), 2.273 (2.21), 2.287 (2.93), 2.306 (3.65), 2.315 (1.16), 2.427 (2.80), 2.435 (3.12), 2.461 (2.82), 2.502 (10.25), 2.506 (7.76), 2.648 (0.78), 2.653 (1.10), 2.657 (0.80), 3.221 (2.51), 3.236 (4.70), 3.256 (4.91), 3.271 (2.80), 3.809 (1.24), 3.825 (1.79), 5.890 (3.25), 6.751 (2.00), 6.771 (2.15), 7.324 (2.40), 7.345 (2.53), 7.356 (8.87), 7.361 (6.62), 8.060 (1.62), 8.074 (3.14), 8.088 (1.71), 9.503 (6.77).

Intermediate 2

N-(2-cyclopropylethyl)-2,3-dimethyl-4-oxo-2,3,4,5-tetrahydro-1H-1,5-benzodiazepine-7-carboxamide (mixture of stereoisomers)

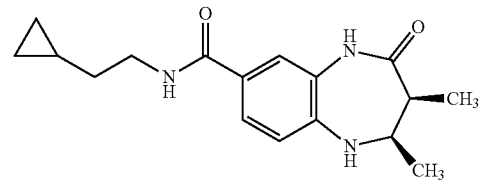 [SMILES: C[C@@H]1C(=O)Nc2cc(C(=O)NCCC3CC3)ccc2N[C@@H]1C]

Was synthesized analogously to Intermediate 1 from commercially available 2,3-dimethyl-4-oxo-2,3,4,5-tetrahydro-1H-1,5-benzodiazepine-7-carboxylic acid and 2-cyclopropylethanamine LC-MS (Method A): $R_t$=0.88 min; MS (ESIpos): m/z=302 [M+H]$^+$ $^1$H-NMR (400 MHz, DMSO-d6) δ[ppm]: 0.000 (1.78), 0.010 (5.99), 0.014 (7.23), 0.023 (6.79), 0.026 (7.32), 0.036 (2.06), 0.353 (2.07), 0.363 (5.47), 0.367 (6.32), 0.373 (3.06), 0.377 (2.86), 0.384 (6.34), 0.387 (6.31), 0.398 (2.11), 0.646 (0.77), 0.658 (1.27), 0.665 (1.31), 0.670 (1.19), 0.678 (2.04), 0.690 (1.20), 0.695 (1.28), 0.936 (14.40), 0.950 (8.55), 0.953 (16.00), 0.966 (4.74), 1.058 (12.97), 1.074 (13.25), 1.128 (4.20), 1.144 (4.14), 1.338 (2.40), 1.356 (5.65), 1.375 (5.76), 1.392 (2.35), 2.069 (2.23), 2.312 (0.64), 2.341 (0.65), 2.359 (0.69), 2.362 (0.74), 2.380 (0.62), 2.654 (0.63), 2.699 (2.23), 2.706 (2.26), 2.716 (2.15), 2.723 (2.22), 3.219 (2.15), 3.226 (1.44), 3.234 (3.98), 3.239 (4.04), 3.255 (4.42), 3.270 (2.21), 3.276 (1.10), 3.657 (1.14), 3.665 (1.17), 3.673 (1.53), 3.679 (1.52), 3.687 (1.17), 3.695 (1.07), 5.699 (1.09), 5.704 (1.07), 6.164 (2.88), 6.178 (2.82), 6.693 (2.78), 6.714 (2.97), 6.780 (0.95), 6.801 (1.00), 7.313 (2.19), 7.318 (2.69), 7.334

(2.70), 7.339 (3.39), 7.347 (7.44), 7.351 (5.27), 7.367 (2.15), 7.372 (1.49), 8.037 (1.43), 8.051 (2.75), 8.065 (1.41), 8.092 (0.87), 9.518 (8.12).

Intermediate 3

(2R)—N-(2-cyclobutylethyl)-2-methyl-4-oxo-2,3,4,5-tetrahydro-1H-1,5-benzodiazepine-7-carboxamide (racemic)

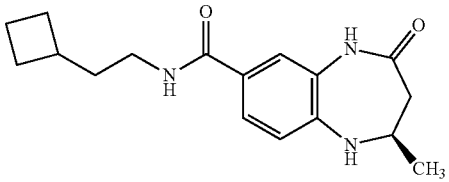 [SMILES: C[C@@H]1CC(=O)Nc2cc(C(=O)NCCC3CCC3)ccc2N1]

Was synthesized analogously to Intermediate 1 from commercially available 2-methyl-4-oxo-2,3,4,5-tetrahydro-1H-1,5-benzodiazepine-7-carboxylic acid and 2-cyclopropylethanamine LC-MS (Method A): $R_t$=0.93 min; MS (ESIpos): m/z=302 [M+H]$^+$ $^1$H-NMR (400 MHz, DMSO-d6) δ[ppm]: 1.196 (15.90), 1.212 (16.00), 1.546 (2.98), 1.565 (8.61), 1.571 (3.38), 1.582 (7.48), 1.593 (4.39), 1.600 (3.48), 1.610 (2.68), 1.616 (3.30), 1.631 (1.00), 1.638 (1.18), 1.747 (1.05), 1.758 (2.52), 1.767 (1.82), 1.779 (4.20), 1.788 (1.82), 1.800 (3.88), 1.805 (1.64), 1.822 (1.87), 1.825 (1.60), 1.843 (0.85), 1.847 (0.80), 1.975 (1.32), 1.981 (1.26), 1.985 (1.42), 1.993 (2.20), 1.995 (2.27), 2.000 (2.74), 2.003 (3.29), 2.009 (2.36), 2.013 (2.74), 2.016 (2.41), 2.024 (3.27), 2.031 (2.14), 2.036 (1.42), 2.043 (1.34), 2.052 (1.10), 2.241 (1.12), 2.260 (2.50), 2.270 (2.31), 2.280 (3.16), 2.289 (2.47), 2.303 (3.49), 2.323 (3.67), 2.327 (1.66), 2.331 (0.88), 2.444 (2.86), 2.451 (3.08), 2.518 (3.01), 2.523 (1.96), 2.665 (0.65), 2.669 (0.89), 2.674 (0.64), 3.086 (2.39), 3.101 (4.67), 3.120 (4.72), 3.136 (2.25), 3.818 (0.80), 3.825 (1.24), 3.833 (1.44), 3.842 (1.71), 3.860 (1.15), 5.897 (3.53), 5.904 (3.49), 6.766 (3.30), 6.787 (3.49), 7.327 (2.62), 7.332 (3.09), 7.348 (2.36), 7.353 (3.13), 7.367 (8.44), 7.372 (6.16), 8.011 (1.72), 8.025 (3.30), 8.039 (1.63), 9.516 (6.59).

Intermediate 4

N-(2-cyclobutylethyl)-2,3-dimethyl-4-oxo-2,3,4,5-tetrahydro-1H-1,5-benzodiazepine-7-carboxamide (mixture of stereoisomers)

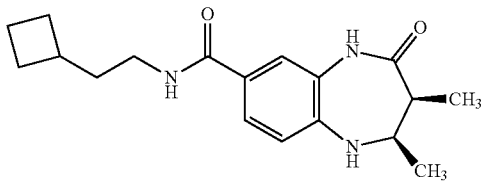 [SMILES: C[C@@H]1C(=O)Nc2cc(C(=O)NCCC3CCC3)ccc2N[C@@H]1C]

Was synthesized analogously to Intermediate 1 from commercially available 2,3-dimethyl-4-oxo-2,3,4,5-tetrahydro-1H-1,5-benzodiazepine-7-carboxylic acid and 2-cyclobutylethanamine hydrochloride LC-MS (Method A): $R_t$=0.99 min; MS (ESIpos): m/z=316 [M+H]$^+$ $^1$H-NMR (400 MHz, DMSO-d6) δ[ppm]: 0.951 (14.59), 0.965 (9.06), 0.968 (16.00), 0.982 (5.70), 1.073 (12.50), 1.089 (12.49), 1.143 (4.72), 1.159 (4.67), 1.544 (2.71), 1.563 (7.89), 1.580 (6.73), 1.592 (4.64), 1.598 (4.07), 1.615 (3.48), 1.637 (1.28), 1.729 (0.67), 1.746 (1.10), 1.756 (2.60), 1.766 (1.97), 1.777 (4.39), 1.787 (1.92), 1.799 (3.95), 1.820 (1.99), 1.842 (0.83), 1.846 (0.83), 1.973 (1.27), 1.979 (1.24), 1.984 (1.55), 1.994 (2.46), 2.002 (3.37), 2.009 (2.61), 2.012 (2.87), 2.015 (2.65), 2.023 (3.35), 2.032 (2.14), 2.042 (1.28), 2.051 (1.06), 2.238 (0.94), 2.259 (2.11), 2.278 (2.57), 2.298 (1.77), 2.318 (0.91), 2.322 (0.78), 2.327 (0.80), 2.332 (0.61), 2.356 (0.71), 2.373 (0.80), 2.377 (0.80), 2.394 (0.69), 2.518 (3.06), 2.523 (1.77), 2.669 (0.76), 2.713 (2.16), 2.721 (2.19), 2.731 (2.08), 2.738 (2.16), 3.083 (1.92), 3.090 (1.48), 3.098 (4.00), 3.102 (4.08), 3.117 (4.27), 3.132 (2.05), 3.691 (1.37), 5.713 (0.82), 6.178 (1.63), 6.191 (1.65), 6.708 (2.20), 6.729 (2.34), 6.796 (0.88), 6.816 (0.95), 7.320 (1.92), 7.325 (2.31), 7.341 (2.59), 7.345 (2.80), 7.356 (7.36), 7.361 (5.69), 7.377 (2.49), 7.381 (1.90), 7.988 (1.31), 8.002 (2.54), 8.015 (1.36), 8.042 (0.98), 9.529 (8.33).

Intermediate 5

N-(2-cyclopropylethyl)-4-fluoro-3-nitrobenzamide

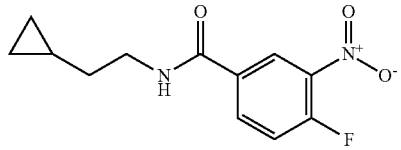 [SMILES: O=C(NCCC1CC1)c1ccc(F)c([N+](=O)[O-])c1]

Propanephosphonic anhydride (T3P, 50% in EtOAc, 44 ml, 74 mmol) was added to a stirred solution of 4-fluoro-3-nitrobenzoic acid (7.53 g, 40.7 mmol), 2-cyclopropylethanamine hydrochloride (1:1) (4.50 g, 37.0 mmol) and N,N-diisopropylethylamine (13 ml, 74 mmol) in EtOAc (20 mL) cooled to 0° C. The orange solution was stirred at room temperature for 36 h. The reaction mixture quenched with saturated sodium bicarbonate solution and the layers were separated. The aqueous layer was washed with ethyl acetate, the combined organic layers were washed with brine, dried over sodium sulfate and concentrated to a yellow solid, 6.77 g (66%).

UPLC (Method B) 0.75 min, 99% purity, (M+H)+ 253.

$^1$H NMR (400 MHz, DMSO-d6) δ=8.81 (t, J=1.0 Hz, 1H), 8.59 (dd, J=2.3, 7.3 Hz, 1H), 8.23 (ddd, J=2.3, 4.6, 8.7 Hz, 1H), 7.68 (dd, J=8.7, 11.0 Hz, 1H), 3.39-3.23 (m, 2H), 1.40 (q, J=6.9 Hz, 2H), 0.77-0.63 (m, 1H), 0.42-0.29 (m, 2H), 0.07-0.04 (m, 2H)

Intermediate 6

(3S)-3-({4[(2-cyclopropylethyl)carbamoyl]-2-nitrophenyl}amino)butanoic acid

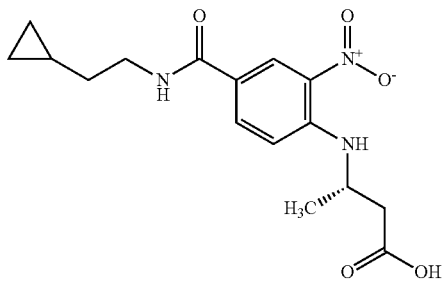 [SMILES: C[C@@H](CC(=O)O)Nc1ccc(C(=O)NCCC2CC2)cc1[N+](=O)[O-]]

A mixture of N-(2-cyclopropylethyl)-4-fluoro-3-nitrobenzamide (Intermediate 5, 6.77 g, 26.8 mmol), (3S)-3-aminobutanoic acid (3.04 g, 29.5 mmol) and sodium carbonate (5.69 g, 53.7 mmol) in EtOH (60 ml) and water (60 ml) was heated at 70° C. for 2 hours. The reaction mixture was cooled to room temperature and partitioned between water and ethyl acetate. The aqueous layer was separated and was acidified to pH 1 with hydrochloric acid (2 M). The aqueous phase was extracted with ethyl acetate twice. The combined ethyl acetate washes were washed with brine, dried over sodium sulfate and concentrated to an orange oil, 8.71 g (97%).

UPLC (Method B) 0.51 min, 98% purity, (M+H)+ 336.

1H NMR (400 MHz, DMSO): −0.01-0.03 (m, 2H), 0.34-0.38 (m, 2H), 0.62-0.71 (m, 1H), 1.25 (d, 3H), 1.37 (quartet, 2H), 2.56-2.66 (m, 2H), 3.27 (quartet, 2H), 4.16-4.23 (m, 1H), 7.96 (dd, 1H), 8.39 (d, 1H), 8.49 (t, 1H), 8.60 (d, 1H), 12.42 (br s, 1H) plus EtOAc.

Intermediate 7

(3S)-3-({2-amino-4-[(2-cyclopropylethyl)carbamoyl]phenyl}amino)butanoic acid

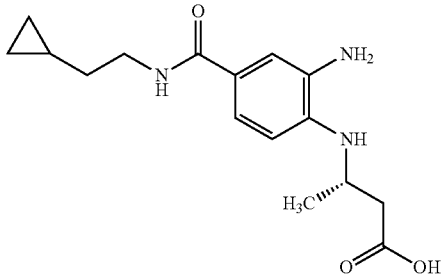 [SMILES: C[C@@H](CC(=O)O)Nc1ccc(C(=O)NCCC2CC2)cc1N]

A suspension of 5% Pd/C and (3S)-3-({4-[(2-cyclopropylethyl)carbamoyl]-2-nitrophenyl}amino)butanoic acid (Intermediate 6, 6.10 g, 18.2 mmol) in ethyl acetate (250 mL) was stirred under an atmosphere of hydrogen gas overnight. LCMS showed complete conversion. The suspension was filtered through celite, the filter cake was washed with ethyl acetate and acetonitrile. The filtrate was concentrated to a dark yellow oil (6.05 g, >100% yield, likely to still have solvent present) which was taken on to the next reaction without purification. UPLC (Method B) 0.46 min, 82% purity, (M+H)+ 306.

Intermediate 8

(2S)—N-(2-cyclopropylethyl)-2-methyl-4-oxo-2,3,4,5-tetrahydro-1H-1,5-benzodiazepine-7-carboxamide

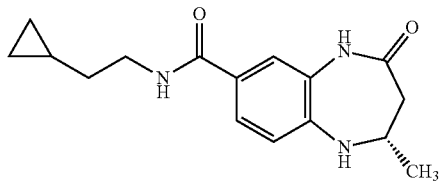 [SMILES: C[C@H]1CC(=O)Nc2cc(C(=O)NCCC3CC3)ccc2N1]

(3S)-3-({2-amino-4-[(2-cyclopropylethyl)carbamoyl]phenyl}amino)butanoic acid (Intermediate 7, 5.55 g, 18.2 mmol) in acetonitrile (300 mL) was cooled on an ice bath, N,N-diisopropylethylamine (7.0 ml, 40 mmol) and Propanephosphonic anhydride (T3P, 50% in EtOAc, 12 ml, 20 mmol) were added and the solution was stirred at room temperature overnight. LCMS showed complete conversion. The reaction mixture was concentrated, the residue taken up in ethyl acetate, and washed with sat sodium bicarbonate solution, then brine, dried over sodium sulfate and concentrated to a yellow solid, 4.28 g (82%).

UPLC 0.57 min, 97% purity, (M+H)+ 288

1H-NMR (400 MHz, DMSO-d6): Shift [ppm]=9.50 (s, 1H), 8.08 (br t, 1H), 7.28-7.38 (m, 1H), 6.74 (d, 1H), 5.82-5.96 (m, 1H), 3.72-3.89 (m, 1H), 3.16-3.29 (m, 2H), 2.36-2.45 (m, 1H), 2.17-2.36 (m, 1H), 1.35 (q, 2H), 1.07-1.24 (m, 3H), 0.57-0.73 (m, 1H), 0.27-0.42 (m, 2H), 0.00 (q, 2H).

EXPERIMENTAL SECTION—EXAMPLES

Example 1

1-benzoyl-N-(2-cyclopropylethyl)-2-methyl-4-oxo-2,3,4,5-tetrahydro-1H-1,5-benzodiazepine-7-carboxamide (racemic)

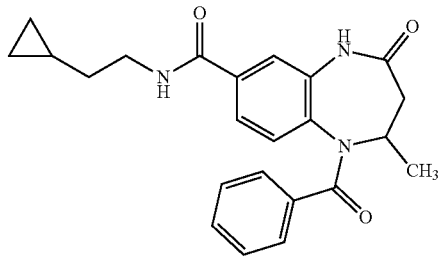 [SMILES: CC1CC(=O)Nc2cc(C(=O)NCCC3CC3)ccc2N1C(=O)c1ccccc1]

N-(2-cyclopropylethyl)-2-methyl-4-oxo-2,3,4,5-tetrahydro-1H-1,5-benzodiazepine-7-carboxamide (Intermediate 1, 100 mg, 348 μmol) was suspended in dichloromethane (4.0 ml). Benzoyl chloride (120 μl, 1.0 mmol), pyridine (170 μl, 2.1 mmol), and 4-dimethylaminopyridine (42.5 mg, 348 μmol) were added to the mixture. The mixture was stirred at room temperature overnight. LCMS indicated complete conversion. The reaction mixture was concentrated and purified using preparative HPLC (water/acetonitrile gradient) to yield the desired product (4.40 mg, 98% purity, 3% yield).

LC-MS (Method A): $R_t$=0.97 min; MS (ESIpos): m/z=392 [M+H]$^+$ $^1$H-NMR (500 MHz, DMSO-d6) δ[ppm]: −0.018 (2.85), −0.007 (9.42), 0.000 (9.86), 0.011 (3.29), 0.339 (3.29), 0.346 (8.55), 0.349 (9.21), 0.354 (4.38), 0.362 (9.42), 0.366 (8.77), 0.373 (3.51), 0.652 (3.07), 1.176 (15.78), 1.188 (16.00), 1.326 (3.73), 1.340 (10.08), 1.355 (9.86), 1.369 (3.73), 2.281 (2.41), 2.307 (5.04), 2.334 (5.70), 2.338 (5.04), 2.342 (3.51), 2.398 (2.63), 2.491 (14.68), 2.495 (11.84), 2.499 (8.55), 2.516 (4.38), 2.608 (3.07), 2.612 (4.38), 2.615 (2.85), 3.212 (2.41), 3.227 (4.82), 3.241 (5.48), 3.252 (5.48), 3.267 (2.63), 3.280 (3.51), 3.285 (3.51), 3.287 (4.60), 3.292 (3.29), 3.297 (5.70), 3.334 (2.41), 3.341 (1.53), 3.345 (1.10), 5.016 (1.75), 6.867 (2.85), 7.053 (6.14), 7.144 (5.70), 7.231 (3.07), 7.302 (2.85), 7.547 (12.71), 7.550 (12.27), 8.453 (4.16), 10.061 (5.48).

Example 2

1-benzoyl-N-(2-cyclopropylethyl)-2,3-dimethyl-4-oxo-2,3,4,5-tetrahydro-1H-1,5-benzodiazepine-7-carboxamide (mixture of stereoisomers)

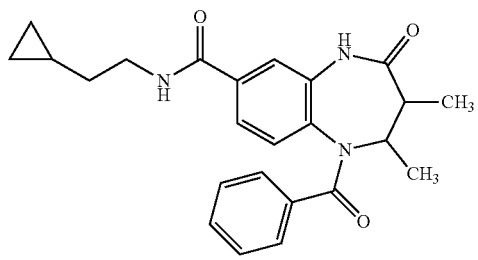 [SMILES: CC1C(=O)Nc2cc(C(=O)NCCC3CC3)ccc2N(C(=O)c2ccccc2)C1C]

Was synthesized analogously to Example 1 from Intermediate 2 and benzoyl chloride.

LC-MS (Method A): $R_t$=1.03 min; MS (ESIpos): m/z=406 [M+H]$^+$ $^1$H-NMR (400 MHz, DMSO-d6): δ [ppm]=9.83 (br s, 1H), 8.01-8.24 (m, 1H), 7.58 (dd, 1H), 7.32-7.40 (m, 1H), 7.08-7.32 (m, 6H), 6.84-6.94 (m, 1H), 6.76 (d, 1H), 4.82 (s, 1H), 4.54-4.69 (m, 1H), 3.22-3.36 (m, 2H), 2.88-2.97 (m, 1H), 2.34-2.41 (m, 1H), 1.35-1.48 (m, 2H), 1.24 (dd, 3H), 1.03-1.13 (m, 1H), 0.97 (d, 2H), 0.64-0.76 (m, 1H), 0.36-0.44 (m, 2H), −0.01-0.09 (m, 2H).

Example 3

1-benzoyl-N-(2-cyclobutylethyl)-2-methyl-4-oxo-2,3,4,5-tetrahydro-1H-1,5-benzodiazepine-7-carboxamide (racemic)

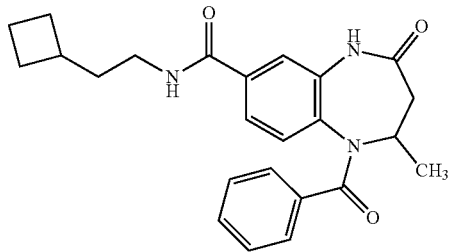 [SMILES: CC1CC(=O)Nc2cc(C(=O)NCCC3CCC3)ccc2N1C(=O)c1ccccc1]

Was synthesized analogously to Example 1 from Intermediate 3 and benzoyl chloride.

LC-MS (Method A): $R_t$=1.07 min; MS (ESIpos): m/z=406 [M+H]$^+$ $^1$H-NMR (400 MHz, DMSO-d6) δ[ppm]: 1.197 (16.00), 1.213 (16.00), 1.534 (3.65), 1.552 (12.02), 1.570 (14.71), 1.589 (6.06), 1.597 (4.95), 1.620 (1.62), 1.720 (0.74), 1.737 (1.48), 1.748 (3.33), 1.758 (2.64), 1.769 (5.60), 1.779 (2.59), 1.791 (5.27), 1.812 (2.82), 1.834 (1.11), 1.839 (1.20), 1.956 (1.66), 1.962 (1.71), 1.967 (1.90), 1.977 (3.24), 1.985 (4.53), 1.995 (3.93), 2.005 (4.44), 2.014 (3.05), 2.024 (1.85), 2.034 (1.43), 2.084 (8.51), 2.216 (1.39), 2.236 (3.10), 2.255 (3.70), 2.274 (2.59), 2.297 (2.50), 2.330 (5.55), 2.363 (3.24), 2.408 (2.31), 2.422 (2.64), 2.442 (1.71), 2.457 (1.62), 2.523 (3.65), 2.665 (0.97), 2.669 (1.25), 2.674 (0.88), 3.062 (0.74), 3.077 (1.90), 3.094 (4.35), 3.109 (6.01), 3.124 (4.44), 3.141 (1.99), 3.157 (0.79), 3.297 (0.69), 3.372 (0.97), 3.376 (0.83), 5.038 (1.57), 6.872 (2.68), 6.892 (2.87), 7.062 (4.90), 7.080 (6.75), 7.150 (3.42), 7.169 (6.01), 7.188 (3.56), 7.239 (2.68), 7.257 (3.24), 7.314 (2.96), 7.333 (2.73), 7.564 (10.87), 7.569 (10.73), 8.399 (2.31), 8.412 (4.25), 8.425 (2.22), 10.082 (6.15).

Example 4

1-benzoyl-N-(2-cyclobutylethyl)-2,3-dimethyl-4-oxo-2,3,4,5-tetrahydro-1H-1,5-benzodiazepine-7-carboxamide (mixture of stereoisomers)

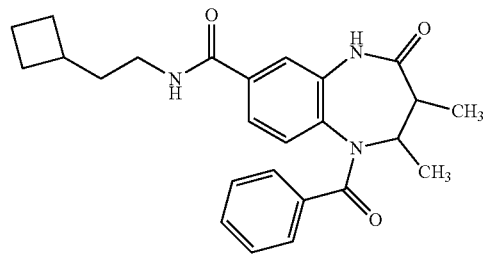 [SMILES: CC1C(=O)Nc2cc(C(=O)NCCC3CCC3)ccc2N(C(=O)c2ccccc2)C1C]

Was synthesized analogously to Example 1 from Intermediate 4 and benzoyl chloride.

LC-MS (Method A): $R_t$=1.13 min; MS (ESIpos): m/z=420 [M+H]$^+$ $^1$H-NMR (400 MHz, DMSO-d6) δ[ppm]: 0.969 (2.24), 0.986 (2.01), 1.054 (8.29), 1.070 (8.40), 1.120 (1.73), 1.137 (3.05), 1.228 (16.00), 1.243 (15.65), 1.383 (0.58), 1.417 (2.88), 1.534 (2.88), 1.552 (9.04), 1.571 (11.51), 1.589 (5.93), 1.599 (4.78), 1.618 (3.05), 1.635 (1.78), 1.729 (0.81), 1.748 (2.88), 1.758 (2.53), 1.769 (4.89), 1.779 (2.65), 1.791 (4.78), 1.812 (2.71), 1.834 (1.27), 1.838 (1.27), 1.905 (0.81), 1.916 (0.81), 1.920 (0.81), 1.956 (1.44), 1.963 (1.38), 1.967 (1.55), 1.977 (2.65), 1.985 (3.86), 1.995 (3.57), 1.998 (3.34), 2.005 (4.09), 2.014 (3.22), 2.024 (2.47), 2.034 (2.01), 2.080 (1.15), 2.085 (12.78), 2.115 (4.78), 2.161 (1.04), 2.216 (1.09), 2.236 (2.30), 2.255 (2.82), 2.275 (2.19), 2.296 (1.21), 2.318 (1.73), 2.323 (3.11), 2.327 (4.66), 2.337 (1.67), 2.346 (2.71), 2.359 (2.71), 2.375 (2.36), 2.415 (0.86), 2.518 (12.09), 2.523 (8.06), 2.660 (1.27), 2.665 (2.65), 2.669 (3.63), 2.674 (2.53), 2.678 (1.21), 3.080 (1.73), 3.098 (3.74), 3.106 (3.68), 3.112 (3.57), 3.121 (3.74), 3.138 (1.78), 3.174 (1.09), 4.559 (0.69), 4.588 (1.27), 6.882 (2.19), 6.902 (2.36), 7.080 (3.74), 7.099 (5.53), 7.152 (2.88), 7.170 (4.83), 7.189 (3.11), 7.208 (1.04), 7.240 (2.01), 7.257 (2.42), 7.320 (2.19), 7.341 (2.01), 7.369 (0.86), 7.374 (0.86), 7.443 (0.92), 7.462 (0.75), 7.547 (1.21), 7.554 (8.40), 7.558 (8.69), 7.564 (2.13), 7.583 (0.75), 7.618 (1.21), 7.623 (1.09), 7.802 (0.69), 7.807 (0.86), 7.824 (0.75), 7.827 (0.58), 7.972 (0.86), 7.990 (0.69), 8.135 (0.58), 8.141 (0.58), 8.393 (1.78), 8.406 (3.05), 8.421 (1.61), 9.734 (0.81), 10.114 (5.35), 10.131 (0.92).

Example 5

N-(2-cyclopropylethyl)-2-methyl-1-[(3-methyl-1,2-oxazol-4-yl)carbonyl]-4-oxo-2,3,4,5-tetrahydro-1H-1,5-benzodiazepine-7-carboxamide (racemic)

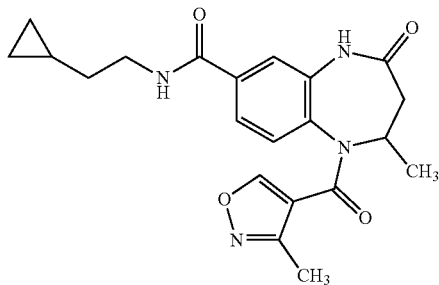 [SMILES: Cc1nocc1C(=O)N1c2ccc(C(=O)NCCC3CC3)cc2NC(=O)CC1C]

Under an atmosphere of argon 3-methyl-4-isoxazolecarboxylic acid (88.5 mg, 696 μmol) was suspended in dichloromethane (1.5 mL), 1-chloro-1-dimethylamino-2-methyl-1-propene (140 μl, 1.0 mmol) was added dropwise. The mixture was stirred at room temperature for 30 minutes after which all solids were dissolved. The mixture was cooled to 0° C. and a mixture of N-(2-cyclopropylethyl)-2-methyl-4-oxo-2,3,4,5-tetrahydro-1H-1,5-benzodiazepine-7-carboxamide (racemic, Intermediate 1) and pyridine (140 μl, 1.7 mmol) in dichloromethane (1.5 mL) was added. The resulting mixture was stirred for 2h at 0° C. uPLC indicated complete conversion. The mixture was concentrated and purified using preparatory HPLC to yield the desired product as white crystals (67.7 mg, 99% purity, 49% yield).

LC-MS (Method A): $R_t$=0.91 min; MS (ESIpos): m/z=397 [M+H]$^+$ $^1$H-NMR (400 MHz, DMSO-d6) δ[ppm]: 0.000 (0.90), 0.010 (2.93), 0.014 (3.06), 0.023 (3.30), 0.026 (2.87), 0.036 (0.99), 0.352 (1.03), 0.361 (2.66), 0.365 (2.78), 0.372 (1.41), 0.375 (1.31), 0.382 (2.93), 0.386 (2.76), 0.396 (0.96), 0.663 (0.66), 0.683 (0.94), 1.155 (6.30), 1.171 (6.28), 1.356 (1.20), 1.374 (3.17), 1.392 (3.13), 1.409 (1.16), 2.212 (16.00), 2.267 (0.66), 2.299 (2.01), 2.331 (1.24), 2.359 (0.92), 2.372 (1.11), 3.255 (0.84), 3.260 (0.92), 3.273 (2.21), 3.279 (2.03), 3.287 (2.33), 3.293 (3.15), 7.215 (1.63), 7.235 (1.84), 7.508 (1.22), 7.529 (1.05), 7.591 (3.62), 7.596 (3.19), 7.677 (1.80), 8.540 (0.84), 8.554 (1.63), 8.568 (0.81), 9.827 (2.03).

Example 6

N-(2-cyclobutylethyl)-2-methyl-1-[(3-methyl-1,2-oxazol-4-yl)carbonyl]-4-oxo-2,3,4,5-tetrahydro-1H-1,5-benzodiazepine-7-carboxamide (racemic)

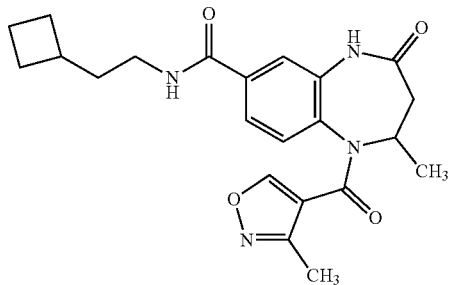 [SMILES: Cc1nocc1C(=O)N1c2ccc(C(=O)NCCC3CCC3)cc2NC(=O)CC1C]

Was synthesized analogously to Example 5 from Intermediate 3.

LC-MS (Method A): $R_t$=1.02 min; MS (ESIpos): m/z=411 [M+H]$^+$ $^1$H-NMR (400 MHz, DMSO-d6) δ[ppm]: 1.182 (6.26), 1.198 (6.22), 1.574 (2.13), 1.580 (1.14), 1.592 (3.73), 1.603 (2.02), 1.610 (3.55), 1.628 (1.99), 1.764 (0.92), 1.773 (0.80), 1.785 (1.65), 1.793 (0.83), 1.808 (1.53), 1.829 (0.80), 1.998 (0.85), 2.000 (0.93), 2.002 (0.96), 2.007 (1.18), 2.010 (1.42), 2.017 (1.02), 2.020 (1.17), 2.024 (1.02), 2.031 (1.37), 2.034 (1.07), 2.038 (0.91), 2.083 (7.09), 2.240 (16.00), 2.274 (1.07), 2.294 (1.83), 2.313 (0.96), 2.326 (2.05), 2.331 (1.08), 2.359 (1.34), 2.385 (0.88), 2.400 (1.08), 3.146 (1.60), 3.153 (1.37), 3.160 (1.37), 3.167 (1.54), 7.240 (1.57), 7.261 (1.77), 7.521 (1.02), 7.525 (1.11), 7.542 (0.93), 7.546 (0.95), 7.612 (3.67), 7.617 (3.20), 7.710 (1.67), 8.501 (0.77), 8.515 (1.53), 8.529 (0.76), 9.851 (1.41).

Example 7

N-(2-cyclopropylethyl)-2,3-dimethyl-1-[(3-methyl-1,2-oxazol-4-yl)carbonyl]-4-oxo-2,3,4,5-tetrahydro-1H-1,5-benzodiazepine-7-carboxamide (mixture of stereoisomers)

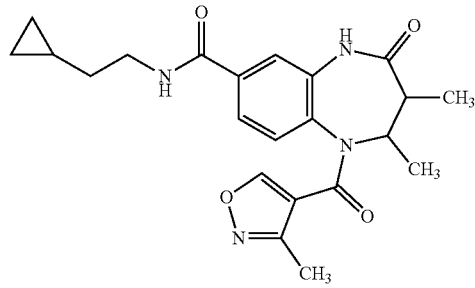 [SMILES: Cc1nocc1C(=O)N1c2ccc(C(=O)NCCC3CC3)cc2NC(=O)C(C)C1C]

Was synthesized analogously to Example 5 from Intermediate 2.

LC-MS (Method A): $R_t$=0.97 min; MS (ESIpos): m/z=411 [M+H]$^+$

Chiral preparatory HPLC (Chiralpak IA 5μ 250×30 mm; Eluent A: Hexane+0.1 Vol-% Diethylamine (99%); Eluent B: Ethanol; Gradient: 5-50% B over 20 min; flow rate 40.0 ml/min) yielded four stereoisomers: Example 8, Example 9, Example 10, and Example 11.

Example 8

N-(2-cyclopropylethyl)-2,3-dimethyl-1-[(3-methyl-1,2-oxazol-4-yl)carbonyl]-4-oxo-2,3,4,5-tetrahydro-1H-1,5-benzodiazepine-7-carboxamide (Isomer 1, stereochemistry not Assigned)

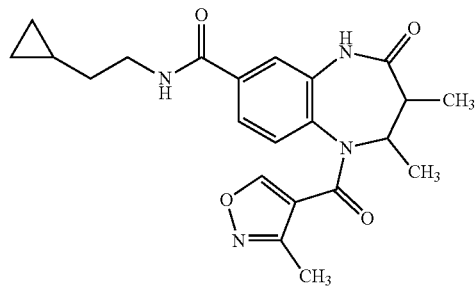 [SMILES: Cc1nocc1C(=O)N1c2ccc(C(=O)NCCC3CC3)cc2NC(=O)C(C)C1C]

LC-MS (Method A): R$_t$=0.96 min; MS (ESIpos): m/z=411 [M+H]$^+$

Chiral HPLC (Chiralpak IA 3μ 100×4.6 mm; Eluent A: Hexane+0.1 Vol-% Diethylamine (99%); Eluent B: 2-Propanol; Gradient: 5-50% B over 7 min; flow rate 1.4 mL/min; temperature 25° C.): R$_t$=5.2 min;

$^1$H-NMR (400 MHz, DMSO-d6): δ [ppm]=9.80-9.89 (m, 1H), 8.53-8.61 (m, 1H), 7.69-7.78 (m, 1H), 7.61 (d, 1H), 7.55 (br d, 1H), 7.27 (d, 1H), 4.58-4.72 (m, 1H), 3.44-3.53 (m, 2H), 2.33-2.41 (m, 1H), 2.24 (s, 3H), 1.41 (q, 2H), 1.22 (d, 3H), 1.03 (d, 3H), 0.66-0.77 (m, 1H), 0.35-0.44 (m, 2H), 0.00-0.09 (m, 2H).

Example 9

N-(2-cyclopropylethyl)-2,3-dimethyl-1-[(3-methyl-1,2-oxazol-4-yl)carbonyl]-4-oxo-2,3,4,5-tetrahydro-1H-1,5-benzodiazepine-7-carboxamide (Isomer 2, stereochemistry not assigned)

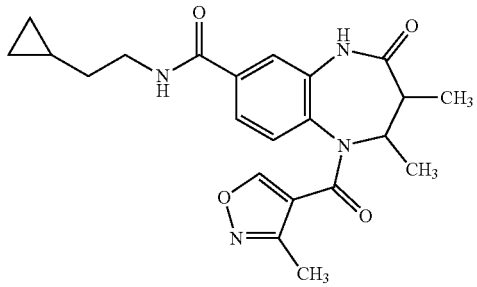 [SMILES: Cc1nocc1C(=O)N1c2ccc(C(=O)NCCC3CC3)cc2NC(=O)C(C)C1C]

LC-MS (Method A): R$_t$=0.98 min; MS (ESIpos): m/z=411 [M+H]$^+$

Chiral HPLC (Chiralpak IA 3μ 100×4.6 mm; Eluent A: Hexane+0.1 Vol-% Diethylamine (99%); Eluent B: 2-Propanol; Gradient: 5-50% B over 7 min; flow rate 1.4 mL/min; temperature 25° C.): R$_t$=6.15 min;

$^1$H-NMR (400 MHz, DMSO-d6): δ [ppm]=9.92-10.10 (m, 1H), 8.47-8.59 (m, 1H), 7.77-8.10 (m, 1H), 7.61 (s, 1H), 7.40 (br d, 1H), 6.97-7.22 (m, 1H), 5.18 (br s, 1H), 3.29 (br d, 2H), 2.80-2.98 (m, 1H), 1.93-2.28 (m, 3H), 1.34-1.46 (m, 2H), 1.09-1.25 (m, 3H), 0.80-1.00 (m, 3H), 0.65-0.75 (m, 1H), 0.33-0.43 (m, 2H), −0.02-0.09 (m, 2H).

Example 10

N-(2-cyclopropylethyl)-2,3-dimethyl-1-[(3-methyl-1,2-oxazol-4-yl)carbonyl]-4-oxo-2,3,4,5-tetrahydro-1H-1,5-benzodiazepine-7-carboxamide (Isomer 3, stereochemistry not assigned)

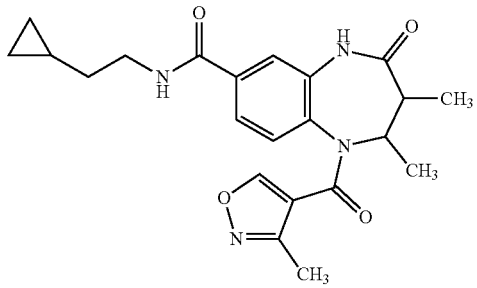 [SMILES: Cc1nocc1C(=O)N1c2ccc(C(=O)NCCC3CC3)cc2NC(=O)C(C)C1C]

LC-MS (Method A): R$_t$=0.98 min; MS (ESIpos): m/z=411 [M+H]$^+$

Chiral HPLC (Chiralpak IA 3μ 100×4.6 mm; Eluent A: Hexane+0.1 Vol-% Diethylamine (99%); Eluent B: 2-Propanol; Gradient: 5-50% B over 7 min; flow rate 1.4 mL/min; temperature 25° C.): R$_t$=7.05 min;

$^1$H-NMR (400 MHz, DMSO-d6): δ [ppm]=9.85 (s, 1H), 8.58 (t, 1H), 7.68-7.80 (m, 1H), 7.61 (d, 1H), 7.56 (br d, 1H), 7.21-7.33 (m, 1H), 4.57-4.75 (m, 1H), 3.29-3.31 (m, 1H), 2.34-2.42 (m, 1H), 2.25 (s, 3H), 1.41 (q, 2H), 1.23 (d, 3H), 1.03 (d, 3H), 0.63-0.78 (m, 1H), 0.34-0.45 (m, 2H), −0.04-0.10 (m, 2H).

Example 11

N-(2-cyclopropylethyl)-2,3-dimethyl-1-[(3-methyl-1,2-oxazol-4-yl)carbonyl]-4-oxo-2,3,4,5-tetrahydro-1H-1,5-benzodiazepine-7-carboxamide (Isomer 4, stereochemistry not assigned)

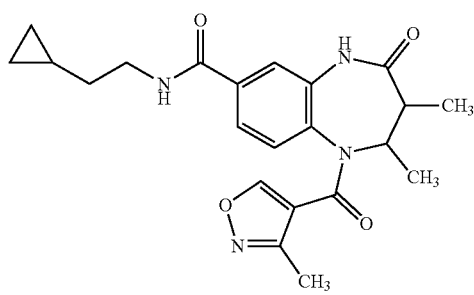 [SMILES: Cc1nocc1C(=O)N1c2ccc(C(=O)NCCC3CC3)cc2NC(=O)C(C)C1C]

LC-MS (Method A): R$_t$=0.96 min; MS (ESIpos): m/z=411 [M+H]$^+$

Chiral HPLC (Chiralpak IA 3μ 100×4.6 mm; Eluent A: Hexane+0.1 Vol-% Diethylamine (99%); Eluent B: 2-Propanol; Gradient: 5-50% B over 7 min; flow rate 1.4 mL/min; temperature 25° C.): R$_t$=7.42 min;

$^1$H-NMR (400 MHz, DMSO-d6): δ [ppm]=9.92-10.10 (m, 1H), 8.47-8.59 (m, 1H), 7.77-8.10 (m, 1H), 7.61 (s, 1H), 7.40 (br d, 1H), 6.97-7.22 (m, 1H), 5.18 (br s, 1H), 3.29 (br d, 2H), 2.80-2.98 (m, 1H), 1.93-2.28 (m, 3H), 1.34-1.46 (m, 2H), 1.09-1.25 (m, 3H), 0.80-1.00 (m, 3H), 0.65-0.75 (m, 1H), 0.33-0.43 (m, 2H), −0.02-0.09 (m, 2H).

Example 12

N-(2-cyclobutylethyl)-2,3-dimethyl-1-[(3-methyl-1,2-oxazol-4-yl)carbonyl]-4-oxo-2,3,4,5-tetrahydro-1H-1,5-benzodiazepine-7-carboxamide (mixture of stereoisomers)

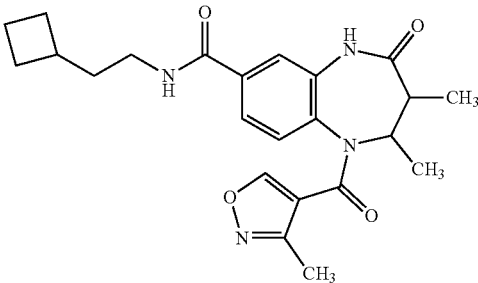 [SMILES: Cc1nocc1C(=O)N1c2ccc(C(=O)NCCC3CCC3)cc2NC(=O)C(C)C1C]

Was synthesized analogously to Example 5 from Intermediate 4.

Chiral preparatory HPLC (Chiralpak IA 5μ 250×30 mm; Eluent A: Hexane+0.1 Vol-% Diethylamine (99%); Eluent B: Ethanol; Gradient: 5-50% B over 20 min; flow rate 40.0 ml/min) yielded four stereoisomers: Example 13, Example 14, Example 15, and Example 16.

Example 13

N-(2-cyclobutylethyl)-2,3-dimethyl-1-[(3-methyl-1,2-oxazol-4-yl)carbonyl]-4-oxo-2,3,4,5-tetrahydro-1H-1,5-benzodiazepine-7-carboxamide (Isomer 1, stereochemistry not assigned)

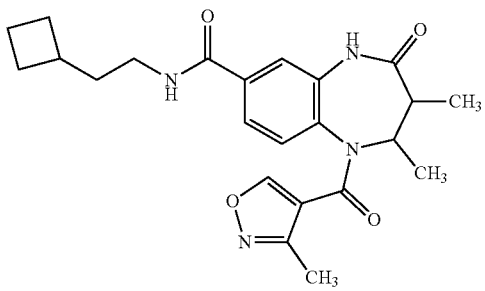 [SMILES: Cc1nocc1C(=O)N1c2ccc(C(=O)NCCC3CCC3)cc2NC(=O)C(C)C1C]

LC-MS (Method A): $R_t$=1.09 min; MS (ESIpos): m/z=425 [M+H]$^+$

Chiral HPLC (Chiralpak IA 3μ 100×4.6 mm; Eluent A: Hexane+0.1 Vol-% Diethylamine (99%); Eluent B: 2-Propanol; Gradient: 5-50% B over 7 min; flow rate 1.4 mL/min; temperature 25° C.): $R_t$=5.18 min;

$^1$H-NMR (400 MHz, DMSO-d$_6$): δ [ppm]=9.84 (s, 1H), 8.51 (t, 1H), 7.74 (s, 1H), 7.60 (d, 1H), 7.55 (br d, 1H), 7.22-7.33 (m, 1H), 4.59-4.73 (m, 1H), 3.09-3.20 (m, 2H), 2.53-2.51 (m, 1H), 2.26-2.39 (m, 2H), 2.25 (s, 2H), 1.95-2.10 (m, 2H), 1.71-1.86 (m, 2H), 1.53-1.67 (m, 4H), 1.23 (d, 3H), 1.00-1.07 (m, 3H).

Example 14

N-(2-cyclobutylethyl)-2,3-dimethyl-1-[(3-methyl-1,2-oxazol-4-yl)carbonyl]-4-oxo-2,3,4,5-tetrahydro-1H-1,5-benzodiazepine-7-carboxamide (Isomer 2, stereochemistry not assigned)

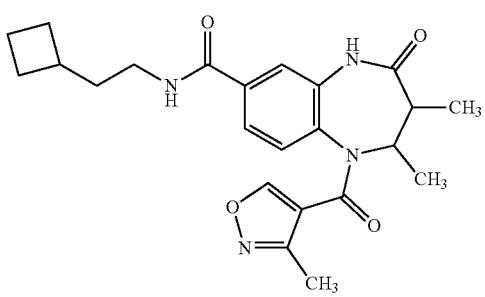 [SMILES: Cc1nocc1C(=O)N1c2ccc(C(=O)NCCC3CCC3)cc2NC(=O)C(C)C1C]

LC-MS (Method A): $R_t$=1.07 min; MS (ESIpos): m/z=425 [M+H]$^+$

Chiral HPLC (Chiralpak IA 3μ 100×4.6 mm; Eluent A: Hexane+0.1 Vol-% Diethylamine (99%); Eluent B: 2-Propanol; Gradient: 5-50% B over 7 min; flow rate 1.4 mL/min; temperature 25° C.): $R_t$=6.12 min;

$^1$H-NMR (400 MHz, DMSO-d6): δ [ppm]=9.92-10.09 (m, 1H), 8.33-8.52 (m, 1H), 7.77-8.15 (m, 1H), 7.61 (d, 1H), 7.39 (br d, 1H), 6.96-7.22 (m, 1H), 4.96-5.40 (m, 1H), 3.06-3.21 (m, 2H), 2.83-2.97 (m, 1H), 2.52 (d, 1H), 2.24-2.31 (m, 1H), 2.08-2.23 (m, 2H), 1.94-2.07 (m, 2H), 1.71-1.88 (m, 2H), 1.52-1.65 (m, 4H), 1.03-1.26 (m, 3H), 0.78-0.99 (m, 3H).

Example 15

N-(2-cyclobutylethyl)-2,3-dimethyl-1-[(3-methyl-1,2-oxazol-4-yl)carbonyl]-4-oxo-2,3,4,5-tetrahydro-1H-1,5-benzodiazepine-7-carboxamide (Isomer 3, stereochemistry not assigned)

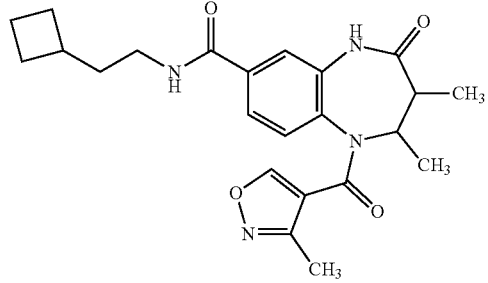 [SMILES: Cc1nocc1C(=O)N1c2ccc(C(=O)NCCC3CCC3)cc2NC(=O)C(C)C1C]

LC-MS (Method A): $R_t$=1.08 min; MS (ESIpos): m/z=425 [M+H]$^+$

Chiral HPLC (Chiralpak IA 3μ 100×4.6 mm; Eluent A: Hexane+0.1 Vol-% Diethylamine (99%); Eluent B: 2-Propanol; Gradient: 5-50% B over 7 min; flow rate 1.4 mL/min; temperature 25° C.): $R_t$=7.06 min;

$^1$H-NMR (400 MHz, DMSO-d$_6$): same as Example 13.

Example 16

N-(2-cyclobutylethyl)-2,3-dimethyl-1-[(3-methyl-1,2-oxazol-4-yl)carbonyl]-4-oxo-2,3,4,5-tetrahydro-1H-1,5-benzodiazepine-7-carboxamide (Isomer 4, stereochemistry not assigned)

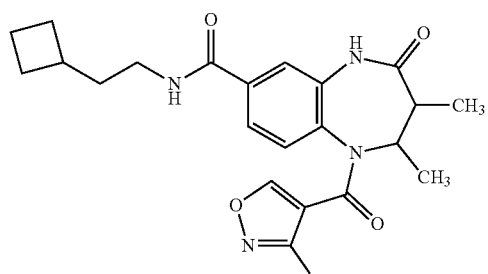

LC-MS (Method A): $R_t$=1.07 min; MS (ESIpos): m/z=425 [M+H]$^+$

Chiral HPLC (Chiralpak IA 3μ 100×4.6 mm; Eluent A: Hexane+0.1 Vol-% Diethylamine (99%); Eluent B: 2-Propanol; Gradient: 5-50% B over 7 min; flow rate 1.4 mL/min; temperature 25° C.): $R_t$=7.54 min;

$^1$H-NMR (400 MHz, DMSO-d$_6$): same as Example 14.

Example 17

1-[(4-aminopiperidin-1-yl)carbonyl]-N-(2-cyclopropyl-ethyl)-2-methyl-4-oxo-2,3,4,5-tetrahydro-1H-1,5-benzodi-azepine-7-carboxamide (racemic)

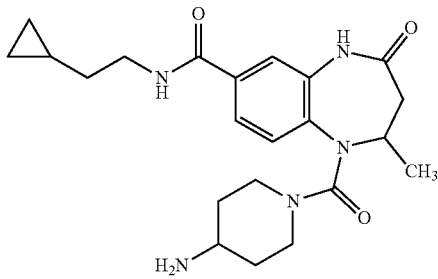 [SMILES: CC1CC(=O)Nc2cc(C(=O)NCCC3CC3)ccc2N1C(=O)N1CCC(N)CC1]

Step a)

N-(2-cyclopropylethyl)-2-methyl-4-oxo-2,3,4,5-tetra-hydro-1H-1,5-benzodiazepine-7-carboxamide (Intermediate 1, racemic, 191 mg, 665 µmol) was dissolved in THF (6 mL) and was treated with nitrophenyl chloroformate (147 mg, 731 µmol) and N,N-diisopropylethylamine (0.46 mL, 2.66 mmol). The mixture was first stirred at room temperature overnight followed by stirring at reflux for 1h. The mixture was concentrated and purified using preparative HPLC to yield the desired intermediate as yellow crystals (4-nitrophenyl 7-[(2-cyclopropylethyl)carbamoyl]-2-methyl-4-oxo-2,3,4,5-tetrahydro-1H-1,5-benzodiazepine-1-carboxylate, 162 mg, 53% yield).

LC-MS (Method A): $R_t$=1.08 min; MS (ESIpos): m/z=453 $[M+H]^+$

Step b)

The intermediate from Step a (159 mg, 351 µmol) was dissolved in DMF (2.5 mL) and treated with tert-butyl piperidin-4-ylcarbamate (352 mg, 1.76 mmol). The mixture was stirred at 70° C. for 20h. The mixture was concentrated and used crude for the next reaction.

LC-MS (Method A): $R_t$=1.05 min; MS (ESIpos): m/z=514 $[M+H]^+$

Step c)

The crude tert-butyl [1-({(2R)-7-[(2-cyclopropylethyl) carbamoyl]-2-methyl-4-oxo-2,3,4,5-tetrahydro-1H-1,5-benzodiazepin-1-yl}carbonyl)piperidin-4-yl]carbamate from Step b was dissolved in a solution of hydrochloric acid in dioxane (4M, 5 mL) and stirred at room temperature for 2h. The resulting suspension was concentrated and purified using preparative HPLC to yield 1-[(4-aminopiperidin-1-yl) carbonyl]-N-(2-cyclopropylethyl)-2-methyl-4-oxo-2,3,4,5-tetrahydro-1H-1,5-benzodiazepine-7-carboxamide (102 mg, 92% purity, 67% yield over two steps).

LC-MS (Method A): $R_t$=0.72 min; MS (ESIpos): m/z=414 $[M+H]^+$ $^1$H-NMR (400 MHz, DMSO-d6): δ [ppm]=9.84 (s, 1H), 8.53-8.65 (m, 1H), 7.77-8.03 (m, 3H), 7.67 (dd, 1H), 7.57 (d, 1H), 7.13 (d, 1H), 4.34-4.53 (m, 1H), 3.31 (br d, 3H), 2.92-3.05 (m, 2H), 2.54 (s, 1H), 2.52 (d, 1H), 2.33-2.47 (m, 2H), 2.12 (dd, 1H), 1.68 (br d, 1H), 1.52 (br d, 1H), 1.42 (q, 2H), 1.16 (d, 4H), 0.96 (br dd, 1H), 0.66-0.78 (m, 1H), 0.35-0.45 (m, 2H), 0.01-0.09 (m, 2H).

Example 18

(2R)-1-[(4-aminopiperidin-1-yl)carbonyl]-N-(2-cyclopropylethyl)-2-methyl-4-oxo-2,3,4,5-tetrahydro-1H-1,5-benzodiazepine-7-carboxamide

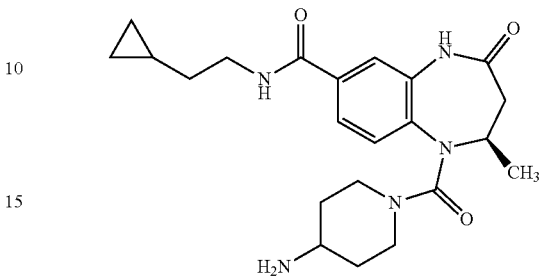

Racemic 1-[(4-aminopiperidin-1-yl)carbonyl]-N-(2-cyclopropylethyl)-2-methyl-4-oxo-2,3,4,5-tetrahydro-1H-1,5-benzodiazepine-7-carboxamide (Example 17) was separated using chiral preparatory HPLC (Chiralpak IC 5µ 250×30 mm; Eluent A: Ethanol+0.1 Vol-% Diethylamin (99%); Eluent B: Methanol; isocratic: 50% A+50% B; flow rate 50.0 ml/min) to yield both enantiomers.

The late eluting isomer was identical to Example 35 and assigned as the S-enantiomer.

The early eluting isomer was assigned as the R-enantiomer (Example 18).

Chiral HPLC (Chiralpak IC 3µ 100×4.6 mm; Eluent A: Ethanol+0.1 Vol-% Diethylamine (99%); Eluent B: Methanol; isocratic (50% A/50% B); flow rate 1.4 mL/min; temperature 25° C.): $R_t$=1.84 min;

LC-MS and $^1$H-NMR were identical to Example 17.

Example 19

1-[(4-aminopiperidin-1-yl)carbonyl]-N-(2-cyclopropyl-ethyl)-2,3-dimethyl-4-oxo-2,3,4,5-tetrahydro-1H-1,5-benzodiazepine-7-carboxamide (mixture of stereoisomers)

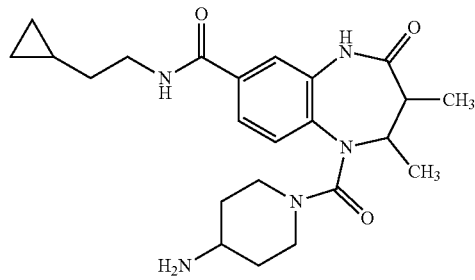 [SMILES: CC1C(=O)Nc2cc(C(=O)NCCC3CC3)ccc2N(C(=O)N2CCC(N)CC2)C1C]

Was synthesized analogously to Example 17 from Intermediate 2.

LC-MS (Method A): $R_t$=0.72 min; MS (ESIpos): m/z=428 $[M+H]^+$

1H-NMR (400 MHz, DMSO-d6) delta [ppm]: 0.000 (12.15), 0.009 (9.03), 0.021 (2.23), 0.349 (8.36), 0.365 (8.47), 0.380 (2.06), 0.670 (3.12), 0.746 (0.56), 0.769 (0.67), 0.869 (10.82), 0.885 (10.76), 0.932 (15.33), 0.947 (15.28), 1.006 (9.03), 1.021 (9.09), 1.121 (15.11), 1.135 (16.00), 1.170 (2.29), 1.197 (2.90), 1.214 (2.56), 1.222 (2.51), 1.239 (1.95), 1.331 (2.23), 1.349 (5.97), 1.361 (8.53), 1.378 (7.69), 1.396 (2.84), 1.443 (2.01), 1.472 (1.90), 1.622 (2.34), 1.650

(2.68), 2.069 (0.78), 2.084 (2.34), 2.101 (2.51), 2.112 (2.62), 2.129 (2.34), 2.276 (2.34), 2.296 (1.73), 2.329 (2.95), 2.360 (2.06), 2.488 (5.63), 2.585 (1.34), 2.618 (2.62), 2.676 (12.21), 2.687 (1.95), 2.704 (1.73), 2.837 (11.93), 2.954 (1.84), 3.156 (2.12), 3.194 (2.34), 3.243 (6.36), 3.260 (9.87), 3.334 (2.23), 3.889 (2.34), 3.904 (2.73), 3.916 (2.62), 3.932 (2.29), 3.946 (0.78), 4.171 (1.39), 4.183 (1.78), 4.197 (1.39), 5.708 (3.90), 6.831 (1.56), 6.852 (1.62), 7.096 (5.97), 7.116 (6.30), 7.488 (4.85), 7.528 (9.42), 7.550 (2.12), 7.617 (4.07), 7.637 (3.74), 7.833 (6.30), 7.899 (6.19), 8.475 (1.51), 8.529 (2.17), 8.544 (4.18), 8.558 (2.12), 9.796 (8.92), 9.849 (6.08).

Example 20

1-[(4-aminopiperidin-1-yl)carbonyl]-N-(2-cyclobutylethyl)-2,3-dimethyl-4-oxo-2,3,4,5-tetrahydro-1H-1,5-benzodiazepine-7-carboxamide (mixture of stereoisomers)

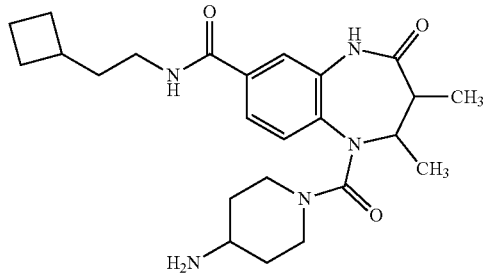 [SMILES: CC1C(=O)Nc2cc(C(=O)NCCC3CCC3)ccc2N(C(=O)N2CCC(N)CC2)C1C]

Was synthesized analogously to Example 17 from Intermediate 4.

The diastereomers were separated using preparative HPLC (column: YMC Triart C18 5µ 100×30 mm; Eluent A: water+0.2 Vol-% aq. Ammonia (32%), Eluent B: Acetonitrile; Gradient: 0.00-0.50 min 29% B (25->70 mL/min), 0.51-5.50 min 29-56% B (70 mL/min) to yield Example 21 and Example 22.

Example 21

1-[(4-aminopiperidin-1-yl)carbonyl]-N-(2-cyclobutylethyl)-2,3-dimethyl-4-oxo-2,3,4,5-tetrahydro-1H-1,5-benzodiazepine-7-carboxamide (racemic mixture of diastereomer 1, stereoisomers not assigned)

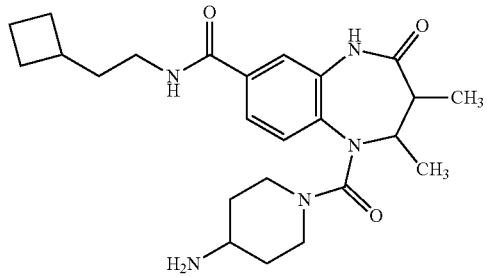 [SMILES: CC1C(=O)Nc2cc(C(=O)NCCC3CCC3)ccc2N(C(=O)N2CCC(N)CC2)C1C]

Isolated from preparative chromatography of Example 20.
LC-MS (Method A): $R_t$=0.83 min; MS (ESIpos): m/z=442 [M+H]$^+$ 1H-NMR (400 MHz, DMSO-d6) delta [ppm]: 0.786 (0.19), 0.803 (0.25), 0.852 (0.31), 0.917 (4.75), 0.934 (4.94), 0.967 (0.44), 0.985 (0.50), 1.002 (0.56), 1.045 (4.44), 1.060 (4.56), 1.107 (12.25), 1.144 (0.25), 1.180 (0.37), 1.195 (0.37), 1.232 (1.50), 1.348 (0.56), 1.489 (0.44), 1.574 (1.12), 1.586 (2.44), 1.603 (3.12), 1.622 (1.81), 1.646 (0.44), 1.734 (0.25), 1.763 (0.75), 1.772 (0.63), 1.784 (1.25), 1.806 (1.19), 1.827 (0.56), 1.849 (0.25), 1.896 (0.63), 1.981 (0.37), 1.991 (0.44), 2.010 (1.00), 2.019 (0.88), 2.030 (1.00), 2.050 (0.44), 2.059 (0.31), 2.252 (0.37), 2.271 (0.69), 2.291 (0.88), 2.311 (0.63), 2.336 (1.25), 2.348 (1.06), 2.518 (16.00), 2.523 (10.81), 2.581 (0.37), 2.615 (0.69), 2.649 (0.69), 2.678 (1.37), 2.715 (0.75), 2.727 (0.75), 2.732 (0.75), 2.744 (0.75), 3.132 (1.19), 3.153 (1.25), 3.504 (0.56), 4.194 (0.56), 4.214 (0.69), 4.229 (0.75), 4.240 (0.63), 6.854 (0.75), 6.874 (0.75), 7.526 (1.88), 7.530 (2.63), 7.542 (1.44), 7.547 (0.94), 7.563 (1.12), 7.568 (0.94), 8.376 (0.56), 8.390 (1.00), 8.403 (0.50), 8.439 (0.37), 9.888 (1.94).

Example 22

1-[(4-aminopiperidin-1-yl)carbonyl]-N-(2-cyclobutylethyl)-2,3-dimethyl-4-oxo-2,3,4,5-tetrahydro-1H-1,5-benzodiazepine-7-carboxamide (racemic mixture of diastereomer 2, stereoisomers not assigned)

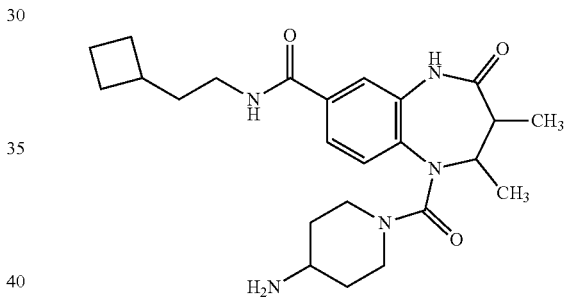

Isolated from preparative chromatography of Example 20.
LC-MS (Method A): $R_t$=0.87 min; MS (ESIpos): m/z=442 [M+H]+

1H-NMR (400 MHz, DMSO-d6) delta [ppm]: 0.762 (0.26), 0.786 (0.39), 0.851 (0.20), 0.944 (0.20), 0.960 (0.20), 0.981 (4.11), 0.998 (4.24), 1.048 (0.33), 1.107 (10.45), 1.168 (4.11), 1.183 (4.05), 1.232 (0.85), 1.269 (0.26), 1.297 (0.33), 1.349 (0.33), 1.370 (0.39), 1.539 (0.33), 1.582 (1.37), 1.600 (2.16), 1.619 (1.89), 1.634 (1.04), 1.654 (0.33), 1.751 (0.46), 1.770 (0.78), 1.779 (0.65), 1.790 (1.11), 1.812 (0.91), 1.834 (0.46), 1.855 (0.26), 1.897 (0.65), 1.989 (0.33), 2.000 (0.33), 2.010 (0.59), 2.017 (0.78), 2.028 (0.65), 2.038 (0.72), 2.057 (0.33), 2.067 (0.26), 2.076 (0.33), 2.124 (0.65), 2.140 (0.65), 2.151 (0.65), 2.167 (0.59), 2.263 (0.26), 2.283 (0.52), 2.302 (0.65), 2.332 (2.94), 2.336 (1.44), 2.362 (0.46), 2.391 (0.26), 2.518 (16.00), 2.523 (10.78), 2.536 (1.18), 2.539 (1.83), 2.678 (1.24), 2.734 (0.33), 2.881 (0.20), 2.983 (0.46), 3.015 (0.46), 3.090 (0.72), 3.152 (1.37), 3.172 (1.50), 3.190 (1.24), 3.504 (0.91), 3.931 (0.65), 3.946 (0.72), 3.959 (0.72), 3.974 (0.65), 5.922 (0.20), 7.129 (1.76), 7.150 (1.76), 7.561 (1.83), 7.566 (2.02), 7.639 (1.11), 7.644 (0.98), 7.659 (0.98), 7.665 (0.85), 8.374 (2.29), 8.506 (0.39), 8.520 (0.85), 8.534 (0.39), 9.853 (1.31).

Example 23

(2S)-1-(3-azabicyclo[3.1.0]hex-3-ylcarbonyl)-N-(2-cyclopropylethyl)-2-methyl-4-oxo-2,3,4,5-tetrahydro-1H-1,5-benzodiazepine-7-carboxamide

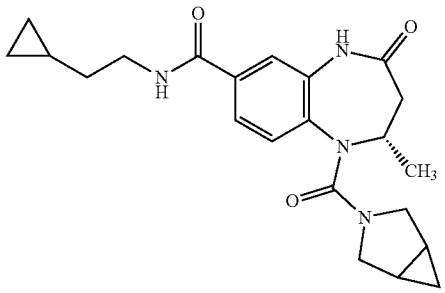 [SMILES: C[C@H]1CC(=O)Nc2cc(C(=O)NCCC3CC3)ccc2N1C(=O)N1CC2CC2C1]

To a round-bottomed flask were added (2S)—N-(2-cyclopropylethyl)-2-methyl-4-oxo-2,3,4,5-tetrahydro-1H-1,5-benzodiazepine-7-carboxamide (Intermediate 8, 100 mg, 348 μmol), THF (2.0 ml), and N,N-diisopropylethylamine (300 μl, 1.7 mmol). Triphosgene (62.0 mg, 209 μmol) was added under ice bath cooling and the reaction mixture was stirred at room temperature for 30 mins. 3-azabicyclo[3.1.0] hexane hydrochloride (1:1) (104 mg, 870 μmol) was added and the reaction mixture was monitored by UPLC-MS. Once complete the reaction mixture was partitioned between ethyl acetate and saturated aqueous sodium bicarbonate solution. The aqueous layer was removed and the organic layer was further washed with brine. The organic layer was dried over anhydrous sodium sulfate, filtered, and concentrated. The residue was purified by prep HPLC (XBridge C18, 19×150 mm, 5 um, 0.1% ammonium hydroxide in water-acetonitrile; 20-70% over 7 min; r.t. 4.82 min) to yield the title compound as a white solid, 93 mg (66%).

UPLC (Method B) 0.62 min, 98% purity, (M+H)+ 397.
$^1$H-NMR (400 MHz, CHLOROFORM-d): δ [ppm]=8.18 (br s, 1H), 7.61 (d, 1H), 7.54 (dd, 1H), 7.14 (d, 1H), 6.30-6.47 (m, 1H), 4.66-4.81 (m, 1H), 3.53-3.62 (m, 2H), 3.42-3.53 (m, 1H), 2.90-3.08 (m, 2H), 2.60 (br d, 1H), 2.45-2.57 (m, 1H), 2.19-2.31 (m, 1H), 1.55 (q, 2H), 1.15-1.35 (m, 5H), 0.68-0.84 (m, 1H), 0.45-0.58 (m, 3H), 0.07-0.20 (m, 2H), −0.06 (q, 1H).

Example 24

(2S)—N-(2-cyclopropylethyl)-1-[(3,3-difluoropyrrolidin-1-yl)carbonyl]-2-methyl-4-oxo-2,3,4,5-tetrahydro-1H-1,5-benzodiazepine-7-carboxamide

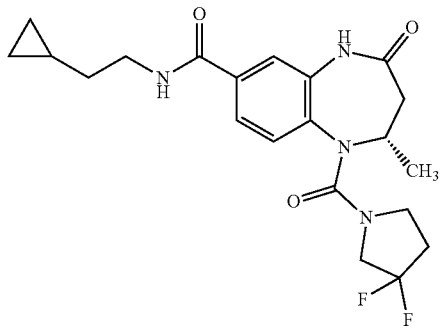 [SMILES: C[C@H]1CC(=O)Nc2cc(C(=O)NCCC3CC3)ccc2N1C(=O)N1CCC(F)(F)C1]

Was synthesized analogously to Example 23 from Intermediate 8 and 3,3-difluoro-pyrrolidine.
UPLC (Method C) 1.72 min, 96% purity, (M+H)+ 421.
$^1$H-NMR (400 MHz, METHANOL-D$_3$): δ [ppm]=7.69 (dd, 1H), 7.60 (d, 1H), 7.28 (d, 1H), 4.70 (tt, 1H), 3.39-3.51 (m, 2H), 3.12-3.26 (m, 2H), 2.87-3.11 (m, 3H), 2.39-2.49 (m, 1H), 2.31 (dd, 1H), 2.02-2.25 (m, 3H), 1.50 (d, 2H), 1.27 (d, 3H), 0.66-0.81 (m, 1H), 0.41-0.51 (m, 2H), 0.03-0.13 (m, 2H).

Example 25

(2S)—N-(2-cyclopropylethyl)-1-[(4,4-difluoropiperidin-1-yl)carbonyl]-2-methyl-4-oxo-2,3,4,5-tetrahydro-1H-1,5-benzodiazepine-7-carboxamide

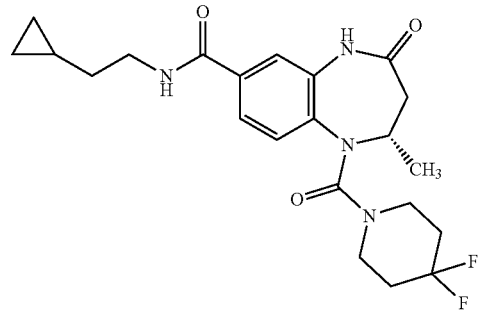 [SMILES: C[C@H]1CC(=O)Nc2cc(C(=O)NCCC3CC3)ccc2N1C(=O)N1CCC(F)(F)CC1]

Was synthesized analogously to Example 23 from Intermediate 8 and 4,4-difluoro-piperidine.
UPLC (Method B) 0.66 min, 99% purity, (M+H)+ 435.
$^1$H-NMR (400 MHz, CHLOROFORM-d): δ [ppm]=8.35 (s, 1H), 7.66 (d, 1H), 7.52 (dd, 1H), 7.15 (d, 1H), 6.35 (br t, 1H), 4.62-4.78 (m, 1H), 3.51-3.63 (m, 2H), 3.00-3.14 (m, 4H), 2.55 (dd, 1H), 2.26 (dd, 1H), 1.58-1.75 (m, 4H), 1.53 (q, 2H), 1.30 (d, 3H), 0.63-0.81 (m, 1H), 0.40-0.59 (m, 2H), 0.03-0.19 (m, 2H).

Example 26

(2S)—N-(2-cyclopropylethyl)-1-{[4-(2-hydroxyethyl)piperazin-1-yl]carbonyl}-2-methyl-4-oxo-2,3,4,5-tetrahydro-1H-1,5-benzodiazepine-7-carboxamide

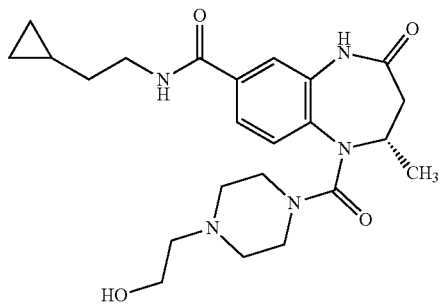 [SMILES: C[C@H]1CC(=O)Nc2cc(C(=O)NCCC3CC3)ccc2N1C(=O)N1CCN(CCO)CC1]

Was synthesized analogously to Example 23 from Intermediate 8 and 2-(piperazine-1-yl)ethanol.
UPLC (Method B) 0.54 min, 99% purity, (M+H)+ 444.
$^1$H-NMR (400 MHz, CHLOROFORM-d): δ [ppm]=7.90-8.02 (m, 1H), 7.49-7.63 (m, 2H), 7.15 (d, 1H), 6.36 (br t, 1H), 4.71 (dt, 1H), 3.50-3.62 (m, 4H), 3.00 (br t, 4H), 2.57

(dd, 1H), 2.45 (t, 2H), 2.17-2.34 (m, 5H), 1.55 (q, 2H), 1.32 (d, 3H), 0.87-0.98 (m, 1H), 0.67-0.81 (m, 1H), 0.45-0.58 (m, 2H), 0.13 (q, 2H).

Example 27

(2S)—N-(2-cyclopropylethyl)-1-[(4-ethylpiperazin-1-yl)carbonyl]-2-methyl-4-oxo-2,3,4,5-tetrahydro-1H-1,5-benzodiazepine-7-carboxamide

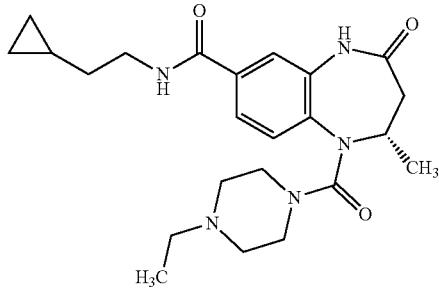 [SMILES: CCN1CCN(C(=O)N2c3ccc(C(=O)NCCC4CC4)cc3NC(=O)C[C@@H]2C)CC1]

Was synthesized analogously to Example 23 from Intermediate 8 and 1-ethyl-piperazine.

UPLC (Method B) 0.59 min, 99% purity, (M+H)+ 428.

$^1$H-NMR (400 MHz, CHLOROFORM-d): δ [ppm]=7.59 (d, 1H), 7.47-7.54 (m, 1H), 7.39 (br s, 1H), 7.14 (d, 1H), 6.20-6.32 (m, 1H), 4.64-4.78 (m, 1H), 3.50-3.64 (m, 2H), 2.94-3.18 (m, 3H), 2.59 (ddd, 1H), 2.34 (q, 2H), 2.09-2.29 (m, 4H), 1.56 (q, 2H), 1.33 (d, 3H), 1.02 (t, 3H), 0.68-0.83 (m, 1H), 0.46-0.58 (m, 2H), 0.04-0.18 (m, 2H).

Example 28

(2S)—N$^7$-(2-cyclopropylethyl)-N$^1$-(1-ethylpiperidin-4-yl)-N$^1$,2-dimethyl-4-oxo-2,3,4,5-tetrahydro-1H-1,5-benzodiazepine-1,7-dicarboxamide

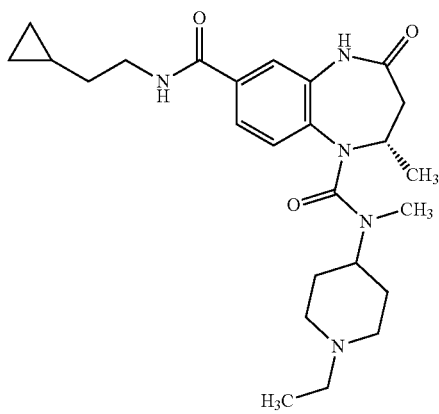 [SMILES: CCN1CCC(N(C)C(=O)N2c3ccc(C(=O)NCCC4CC4)cc3NC(=O)C[C@@H]2C)CC1]

Was synthesized analogously to Example 23 from Intermediate 8 and 1-ethyl-N-methylpiperidin-4-amine UPLC (Method B) 0.61 min, 99% purity, (M+H)+ 456.

$^1$H-NMR (400 MHz, CHLOROFORM-d): δ [ppm]=7.54 (d, 1H), 7.49 (br dd, 2H), 7.12 (d, 1H), 6.13-6.30 (m, 1H), 4.62-4.73 (m, 1H), 3.72-3.89 (m, 1H), 3.45-3.61 (m, 2H), 2.95 (br d, 2H), 2.57 (br dd, 1H), 2.38 (q, 2H), 2.25 (dd, 1H), 2.15 (s, 2H), 1.81-1.99 (m, 2H), 1.36-1.63 (m, 5H), 1.31 (d, 3H), 1.05 (t, 3H), 0.65-0.84 (m, 1H), 0.38-0.58 (m, 2H), 0.12 (q, 2H).

Example 29

(2S)—N-(2-cyclopropylethyl)-2-methyl-4-oxo-1-({4-[(2,2,2-trifluoroethyl)amino]piperidin-1-yl}carbonyl)-2,3,4,5-tetrahydro-1H-1,5-benzodiazepine-7-carboxamide

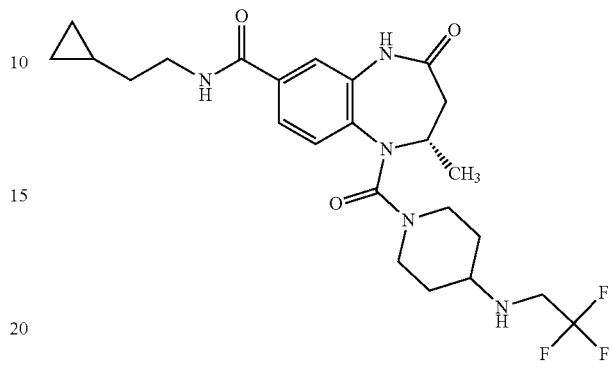

Was synthesized analogously to Example 23 from Intermediate 8 and N-(2,2,2-trifluoroethyl)piperidin-4-amine UPLC (Method B) 0.65 min, 93% purity, (M+H)+ 496.

$^1$H-NMR (400 MHz, CHLOROFORM-d): δ [ppm]=7.65-7.76 (m, 1H), 7.55-7.65 (m, 1H), 7.51 (dd, 1H), 7.14 (d, 1H), 6.24-6.41 (m, 1H), 4.68 (dq, 1H), 3.45-3.61 (m, 3H), 3.35 (br d, 1H), 3.10 (q, 2H), 2.44-2.62 (m, 3H), 2.14-2.30 (m, 1H), 1.47-1.73 (m, 7H), 1.29 (d, 3H), 0.98-1.14 (m, 1H), 0.68-0.93 (m, 3H), 0.43-0.58 (m, 2H), 0.01-0.21 (m, 2H).

Example 30

(2S)—N-(2-cyclopropylethyl)-2-methyl-4-oxo-1-{[4-(2,2,2-trifluoroethyl)piperazin-1-yl]carbonyl}-2,3,4,5-tetrahydro-1H-1,5-benzodiazepine-7-carboxamide

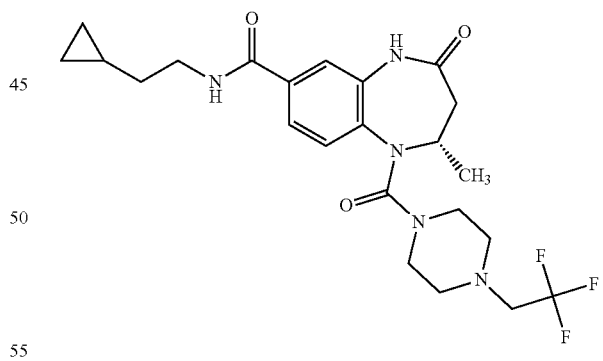

Was synthesized analogously to Example 23 from Intermediate 8 and N-(2,2,2-trifluoroethyl) piperazine UPLC (Method B) 0.68 min, 99% purity, (M+H)+ 482.

$^1$H-NMR (400 MHz, CHLOROFORM-d): δ [ppm]=7.80 (s, 1H), 7.56-7.62 (m, 1H), 7.45-7.56 (m, 1H), 7.12 (d, 1H), 6.26 (br s, 1H), 4.59-4.75 (m, 1H), 3.51-3.64 (m, 2H), 2.92-3.07 (m, 5H), 2.79-2.92 (m, 3H), 2.49-2.61 (m, 1H), 2.31-2.45 (m, 5H), 2.20-2.31 (m, 1H), 1.54 (q, 3H), 1.30 (d, 5H), 0.64-0.83 (m, 2H), 0.42-0.58 (m, 3H), 0.02-0.22 (m, 3H).

Example 31

(2S)—N$^7$-(2-cyclopropylethyl)-N$^1$,2-dimethyl-4-oxo-N$^1$-[1-(2,2,2-trifluoroethyl)piperidin-4-yl]-2,3,4,5-tetrahydro-1H-1,5-benzodiazepine-1,7-dicarboxamide

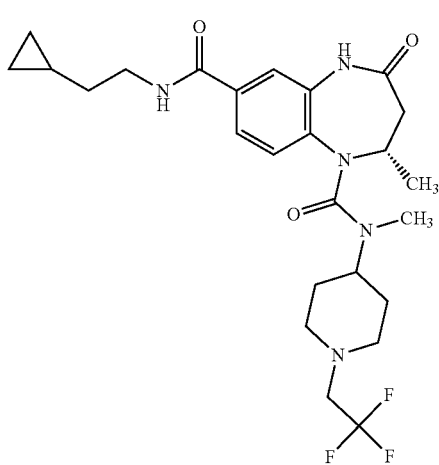 [SMILES: C[C@H]1CC(=O)Nc2cc(C(=O)NCCC3CC3)ccc2N1C(=O)N(C)C1CCN(CC(F)(F)F)CC1]

Was synthesized analogously to Example 23 from Intermediate 8 N-methyl-1-(2,2,2-trifluoroethyl)piperidin-4-amine UPLC (Method B) 0.7 min, >98% purity, (M+H)+ 510.

$^1$H-NMR (400 MHz, CHLOROFORM-d): δ [ppm]=7.99 (s, 1H), 7.59 (d, 1H), 7.52 (dd, 1H), 7.13 (d, 1H), 6.30 (br t, 1H), 4.59-4.75 (m, 1H), 3.77 (qd, 1H), 3.50-3.64 (m, 2H), 2.92 (q, 4H), 2.48-2.63 (m, 1H), 2.37 (br t, 2H), 2.28 (dd, 1H), 2.13 (s, 3H), 1.36-1.65 (m, 6H), 1.33 (d, 3H), 0.64-0.84 (m, 1H), 0.42-0.62 (m, 2H), 0.04-0.22 (m, 2H).

Example 32 tert-butyl 4-({(2S)-7-[(2-cyclopropylethyl)carbamoyl]-2-methyl-4-oxo-2,3,4,5-tetrahydro-1H-1,5-benzodiazepin-1-yl}carbonyl)-1,4-diazepane-1-carboxylate

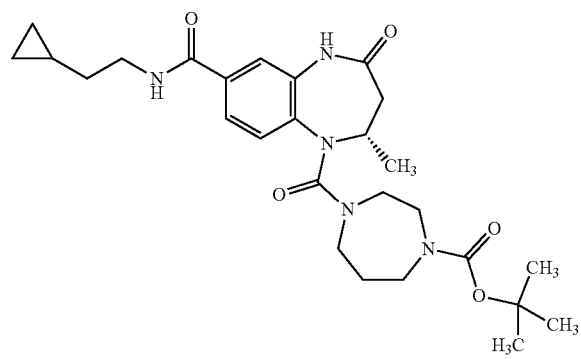 [SMILES: C[C@H]1CC(=O)Nc2cc(C(=O)NCCC3CC3)ccc2N1C(=O)N1CCCN(C(=O)OC(C)(C)C)CC1]

Was synthesized analogously to Example 23 from Intermediate 8 and tert-butyl 1,4-diazepane-1-carboxylate UPLC (Method B) 0.69 min, 96%, (M+H)+ 514.

Example 33

(2S)—N-(2-cyclopropylethyl)-1-(1,4-diazepan-1-ylcarbonyl)-2-methyl-4-oxo-2,3,4,5-tetrahydro-1H-1,5-benzodiazepine-7-carboxamide

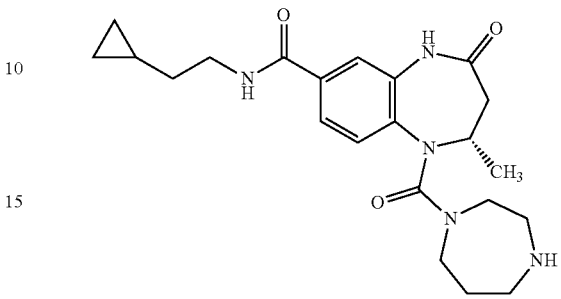

Tert-butyl 4-({(2S)-7-[(2-cyclopropylethyl)carbamoyl]-2-methyl-4-oxo-2,3,4,5-tetrahydro-1H-1,5-benzodiazepin-1-yl}carbonyl)-1,4-diazepane-1-carboxylate (Example 32, 68.0 mg, 132 μmol) was diluted with HCl in dioxane (4M, 5.0 ml) and stirred for 1 hr. LCMS indicates complete conversion. The solvent was removed by evaporation and the crude HCl salt was passed through an SCX-2 cartridge eluting with 17% NH3 in methanol-DCM (2:8) to yield the title compound. Further purification by prep HPLC (XBridge C18, 19×150 mm, 5 um, 0.1% ammonium hydroxide in water-acetonitrile; 10-50% over 7 min; r.t. 5.79 min) yielded the title compound as a white solid, 27.0 mg (49%).

UPLC (Method B) 0.55 min, 96% purity, (M+H)+ 414.

$^1$H-NMR (400 MHz, CHLOROFORM-d): δ [ppm]=7.71-7.91 (m, 1H), 7.45-7.60 (m, 2H), 7.10-7.18 (m, 1H), 6.41 (br s, 1H), 4.59-4.77 (m, 1H), 3.57 (q, 2H), 2.98-3.16 (m, 3H), 2.88-2.98 (m, 1H), 2.51-2.84 (m, 5H), 2.20-2.34 (m, 1H), 1.48-1.64 (m, 4H), 1.34 (d, 3H), 0.65-0.81 (m, 1H), 0.43-0.57 (m, 2H), 0.05-0.19 (m, 2H).

Example 34 tert-butyl [1-({(2S)-7-[(2-cyclopropylethyl)carbamoyl]-2-methyl-4-oxo-2,3,4,5-tetrahydro-1H-1,5-benzodiazepin-1-yl}carbonyl)piperidin-4-yl]carbamate

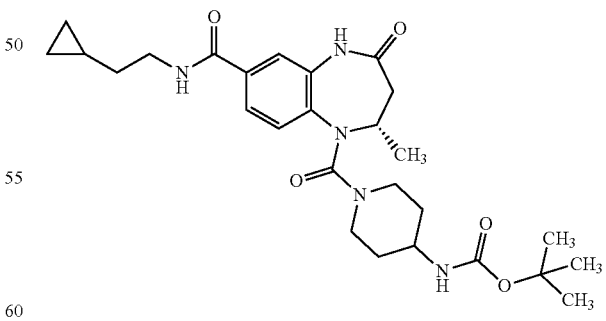

Was synthesized analogously to Example 23 from Intermediate 8 and tert-butyl piperidin-4-ylcarbamate The crude residue was used in the subsequent step without any further purification.

UPLC (Method B) 0.68 min, 40% purity, (M+H)+ 514.

Example 35

(2S)-1-[(4-aminopiperidin-1-yl)carbonyl]-N-(2-cyclopropylethyl)-2-methyl-4-oxo-2,3,4,5-tetrahydro-1H-1,5-benzodiazepine-7-carboxamide

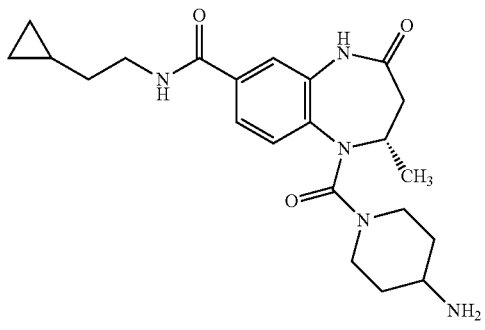 [SMILES: C[C@H]1CC(=O)Nc2cc(C(=O)NCCC3CC3)ccc2N1C(=O)N1CCC(N)CC1]

Was synthesized analogously to Example 33 from Example 34 and was identical to the late eluting isomer from Example 18.

Chiral HPLC (Chiralpak IC 3μ 100×4.6 mm; Eluent A: Ethanol+0.1 Vol-% Diethylamine (99%); Eluent B: Methanol; isocratic (50% A/50% B); flow rate 1.4 mL/min; temperature 25° C.): $R_t$=2.72 min;

UPLC (Method C) 1.55 min, >98% purity, (M+H)+ 414.

$^1$H-NMR (400 MHz, CHLOROFORM-d): δ [ppm]=7.97 (br s, 1H), 7.59 (d, 1H), 7.52 (dd, 1H), 7.09-7.20 (m, 1H), 6.41 (br t, 1H), 4.60-4.77 (m, 1H), 3.47-3.63 (m, 3H), 3.40 (br d, 1H), 2.62-2.77 (m, 1H), 2.40-2.62 (m, 3H), 2.26 (dd, 1H), 1.40-1.67 (m, 7H), 1.31 (d, 3H), 0.94-1.12 (m, 1H), 0.69-0.89 (m, 2H), 0.44-0.62 (m, 2H), 0.04-0.22 (m, 2H).

Example 36 tert-butyl [(3S)-1-({(2S)-7-[(2-cyclopropylethyl)carbamoyl]-2-methyl-4-oxo-2,3,4,5-tetrahydro-1H-1,5-benzodiazepin-1-yl}carbonyl)pyrrolidin-3-yl]carbamate

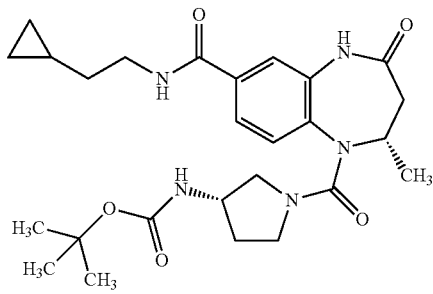 [SMILES: C[C@H]1CC(=O)Nc2cc(C(=O)NCCC3CC3)ccc2N1C(=O)N1CC[C@H](NC(=O)OC(C)(C)C)C1]

Was synthesized analogously to Example 23 from Intermediate 8 and tert-butyl (3S)-pyrrolidin-3-ylcarbamate $^1$H-NMR (400 MHz, CHLOROFORM-d): δ [ppm]=8.18 (br d, 1H), 7.53-7.61 (m, 2H), 7.20 (d, 1H), 6.44 (br s, 1H), 4.79 (dt, 1H), 4.57 (d, 1H), 3.95 (br s, 1H), 3.57 (q, 2H), 3.14-3.27 (m, 1H), 3.03 (br t, 1H), 2.43-2.74 (m, 3H), 2.27 (dd, 1H), 1.84-2.08 (m, 3H), 1.47-1.61 (m, 3H), 1.40 (s, 9H), 1.25-1.36 (m, 3H), 0.66-0.83 (m, 1H), 0.44-0.57 (m, 2H), 0.07-0.19 (m, 2H).

Example 37

(2S)-1-{[(3S)-3-aminopyrrolidin-1-yl]carbonyl}-N-(2-cyclopropylethyl)-2-methyl-4-oxo-2,3,4,5-tetrahydro-1H-1,5-benzodiazepine-7-carboxamide hydrochloride (1:1)

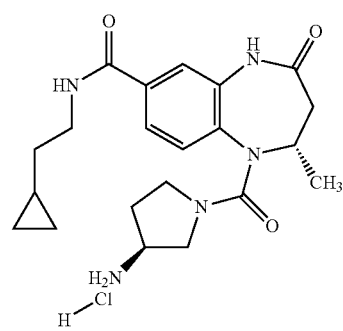

Was synthesized analogously to Example 33 from Example 36. The crude product was triturated with diethyl ether to yield sufficiently pure material.

UPLC (Method B) 0.54 min, >98% purity, (M+H)+ 400.

$^1$H-NMR (400 MHz, DMSO-$d_6$): δ [ppm]=9.84 (s, 1H), 8.55 (br t, 1H), 8.05 (br s, 3H), 7.59-7.69 (m, 1H), 7.55 (s, 1H), 7.05-7.23 (m, 1H), 4.51 (dt, 1H), 3.43-3.60 (m, 3H), 2.99-3.15 (m, 1H), 2.91 (br d, 2H), 2.23-2.35 (m, 1H), 2.04-2.16 (m, 1H), 1.82-1.98 (m, 1H), 1.64 (br dd, 1H), 1.38 (q, 2H), 1.01-1.24 (m, 3H), 0.68 (br d, 1H), 0.25-0.49 (m, 2H), −0.06-0.09 (m, 2H).

Example 38 tert-butyl [(3R)-1-({(2S)-7-[(2-cyclopropylethyl)carbamoyl]-2-methyl-4-oxo-2,3,4,5-tetrahydro-1H-1,5-benzodiazepin-1-yl}carbonyl)pyrrolidin-3-yl]carbamate

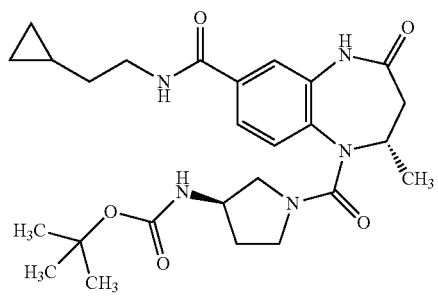 [SMILES: C[C@H]1CC(=O)Nc2cc(C(=O)NCCC3CC3)ccc2N1C(=O)N1CC[C@@H](NC(=O)OC(C)(C)C)C1]

Was synthesized analogously to Example 23 from Intermediate 8 and tert-butyl (3R)-pyrrolidin-3-ylcarbamate UPLC (Method B) 0.67 min, >98% purity, (M+H)+ 500.

Example 39

(2S)-1-{[(3R)-3-aminopyrrolidin-1-yl]carbonyl}-N-(2-cyclopropylethyl)-2-methyl-4-oxo-2,3,4,5-tetrahydro-1H-1,5-benzodiazepine-7-carboxamide hydrochloride (1:1)

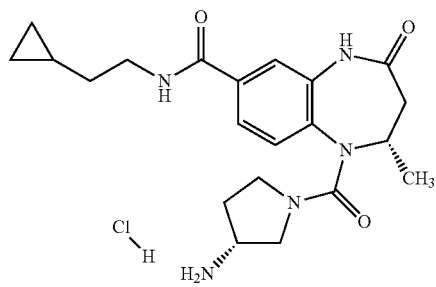 [SMILES: C[C@H]1CC(=O)Nc2cc(C(=O)NCCC3CC3)ccc2N1C(=O)N1CC[C@@H](N)C1 ; Cl]

Was synthesized analogously to Example 33 from Example 38. The crude product was triturated with diethyl ether to yield sufficiently pure material.

UPLC (Method B) 0.54 min, 93% purity, (M+H)+ 400.

$^1$H-NMR (400 MHz, DMSO-$d_6$): δ [ppm]=9.81 (s, 1H), 8.47-8.57 (m, 1H), 7.73-7.95 (m, 3H), 7.59-7.67 (m, 1H), 7.56 (br d, 1H), 7.10-7.18 (m, 1H), 4.46-4.57 (m, 1H), 3.52-3.63 (m, 1H), 2.73-2.96 (m, 3H), 2.24-2.42 (m, 3H), 2.04-2.18 (m, 2H), 1.82-1.95 (m, 2H), 1.60-1.75 (m, 2H), 1.31-1.44 (m, 2H), 1.06-1.19 (m, 2H), 0.66-0.74 (m, 1H), 0.30-0.43 (m, 2H), −0.03-0.07 (m, 2H).

Example 40 tert-butyl 4-({(2S)-7-[(2-cyclopropylethyl)carbamoyl]-2-methyl-4-oxo-2,3,4,5-tetrahydro-1H-1,5-benzodiazepin-1-yl}carbonyl)piperazine-1-carboxylate

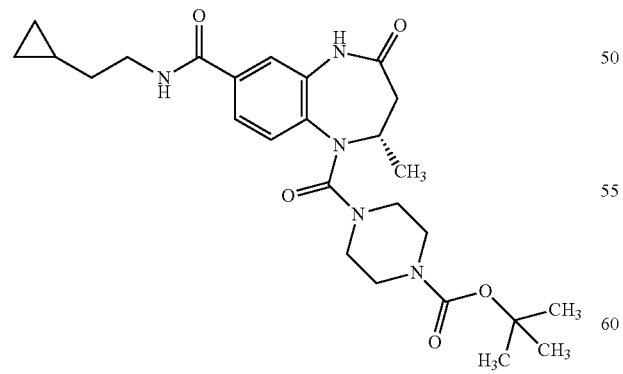

Was synthesized analogously to Example 23 from Intermediate 8 and tert-butyl piperazine-1-carboxylate and used in the next step without purification.

Example 41

(2S)—N-(2-cyclopropylethyl)-2-methyl-4-oxo-1-(piperazin-1-ylcarbonyl)-2,3,4,5-tetrahydro-1H-1,5-benzodiazepine-7-carboxamide

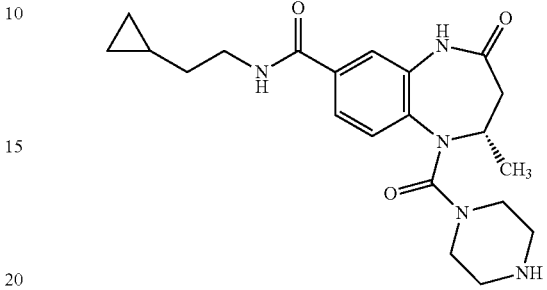

Was synthesized analogously to Example 33 from Example 40.

UPLC (Method C) 1.53 min, >98% purity, (M+H)+ 400.

$^1$H-NMR (400 MHz, CHLOROFORM-d): δ [ppm]=8.47 (br s, 1H), 7.60 (d, 1H), 7.54 (dd, 1H), 7.14 (d, 1H), 6.49 (br t, 1H), 4.61-4.76 (m, 1H), 3.51-3.62 (m, 2H), 2.86-3.03 (m, 4H), 2.45-2.63 (m, 5H), 2.26 (dd, 1H), 1.55 (q, 2H), 1.31 (d, 3H), 0.69-0.83 (m, 1H), 0.44-0.60 (m, 2H), 0.06-0.19 (m, 2H).

Example 42 tert-butyl 4-[({(2S)-7-[(2-cyclopropylethyl)carbamoyl]-2-methyl-4-oxo-2,3,4,5-tetrahydro-1H-1,5-benzodiazepin-1-yl}carbonyl)amino]piperidine-1-carboxylate

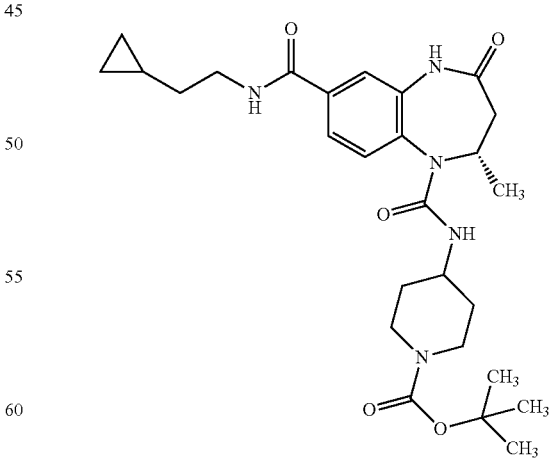

Was synthesized analogously to Example 23 from Intermediate 8 and tert-butyl 4-aminopiperidine-1-carboxylate and used in the next step without purification.

Example 43

(2S)—N⁷-(2-cyclopropylethyl)-2-methyl-4-oxo-N¹-(piperidin-4-yl)-2,3,4,5-tetrahydro-1H-1,5-benzodiazepine-1,7-dicarboxamide

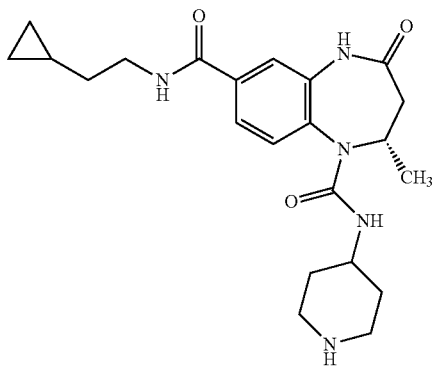 [SMILES: C[C@H]1CC(=O)Nc2cc(C(=O)NCCC3CC3)ccc2N1C(=O)NC1CCNCC1]

Was synthesized analogously to Example 33 from Example 42.

UPLC (Method B) 0.55 min, >98% purity, (M+H)+ 414.

¹H-NMR (400 MHz, CHLOROFORM-d): δ [ppm]=7.69-7.84 (m, 1H), 7.65 (br d, 1H), 7.27 (br t, 2H), 5.00-5.18 (m, 1H), 4.26-4.52 (m, 1H), 3.59-3.77 (m, 2H), 3.38-3.59 (m, 3H), 2.89-3.11 (m, 3H), 2.52-2.74 (m, 3H), 2.29 (br s, 1H), 2.19 (br t, 1H), 1.70-1.90 (m, 2H), 1.39-1.63 (m, 3H), 0.97-1.30 (m, 6H), 0.64-0.79 (m, 1H), 0.39-0.55 (m, 2H), 0.09 (br d, 2H).

Example 44 tert-butyl 4-[({(2S)-7-[(2-cyclopropylethyl)carbamoyl]-2-methyl-4-oxo-2,3,4,5-tetrahydro-1H-1,5-benzodiazepin-1-yl}carbonyl)(methyl)amino]piperidine-1-carboxylate

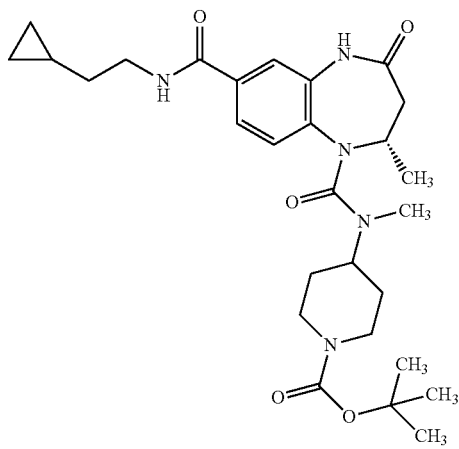 [SMILES: C[C@H]1CC(=O)Nc2cc(C(=O)NCCC3CC3)ccc2N1C(=O)N(C)C1CCN(C(=O)OC(C)(C)C)CC1]

Was synthesized analogously to Example 23 from Intermediate 8 and tert-butyl 4-(methylamino)piperidine-1-carboxylate and used in the next step without purification.

UPLC (Method C) 1.9 min, 54% purity, (M+H)+ 528.

Example 45

(2S)—N⁷-(2-cyclopropylethyl)-N¹,2-dimethyl-4-oxo-N¹-(piperidin-4-yl)-2,3,4,5-tetrahydro-1H-1,5-benzodiazepine-1,7-dicarboxamide

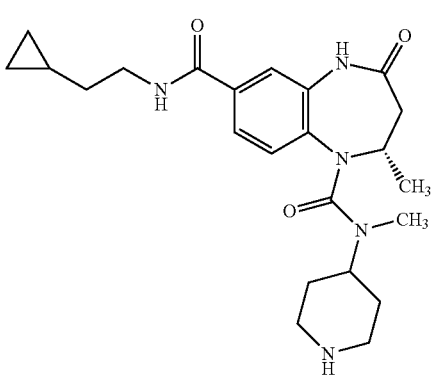 [SMILES: C[C@H]1CC(=O)Nc2cc(C(=O)NCCC3CC3)ccc2N1C(=O)N(C)C1CCNCC1]

Was synthesized analogously to Example 33 from Example 44.

UPLC (Method B) 0.56 min, 98% purity, (M+H)+ 428.

¹H-NMR (400 MHz, CHLOROFORM-d): δ [ppm]=7.64 (dd, 1H), 7.60 (d, 1H), 7.36 (d, 1H), 6.37-6.47 (m, 1H), 5.20-5.29 (m, 1H), 4.03 (br t, 1H), 3.55-3.62 (m, 2H), 3.10-3.17 (m, 1H), 2.99-3.09 (m, 4H), 2.51-2.61 (m, 2H), 2.48 (br dd, 1H), 2.21-2.32 (m, 2H), 1.46-1.60 (m, 6H), 1.23 (d, 3H), 1.16-1.20 (m, 1H), 1.13 (d, 1H), 0.95-1.08 (m, 3H), 0.71-0.79 (m, 1H), 0.49-0.56 (m, 2H), 0.11-0.17 (m, 2H).

Example 46

1-(2-fluorobenzoyl)-2-methyl-4-oxo-N-pentyl-2,3,4,5-tetrahydro-1H-1,5-benzodiazepine-7-carboxamide (racemic)

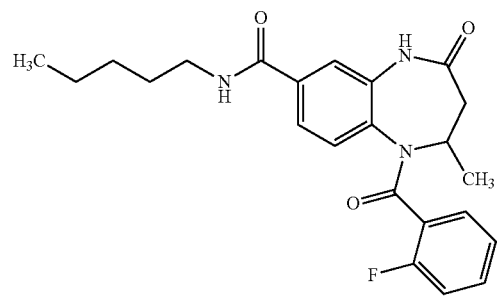 [SMILES: CCCCCNC(=O)c1ccc2c(c1)NC(=O)CC(C)N2C(=O)c1ccccc1F]

Can be synthesized analogously to Example 1.

Example 47

2-methyl-1-(4-methylbenzoyl)-4-oxo-N-pentyl-2,3,4,5-tetrahydro-1H-1,5-benzodiazepine-7-carboxamide (racemic)

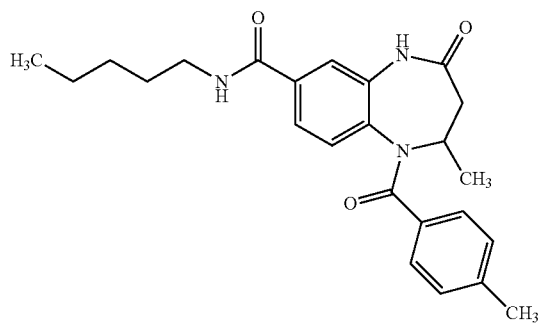 [SMILES: CCCCCNC(=O)c1ccc2c(c1)NC(=O)CC(C)N2C(=O)c1ccc(C)cc1]

Can be synthesized analogously to Example 1.

Example 48

1-(cyclopentylcarbonyl)-2-methyl-4-oxo-N-pentyl-2,3,4,5-tetrahydro-1H-1,5-benzodiazepine-7-carboxamide (racemic)

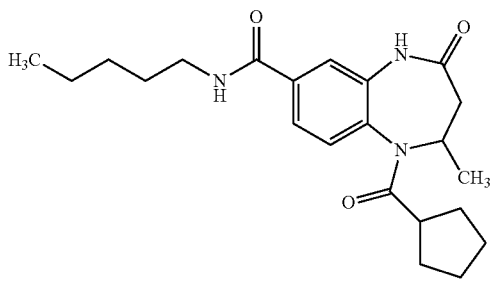 [SMILES: CCCCCNC(=O)c1ccc2c(c1)NC(=O)CC(C)N2C(=O)C1CCCC1]

Can be synthesized analogously to Example 1.

Example 49

2-methyl-4-oxo-N-propyl-1-(2-thienylcarbonyl)-2,3,4,5-tetrahydro-1H-1,5-benzodiazepine-7-carboxamide (racemic)

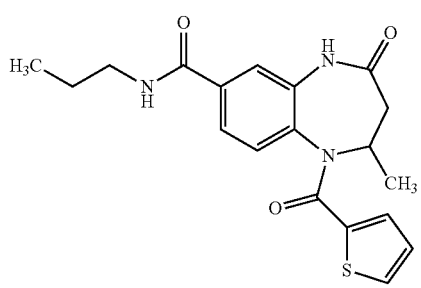 [SMILES: CCCNC(=O)c1ccc2c(c1)NC(=O)CC(C)N2C(=O)c1cccs1]

Can be synthesized analogously to Example 1.

Example 50

N-butyl-1-(cyclopropylcarbonyl)-2-methyl-4-oxo-2,3,4,5-tetrahydro-1H-1,5-benzodiazepine-7-carboxamide (racemic)

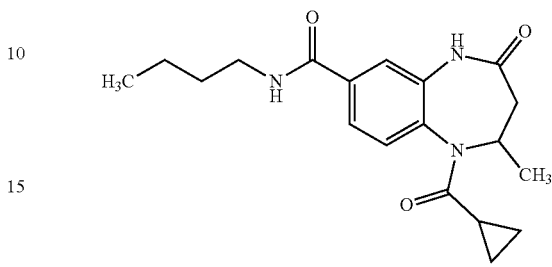

Can be synthesized analogously to Example 1.

Example 51

N-butyl-1-(3-cyclopentylpropanoyl)-2-methyl-4-oxo-2,3,4,5-tetrahydro-1H-1,5-benzodiazepine-7-carboxamide (racemic)

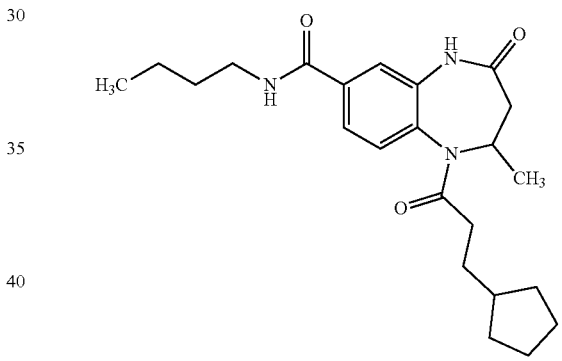

Can be synthesized analogously to Example 1.

Example 52

N-butyl-1-(3-fluorobenzoyl)-2-methyl-4-oxo-2,3,4,5-tetrahydro-1H-1,5-benzodiazepine-7-carboxamide (racemic)

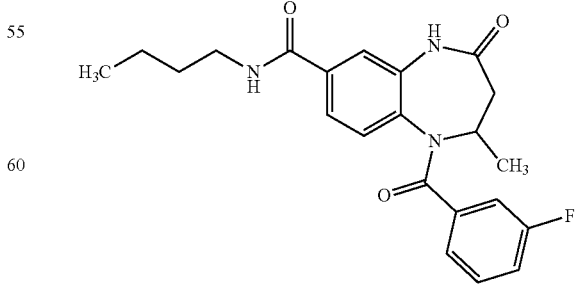

Can be synthesized analogously to Example 1.

Example 53

N-butyl-1-(2-fluorobenzoyl)-2-methyl-4-oxo-2,3,4,5-tetrahydro-1H-1,5-benzodiazepine-7-carboxamide (racemic)

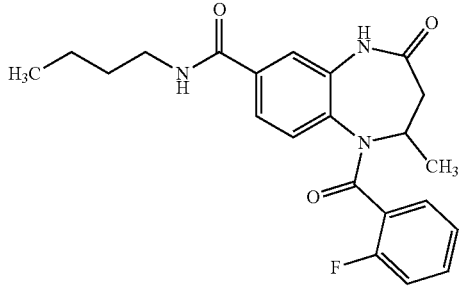 [SMILES: CCCCNC(=O)c1ccc2c(c1)NC(=O)CC(C)N2C(=O)c1ccccc1F]

Can be synthesized analogously to Example 1.

Example 54

(2S)-1-(3-azabicyclo[3.1.0]hexane-3-carbonyl)-N-(2-cyclopropylethyl)-N,2-dimethyl-4-oxo-2,3,4,5-tetrahydro-1H-1,5-benzodiazepine-7-carboxamide

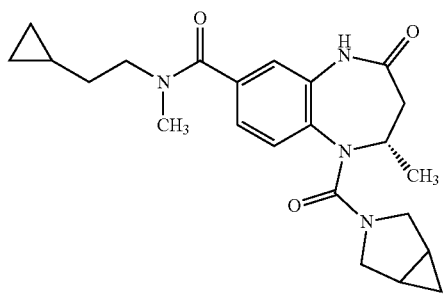 [SMILES: C[C@H]1CC(=O)Nc2cc(C(=O)N(C)CCC3CC3)ccc2N1C(=O)N1CC2CC2C1]

Can be synthesized analogously to Example 23.
MS (ESIpos): m/z=411.0 [M+H]+
$^1$H-NMR (400 MHz, CDCl3) δ [ppm]: δ 7.55-7.43 (m, 1H), 7.23 (dd, J=8.0, 1.6 Hz, 1H), 7.19-7.08 (m, 2H), 4.85-4.96 (m, 1H), 3.68-3.35 (m, 3H), 3.12-2.96 (m, 5H), 2.70-2.48 (m, 2H), 2.27 (t, J=12.0 Hz, 1H), 1.46 (d, J=6.4 Hz, 1H), 1.34-1.19 (m, 6H), 0.91-0.67 (m, 1H), 0.57-0.47 (m, 2H), 0.41 (s, 1H), 0.14 (s, 1H), 0.01-0.18 (m, 2H).

Example 55

(2R)-1-(3-azabicyclo[3.1.0]hexane-3-carbonyl)-N-(2-cyclopropylethyl)-2-methyl-4-oxo-2,3,4,5-tetrahydro-1H-1,5-benzodiazepine-7-carboxamide

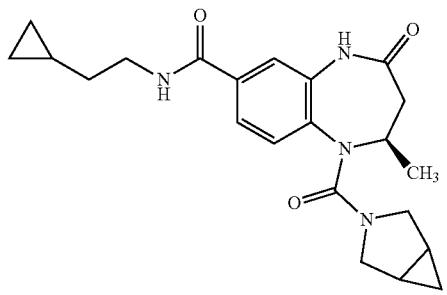 [SMILES: C[C@@H]1CC(=O)Nc2cc(C(=O)NCCC3CC3)ccc2N1C(=O)N1CC2CC2C1]

Can be synthesized analogously to Example 23.
MS (ESIpos): m/z=397.0 [M+H]$^+$
$^1$H-NMR (400 MHz, CDCl$_3$) δ [ppm]: 7.70-7.43 (m, 3H), 7.15 (d, J=8.0 Hz, 1H), 6.34 (s, 1H), 4.87-4.66 (m, 1H), 3.66-3.43 (m, 3H), 3.01 (d, J=10.4 Hz, 2H), 2.70-2.50 (m, 2H), 2.27 (dd, J=13.2, 10.8 Hz, 1H), 1.57 (q, J=7.2 Hz, 2H), 1.37-1.19 (m, 5H), 0.86-0.69 (m, 1H), 0.62-0.49 (m, 3H), 0.23-0.68 (m, 2H), −0.03 (q, J=4.0 Hz, 1H).

Example 56

(2R)-1-(3-azabicyclo[3.1.0]hexane-3-carbonyl)-N-(2-cyclopropylethyl)-N,2-dimethyl-4-oxo-2,3,4,5-tetrahydro-1H-1,5-benzodiazepine-7-carboxamide

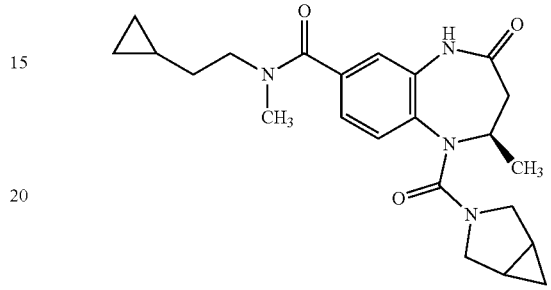

Can be synthesized analogously to Example 23.
LC-MS (Method A): R$_t$=0.96 min; MS (ESIpos): m/z=411 [M+H]$^+$
$^1$H-NMR (400 MHz, DMSO-d6) δ[ppm]: −0.153 (2.19), −0.144 (2.06), −0.055 (2.11), 0.154 (1.22), 0.381 (1.85), 0.494 (1.52), 0.524 (1.64), 0.536 (1.60), 0.544 (2.36), 0.555 (2.32), 0.563 (1.47), 0.574 (1.14), 0.776 (0.42), 1.203 (15.62), 1.218 (16.00), 1.299 (1.22), 1.327 (1.56), 1.358 (1.39), 1.368 (1.98), 1.377 (2.44), 1.387 (2.65), 1.396 (2.02), 1.405 (1.56), 1.415 (1.43), 1.434 (1.39), 1.448 (1.18), 1.541 (1.01), 1.556 (0.93), 2.166 (0.59), 2.197 (1.26), 2.226 (0.93), 2.388 (1.89), 2.393 (2.40), 2.397 (1.81), 2.402 (1.47), 2.423 (1.01), 2.439 (0.88), 2.584 (5.43), 2.588 (3.79), 2.730 (0.88), 2.735 (1.22), 2.740 (0.84), 2.909 (1.56), 2.935 (1.43), 2.984 (5.09), 3.011 (7.66), 3.330 (2.78), 3.347 (2.61), 3.571 (1.09), 3.610 (0.42), 4.511 (0.67), 4.526 (1.18), 4.540 (1.26), 4.554 (1.09), 4.568 (0.59), 7.091 (2.19), 7.123 (5.22), 7.142 (6.74), 7.209 (1.47), 7.229 (1.52), 9.876 (0.97), 9.922 (1.89).

EXPERIMENTAL SECTION—BIOLOGICAL ASSAYS

Thermal Shift Assay

Thermal melting experiments were performed with a ViiA™ Real-Time PCR machine (Thermo Fisher Scientific) in 384-well microliter plate with a final volume of 5 μL. Melting curves were obtained at a protein concentration of 1.5-2.0 μM and 5× SYPRO Orange (Invitrogen) using buffer containing 20 mM Tris pH7.0; 150 mM NaCl; 1.0 mM DTT. As protein untagged full length SMYD3 was used. Compounds were diluted in DMSO at a single concentration of 120 μM for primary screening, 100 μM for confirmation test or in a titration series (1, 2, 3, 10, 25, 50, 75, 100, 150 and 200 μM). As control 4% DMSO was used. Scans were measured from 25° C. to 80° C. at a scanning rate of 0.1° C./sec. All TSA data were analyzed by using Genedata Assay Analyzer.

SMYD3 Scintillation Proximity Assay (SPA)

SMYD3 inhibitory activities of the compounds described in the present invention were tested at Euroscreen S.A. (Gosselies, Belgium) using a scintillation proximity assay (SPA) which measures methylation by the enzyme of the synthetic, biotinylated peptide DYDNPIFEKFGKGGTY-PRRYHVSY-H-K(Btn)-amide (SEQ ID NO: 1)×TFA (e.g. from Biosyntan) derived from MAP3K2 and from here on referred to as "MAP3K2 Peptide". The SMYD3 full length enzyme was produced in-house by expression (with an N-terminal 6×His tag) in *E. coli* and purification by affinity chromatography on a Ni-NTA Sepharose column followed by a size exclusion chromatography step on a Superdex 200 16/60 column (GE Healthcare).

In a typical assay 11 different concentrations of each compound (0.1 nM, 0.33 nM, 1.1 nM, 3.8 nM, 13 nM, 44 nM, 0.15 μM, 0.51 μM, 1.7 μM, 5.9 μM and 20 μM) were tested in duplicate within the same microtiter plate. To this end, 100-fold concentrated compound solutions (in DMSO) were previously prepared by serial dilution (1:3.4) of 2 mM stocks in a clear low volume 384-well source microtiter plate (Greiner Bio-One), from which 100 nl of compounds were transferred into a white low volume test microtiter plate from the same supplier. Subsequently, 5 μl SMYD3 in aqueous assay buffer [50 mM Tris/HCl pH 8.4 (AppliChem), 10 mM dithiothreitol (DTT, Sigma), 0.01% (w/v) bovine serum albumine (BSA, Sigma), 0.001% (v/v) Pluronic F-127 (Sigma)] were added to the compounds in the test plate to a final enzyme concentration of 10 nM. The samples were then incubated for 15 min at 22° C. to allow pre-equilibration of the putative enzyme-inhibitor complexes before the start of the methylation reaction, which was initiated by the addition of 5 μl 2-fold concentrated solution (in assay buffer) of titriated S-Adenosyl-L-Methionine (3H-SAM, Perkin Elmer, final concentration: 125 nM) and MAP3K2 Peptide substrate (final concentration: 1 μM). The resulting mixture (5 μl final volume) was shortly centrifuged (2 min., 1500 rpm) and incubated at 22° C. during 120 min. Thereupon the reaction was stopped by adding 5 μl of Streptavidin coated PVT SPA beads (Perkin Elmer) at 2.53 μg/μl (38 μg/well) and "cold" SAM (AK Scientific, 250 μM final concentration) for non-specific binding reduction. Plates containing the stopped reaction were sealed with transparent adhesive foil (Perkin Elmer), centrifuged (2 min., 1500 rpm), and further incubated overnight at 4° C. in order to allow the SPA signals to develop. Subsequently, the amount of product was evaluated by measuring the energy transfer from the R-particles emitted by the 3H-labeled substrate to the scintillator co-polymerized in the bead's matrix, using a TopCount NXT scintillation counter (Packard) with the standard instrument settings for this purpose. The resulting scintillation counts were taken as indicator for the amount of methylated peptide per well. The data were normalised using two sets of control wells (typically 16 each) for high-(=enzyme reaction with DMSO instead of test compound=0%=Minimum inhibition) and low-(=all assay components without enzyme=100%=Maximum inhibition) SMYD3 activity. $IC_{50}$ values were calculated by fitting the normalized inhibition data to a 4-parameter logistic equation using the XLFit analysis software (IDBS).

Table 2 shows the results of the Thermal shift assay and the inhibition in the Scintillation Proximity assay

TABLE 2

| Example | SMYD3 Scintillation Proximity assay (M) | Thermal shift assay (° C.) |
|---|---|---|
| 1 | 1.66E−6 | 5.27 |
| 2 | 1.26E−6 | 5.21 |
| 3 | 1.63E−6 | 4.56 |
| 4 | 1.23E−6 | 4.38 |
| 5 | >2.00E−5 | 2.90 |
| 6 | 1.28E−5 | 2.83 |
| 8 | 4.90E−6 | 3.77 |
| 9 | >2.00E−5 | 1.82 |
| 10 | >2.00E−5 | 1.29 |
| 11 | 1.29E−5 | 3.50 |
| 13 | 4.62E−6 | 3.71 |
| 14 | >2.00E−5 | 1.15 |
| 15 | 2.00E−5 | 1.27 |
| 16 | 3.38E−6 | 3.51 |
| 17 | 3.46E−8 | 9.65 |
| 18 | 1.48E−7 | 8.48 |
| 19 | 3.72E−8 | 10.30 |
| 21 | 5.42E−8 | 9.35 |
| 22 | 2.23E−8 | 9.50 |
| 23 | 5.89E−8 | 9.88 |
| 24 | 7.06E−7 | 7.35 |
| 25 | 2.30E−6 | 6.12 |
| 26 | 1.26E−6 | 6.08 |
| 27 | 5.20E−7 | 8.77 |
| 28 | 1.30E−7 | 9.94 |
| 29 | 6.79E−7 | 5.51 |
| 30 | 7.87E−7 | 5.69 |
| 31 | 2.52E−6 | 2.79 |
| 33 | 4.60E−8 | 10.17 |
| 35 | 2.15E−8 | 10.91 |
| 37 | 2.15E−7 | 8.66 |
| 39 | 5.84E−7 | 7.25 |
| 41 | 2.65E−7 | 7.22 |
| 43 | 4.81E−7 | 7.49 |
| 45 | 3.90E−7 | 7.24 |
| 46 | 3.87E−5 | 2.02 |
| 47 | 2.21E−5 | 1.68 |
| 48 | 2.67E−5 | 1.60 |
| 49 |  | 1.43 |
| 50 | 3.50E−5 |  |
| 51 | 2.44E−5 | 1.83 |
| 52 | 1.83E−5 | 1.16 |
| 53 | 1.23E−5 | 2.53 |
| 54 | 2.53E−6 |  |
| 55 | 2.64E−6 |  |
| 56 | >3.00E−5 |  |

The invention claimed is:

1. A compound of formula (I):

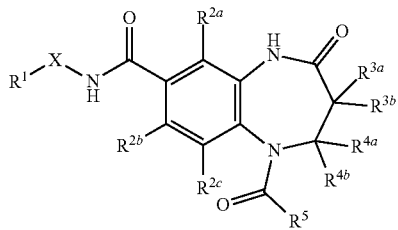

wherein:
X is $C_2$-$C_3$-alkylene;
$R^1$ is $C_3$-$C_5$-cycloalkyl;
$R^{2a}$ is hydrogen, hydroxy, halogen, cyano, $C_1$-$C_3$-alkyl, $C_1$-$C_3$-haloalkyl, $C_1$-$C_3$-alkoxy or $C_1$-$C_3$-haloalkoxy;
$R^{2b}$ is hydrogen, hydroxy, halogen, cyano, $C_1$-$C_3$-alkyl, $C_1$-$C_3$-haloalkyl, $C_1$-$C_3$-alkoxy or $C_1$-$C_3$-haloalkoxy;
$R^{2c}$ is hydrogen, hydroxy, halogen, cyano, $C_1$-$C_3$-alkyl, $C_1$-$C_3$-haloalkyl, $C_1$-$C_3$-alkoxy or $C_1$-$C_3$-haloalkoxy;
$R^{3a}$ is hydrogen or $C_1$-$C_3$-alkyl;
$R^{3b}$ is hydrogen or $C_1$-$C_3$-alkyl; or
$R^{3a}$ and $R^{3b}$ together with the carbon atom to which they are attached form a $C_3$-$C_6$-cycloalkyl group which is optionally substituted one, two or three times, independently of each other, with halogen;
$R^{4a}$ is s hydrogen or $C_1$-$C_3$-alkyl;
$R^{4b}$ is hydrogen or $C_1$-$C_3$-alkyl; or
$R^{4a}$ and $R^{4b}$ together with the carbon atom to which they are attached form a $C_3$-$C_6$-cycloalkyl group which is optionally substituted one, two or three times, independently of each other, with halogen;
$R^5$ is phenyl, wherein said phenyl is optionally substituted one, two or three times, independently of each other, with $R^{2b}$,
5- to 6-membered heteroaryl, wherein said 5- to 6-membered heteroaryl is optionally substituted one, two or three times, independently of each other, with $R^{2c}$,
$NR^6R^7$ or
5- to 8-membered nitrogen containing heterocyclic ring, to which nitrogen the ring is attached, said ring optionally containing one additional heteroatom selected from the group consisting of O, S, NH, and $NR^a$ wherein $R^a$ is a $C_1$-$C_4$-alkyl, $C_1$-$C_4$-haloalkyl or $C_2$-$C_4$-hydroxyalkyl group and the ring being optionally substituted one, two or three times, independently of each other, with halogen, $NR^8R^9$ or an oxo group;
$R^6$ and $R^7$ are independently hydrogen, $C_1$-$C_4$-alkyl, $C_1$-$C_4$-haloalkyl, $C_3$-$C_6$-cycloalkyl or 5- to 8-membered nitrogen containing heterocyclic ring, which ring is attached to a carbon atom, said ring optionally containing one additional heteroatom selected from the group consisting of O, S, NH, and $NR^a$ wherein $R^a$ is a $C_1$-$C_4$-alkyl, $C_1$-$C_4$-haloalkyl or $C_2$-$C_4$-hydroxyalkyl group and the ring being optionally substituted with halogen, $C_1$-$C_3$-alkyl, $C_1$-$C_4$-haloalkyl, $NR^8R^9$ or an oxo group; and
$R^8$ and $R^9$ are independently hydrogen, $C_1$-$C_4$-alkyl, or $C_1$-$C_4$-haloalkyl,
or a stereoisomer, a tautomer, an N-oxide, a hydrate, a solvate, or a salt thereof, or a mixture of same.

2. The compound according to claim 1, wherein:
X is $C_2$-$C_3$-alkylene;
$R^1$ is $C_3$-$C_4$-cycloalkyl;
$R^{2a}$ is hydrogen, hydroxy, halogen, cyano, $C_1$-$C_3$-alkyl, $C_1$-$C_3$-haloalkyl, $C_1$-$C_3$-alkoxy or $C_1$-$C_3$-haloalkoxy;
$R^{2b}$ is hydrogen, hydroxy, halogen, cyano, $C_1$-$C_3$-alkyl, $C_1$-$C_3$-haloalkyl, $C_1$-$C_3$-alkoxy or $C_1$-$C_3$-haloalkoxy;
$R^{2c}$ is hydrogen, hydroxy, halogen, cyano, $C_1$-$C_3$-alkyl, $C_1$-$C_3$-haloalkyl, $C_1$-$C_3$-alkoxy or $C_1$-$C_3$-haloalkoxy;
$R^{3a}$ is hydrogen or $C_1$-$C_2$-alkyl;
$R^{3b}$ is hydrogen or $C_1$-$C_2$-alkyl; or
$R^{3a}$ and $R^{3b}$ together with the carbon atom to which they are attached form a cyclopropyl group which is optionally substituted one, two or three times, independently of each other, with halogen;
$R^{4a}$ is hydrogen or $C_1$-$C_2$-alkyl;
$R^{4b}$ is hydrogen or $C_1$-$C_2$-alkyl; or
$R^{4a}$ and $R^{4b}$ together with the carbon atom to which they are attached form a cyclopropyl group which is optionally substituted one, two or three times, independently of each other, with halogen;
$R^5$ is phenyl, wherein said phenyl is optionally substituted one or two times, independently of each other, with $R^{2b}$,
5- to 6-membered heteroaryl, wherein said 5- to 6-membered heteroaryl is optionally substituted one or two times, independently of each other, with $R^{2c}$, $NR^6R^7$ or
5- to 7-membered nitrogen containing heterocyclic ring, to which nitrogen the ring is attached, said ring optionally containing one additional heteroatom selected from the group consisting of O, NH, and $NR^a$ wherein $R^a$ is a $C_1$-$C_4$-alkyl, $C_1$-$C_4$-haloalkyl or $C_2$-$C_4$-hydroxyalkyl group and the ring being optionally substituted one or two times, independently of each other, with halogen or $NR^8R^9$;
$R^6$ and $R^7$ are independently hydrogen, $C_1$-$C_4$-alkyl, $C_3$-$C_6$-cycloalkyl or 5- to 6-membered nitrogen containing heterocyclic ring, which ring is attached to a carbon atom, said ring optionally containing one additional heteroatom selected from the group consisting of O, NH, and $NR^a$ wherein $R^a$ is a $C_1$-$C_4$-alkyl, $C_1$-$C_4$-haloalkyl or $C_2$-$C_4$-hydroxyalkyl group and the ring being optionally substituted with halogen, $C_1$-$C_3$-alkyl, $C_1$-$C_4$-haloalkyl or $NR^8R^9$; and
$R^8$ and $R^9$ are independently hydrogen, $C_1$-$C_3$-alkyl, $C_1$-$C_3$-haloalkyl,
or a stereoisomer, a tautomer, an N-oxide, a hydrate, a solvate, or a salt thereof, or a mixture of same.

3. The compound according to claim 1, wherein:
X is ethylene;
R$^1$ is C$_3$-C$_4$-cycloalkyl;
R$^{2a}$ is hydrogen;
R$^{2b}$ is hydrogen;
R$^{2c}$ is hydrogen or methyl;
R$^{3a}$ is hydrogen or methyl;
R$^{3b}$ is hydrogen or methyl
R$^{4a}$ is hydrogen or methyl;
R$^{4b}$ is hydrogen or methyl;
R$^5$ is phenyl,
  3-methyl-1,2-oxazol-4-yl,-NR$^6$R$^7$ or
  a 5- to 7-membered nitrogen containing heterocyclic ring, to which nitrogen the ring is attached, said ring optionally containing one additional heteroatom selected from the group consisting of NH and NR$^a$ wherein R$^a$ is ethyl, 2,2,2-trifluoroethyl or 2-hydroxyethyl and the ring being optionally substituted once with NH$_2$ or NH—CH$_2$CF$_3$ and twice with fluoro; and
R$^6$ and R$^7$ are independently hydrogen, methyl or 6-membered nitrogen containing heterocyclic ring, which ring is attached to a carbon atom and optionally substituted with ethyl or 2,2,2-trifluoroethyl,
or a stereoisomer, a tautomer, an N-oxide, a hydrate, a solvate, or a salt thereof, or a mixture of same.

4. A compound selected from the group consisting of:
1-benzoyl-N-(2-cyclopropylethyl)-2-methyl-4-oxo-2,3,4,5-tetrahydro-1H-1,5-benzodiazepine-7-carboxamide;
1-benzoyl-N-(2-cyclopropylethyl)-2,3-dimethyl-4-oxo-2,3,4,5-tetrahydro-1H-1,5-benzodiazepine-7-carboxamide;
1-benzoyl-N-(2-cyclobutylethyl)-2-methyl-4-oxo-2,3,4,5-tetrahydro-1H-1,5-benzodiazepine-7-carboxamide;
1-benzoyl-N-(2-cyclobutylethyl)-2,3-dimethyl-4-oxo-2,3,4,5-tetrahydro-1H-1,5-benzodiazepine-7-carboxamide;
N-(2-cyclopropylethyl)-2-methyl-1-[(3-methyl-1,2-oxazol-4-yl)carbonyl]-4-oxo-2,3,4,5-tetrahydro-1H-1,5-benzodiazepine-7-carboxamide;
N-(2-cyclobutylethyl)-2-methyl-1-[(3-methyl-1,2-oxazol-4-yl)carbonyl]-4-oxo-2,3,4,5-tetrahydro-1H-1,5-benzodiazepine-7-carboxamide;
N-(2-cyclopropylethyl)-2,3-dimethyl-1-[(3-methyl-1,2-oxazol-4-yl)carbonyl]-4-oxo-2,3,4,5-tetrahydro-1H-1,5-benzodiazepine-7-carboxamide;
N-(2-cyclobutylethyl)-2,3-dimethyl-1-[(3-methyl-1,2-oxazol-4-yl)carbonyl]-4-oxo-2,3,4,5-tetrahydro-1H-1,5-benzodiazepine-7-carboxamide;
1-[(4-aminopiperidin-1-yl)carbonyl]-N-(2-cyclopropylethyl)-2-methyl-4-oxo-2,3,4,5-tetrahydro-1H-1,5-benzodiazepine-7-carboxamide;
(2R)-1-[(4-aminopiperidin-1-yl)carbonyl]-N-(2-cyclopropylethyl)-2-methyl-4-oxo-2,3,4,5-tetrahydro-1H-1,5-benzodiazepine-7-carboxamide;
1-[(4-aminopiperidin-1-yl)carbonyl]-N-(2-cyclopropylethyl)-2,3-dimethyl-4-oxo-2,3,4,5-tetrahydro-1H-1,5-benzodiazepine-7-carboxamide;
1-[(4-aminopiperidin-1-yl)carbonyl]-N-(2-cyclobutylethyl)-2,3-dimethyl-4-oxo-2,3,4,5-tetrahydro-1H-1,5-benzodiazepine-7-carboxamide;
(2S)-1-(3-azabicyclo[3.1.0]hex-3-ylcarbonyl)-N-(2-cyclopropylethyl)-2-methyl-4-oxo-2,3,4,5-tetrahydro-1H-1,5-benzodiazepine-7-carboxamide;
(2S)-N-(2-cyclopropylethyl)-1-[(3,3-difluoropyrrolidin-1-yl)carbonyl]-2-methyl-4-oxo-2,3,4,5-tetrahydro-1H-1,5-benzodiazepine-7-carboxamide;
(2S)-N-(2-cyclopropylethyl)-1-[(4,4-difluoropiperidin-1-yl)carbonyl]-2-methyl-4-oxo-2,3,4,5-tetrahydro-1H-1,5-benzodiazepine-7-carboxamide;
(2S)-N-(2-cyclopropylethyl)-1-{[4-(2-hydroxyethyl)piperazin-1-yl]carbonyl}-2-methyl-4-oxo-2,3,4,5-tetrahydro-1H-1,5-benzodiazepine-7-carboxamide;
(2S)-N-(2-cyclopropylethyl)-1-[(4-ethylpiperazin-1-yl)carbonyl]-2-methyl-4-oxo-2,3,4,5-tetrahydro-1H-1,5-benzodiazepine-7-carboxamide;
(2S)-N$^7$-(2-cyclopropylethyl)-N$^1$-(1-ethylpiperidin-4-yl)-N$^1$,2-dimethyl-4-oxo-2,3,4,5-tetrahydro-1H-1,5-benzodiazepine-1,7-dicarboxamide;
(2S)-N-(2-cyclopropylethyl)-2-methyl-4-oxo-1-({4-[(2,2,2-trifluoroethyl)amino]piperidin-1-yl}carbonyl)-2,3,4,5-tetrahydro-1H-1,5-benzodiazepine-7-carboxamide;
(2S)-N-(2-cyclopropylethyl)-2-methyl-4-oxo-1-{[4-(2,2,2-trifluoroethyl)piperazin-1-yl]carbonyl}-2,3,4,5-tetrahydro-1H-1,5-benzodiazepine-7-carboxamide;
(2S)-N$^7$-(2-cyclopropylethyl)-N$^1$,2-dimethyl-4-oxo-N$^1$-[1-(2,2,2-trifluoroethyl)piperidin-4-yl]-2,3,4,5-tetrahydro-1H-1,5-benzodiazepine-1,7-dicarboxamide;
tert-butyl 4-({(2S)-7-[(2-cyclopropylethyl)carbamoyl]-2-methyl-4-oxo-2,3,4,5-tetrahydro-1H-1,5-benzodiazepin-1-yl}carbonyl)-1,4-diazepane-1-carboxylate;
(2S)-N-(2-cyclopropylethyl)-1-(1,4-diazepan-1-ylcarbonyl)-2-methyl-4-oxo-2,3,4,5-tetrahydro-1H-1,5-benzodiazepine-7-carboxamide;
tert-butyl [1-({(2S)-7-[(2-cyclopropylethyl)carbamoyl]-2-methyl-4-oxo-2,3,4,5-tetrahydro-1H-1,5-benzodiazepin-1-yl}carbonyl)piperidin-4-yl]carbamate;
(2S)-1-[(4-aminopiperidin-1-yl)carbonyl]-N-(2-cyclopropylethyl)-2-methyl-4-oxo-2,3,4,5-tetrahydro-1H-1,5-benzodiazepine-7-carboxamide;
tert-butyl [(3S)-1-({(2S)-7-[(2-cyclopropylethyl)carbamoyl]-2-methyl-4-oxo-2,3,4,5-tetrahydro-1H-1,5-benzodiazepin-1-yl}carbonyl)pyrrolidin-3-yl]carbamate;
(2S)-1-{[(3S)-3-aminopyrrolidin-1-yl]carbonyl}-N-(2-cyclopropylethyl)-2-methyl-4-oxo-2,3,4,5-tetrahydro-1H-1,5-benzodiazepine-7-carboxamide hydrochloride;
tert-butyl [(3R)-1-({(2S)-7-[(2-cyclopropylethyl)carbamoyl]-2-methyl-4-oxo-2,3,4,5-tetrahydro-1H-1,5-benzodiazepin-1-yl}carbonyl)pyrrolidin-3-yl]carbamate;
(2S)-1-{[(3R)-3-aminopyrrolidin-1-yl]carbonyl}-N-(2-cyclopropylethyl)-2-methyl-4-oxo-2,3,4,5-tetrahydro-1H-1,5-benzodiazepine-7-carboxamide hydrochloride;
tert-butyl 4-({(2S)-7-[(2-cyclopropylethyl)carbamoyl]-2-methyl-4-oxo-2,3,4,5-tetrahydro-1H-1,5-benzodiazepin-1-yl}carbonyl)piperazine-1-carboxylate;
(2S)-N-(2-cyclopropylethyl)-2-methyl-4-oxo-1-(piperazin-1-ylcarbonyl)-2,3,4,5-tetrahydro-1H-1,5-benzodiazepine-7-carboxamide;
tert-butyl 4-[({(2S)-7-[(2-cyclopropylethyl)carbamoyl]-2-methyl-4-oxo-2,3,4,-tetrahydro-1H-1,5-benzodiazepin-1-yl}carbonyl)amino]piperidine-1-carboxylate;
(2S)-N$^7$-(2-cyclopropylethyl)-2-methyl-4-oxo-N$^1$-(piperidin-4-yl)-2,3,4,5-tetrahydro-1H-1,5-benzodiazepine-1,7-dicarboxamide;
tert-butyl 4-[({(2S)-7-[(2-cyclopropylethyl)carbamoyl]-2-methyl-4-oxo-2,3,4,5-tetrahydro-1H-1,5-benzodiazepin-1-yl}carbonyl)(methyl)amino]piperidine-1-carboxylate;
(2S)-N$^7$-(2-cyclopropylethyl)-N$^1$,2-dimethyl-4-oxo-N$^1$-(piperidin-4-yl)-2,3,4,5-tetrahydro-1H-1,5-benzodiazepine-1,7-dicarboxamide;
1-(2-fluorobenzoyl)-2-methyl-4-oxo-N-pentyl-2,3,4,5-tetrahydro-1H-1,5-benzodiazepine-7-carboxamide;

2-methyl-1-(4-methylbenzoyl)-4-oxo-N-pentyl-2,3,4,5-tetrahydro-1H-1,5-benzodiazepine-7-carboxamide;
1-(cyclopentylcarbonyl)-2-methyl-4-oxo-N-pentyl-2,3,4,5-tetrahydro-1H-1,5-benzodiazepine-7-carboxamide;
2-methyl-4-oxo-N-propyl-1-(2-thienylcarbonyl)-2,3,4,5-tetrahydro-1H-1,5-benzodiazepine-7-carboxamide;
N-butyl-1-(cyclopropylcarbonyl)-2-methyl-4-oxo-2,3,4,5-tetrahydro-1H-1,5-benzodiazepine-7-carboxamide;
N-butyl-1-(3-cyclopentylpropanoyl)-2-methyl-4-oxo-2,3,4,5-tetrahydro-1H-1,5-benzodiazepine-7-carboxamide;
N-butyl-1-(3-fluorobenzoyl)-2-methyl-4-oxo-2,3,4,5-tetrahydro-1H-1,5-benzodiazepine-7-carboxamide;
N-butyl-1-(2-fluorobenzoyl)-2-methyl-4-oxo-2,3,4,5-tetrahydro-1H-1,5-benzodiazepine-7-carboxamide;
(2S)-1-(3-azabicyclo[3.1.0]hexane-3-carbonyl)-N-(2-cyclopropylethyl)-N,2-dimethyl-4-oxo-2,3,4,5-tetrahydro-1H-1,5-benzodiazepine-7-carboxamide;
(2R)-1-(3-azabicyclo[3.1.0]hexane-3-carbonyl)-N-(2-cyclopropylethyl)-2-methyl-4-oxo-2,3,4,5-tetrahydro-1H-1,5-benzodiazepine-7-carboxamide; and
(2R)-1-(3-azabicyclo[3.1.0]hexane-3-carbonyl)-N-(2-cyclopropylethyl)-N,2-dimethyl-4-oxo-2,3,4,5-tetrahydro-1H-1,5-benzodiazepine-7-carboxamide,
or a stereoisomer, a tautomer, an N-oxide, a hydrate, a solvate, or a salt thereof, or a mixture of same.

5. A method of preparing a compound of formula (I) according to claim 1, said method comprising reacting an intermediate compound of formula (IV):

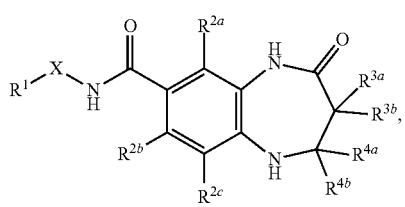

wherein $R^1$, $R^{2a}$, $R^{2b}$, $R^{2c}$, $R^{3a}$, $R^{3b}$, $R^{4a}$, $R^{4b}$ and X are as defined for the compound of formula (I) according to claim 1,
with a compound of formula (V):

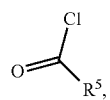

wherein $R^5$ is as defined for the compound of formula (I) according to claim 1,
thereby giving a compound of formula (I):

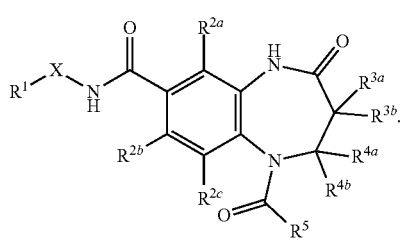

6. A pharmaceutical composition comprising a compound of formula (I) according to claim 1 and one or more pharmaceutically acceptable excipients.

7. A pharmaceutical combination comprising:
one or more first active ingredients, wherein the one or more first active ingredients comprises a compound of formula (I) according to claim 1, and
one or more further active ingredients.

8. The pharmaceutical combination according to claim 7, wherein the one or more further active ingredients comprises a cancer agent.

9. The compound of claim 4, wherein the compound is selected from the group consisting of:
1-benzoyl-N-(2-cyclopropylethyl)-2-methyl-4-oxo-2,3,4,5-tetrahydro-1H-1,5-benzodiazepine-7-carboxamide;
1-benzoyl-N-(2-cyclopropylethyl)-2,3-dimethyl-4-oxo-2,3,4,5-tetrahydro-1H-1,5-benzodiazepine-7-carboxamide;
1-benzoyl-N-(2-cyclobutylethyl)-2-methyl-4-oxo-2,3,4,5-tetrahydro-1H-1,5-benzodiazepine-7-carboxamide;
1-benzoyl-N-(2-cyclobutylethyl)-2,3-dimethyl-4-oxo-2,3,4,5-tetrahydro-1H-1,5-benzodiazepine-7-carboxamide;
N-(2-cyclopropylethyl)-2-methyl-1-[(3-methyl-1,2-oxazol-4-yl)carbonyl]-4-oxo-2,3,4,5-tetrahydro-1H-1,5-benzodiazepine-7-carboxamide;
N-(2-cyclobutylethyl)-2-methyl-1-[(3-methyl-1,2-oxazol-4-yl)carbonyl]-4-oxo-2,3,4,5-tetrahydro-1H-1,5-benzodiazepine-7-carboxamide;
N-(2-cyclopropylethyl)-2,3-dimethyl-1-[(3-methyl-1,2-oxazol-4-yl)carbonyl]-4-oxo-2,3,4,5-tetrahydro-1H-1,5-benzodiazepine-7-carboxamide;
N-(2-cyclobutylethyl)-2,3-dimethyl-1-[(3-methyl-1,2-oxazol-4-yl)carbonyl]-4-oxo-2,3,4,5-tetrahydro-1H-1,5-benzodiazepine-7-carboxamide;
1-[(4-aminopiperidin-1-yl)carbonyl]-N-(2-cyclopropylethyl)-2-methyl-4-oxo-2,3,4,5-tetrahydro-1H-1,5-benzodiazepine-7-carboxamide;
(2R)-1-[(4-aminopiperidin-1-yl)carbonyl]-N-(2-cyclopropylethyl)-2-methyl-4-oxo-2,3,4,5-tetrahydro-1H-1,5-benzodiazepine-7-carboxamide;
1-[(4-aminopiperidin-1-yl)carbonyl]-N-(2-cyclopropylethyl)-2,3-dimethyl-4-oxo-2,3,4,5-tetrahydro-1H-1,5-benzodiazepine-7-carboxamide;
1-[(4-aminopiperidin-1-yl)carbonyl]-N-(2-cyclobutylethyl)-2,3-dimethyl-4-oxo-2,3,4,5-tetrahydro-1H-1,5-benzodiazepine-7-carboxamide;
(2S)-1-(3-azabicyclo[3.1.0]hex-3-ylcarbonyl)-N-(2-cyclopropylethyl)-2-methyl-4-oxo-2,3,4,5-tetrahydro-1H-1,5-benzodiazepine-7-carboxamide;
(2S)-N-(2-cyclopropylethyl)-1-[(3,3-difluoropyrrolidin-1-yl)carbonyl]-2-methyl-4-oxo-2,3,4,5-tetrahydro-1H-1,5-benzodiazepine-7-carboxamide;
(2S)-N-(2-cyclopropylethyl)-1[(4,4-difluoropiperidin-1-yl)carbonyl]-2-methyl-4-oxo-2,3,4,5-tetrahydro-1H-1,5-benzodiazepine-7-carboxamide;
(2S)-N-(2-cyclopropylethyl)-1-{[4-(2-hydroxyethyl)piperazin-1-yl]carbonyl}-2-methyl-4-oxo-2,3,4,5-tetrahydro-1H-1,5-benzodiazepine-7-carboxamide;
(2S)-N-(2-cyclopropylethyl)-1-[(4-ethylpiperazin-1-yl)carbonyl]-2-methyl-4-oxo-2,3,4,5-tetrahydro-1H-1,5-benzodiazepine-7-carboxamide;
(2S)-$N^7$-(2-cyclopropylethyl)-$N^1$-(1-ethylpiperidin-4-yl)-$N^1$,2-dimethyl-4-oxo-2,3,4,5-tetrahydro-1H-1,5-benzodiazepine-1,7-dicarboxamide;

(2S)-N-(2-cyclopropylethyl)-2-methyl-4-oxo-1-({4-[(2,2,2-trifluoroethyl)amino]piperidin-1-yl}carbonyl)-2,3,4,5-tetrahydro-1H-1,5-benzodiazepine-7-carboxamide;

(2S)-N-(2-cyclopropylethyl)-2-methyl-4-oxo-1-{[4-(2,2,2-trifluoroethyl)piperazin-1-yl]carbonyl}-2,3,4,5-tetrahydro-1H-1,5-benzodiazepine-7-carboxamide;

(2S)-N$^7$-(2-cyclopropylethyl)-N$^1$,2-dimethyl-4-oxo-N$^1$-[1-(2,2,2-trifluoroethyl)piperidin-4-yl]-2,3,4,5-tetrahydro-1H-1,5-benzodiazepine-1,7-dicarboxamide;

tert-butyl 4-({(2S)-7-[(2-cyclopropylethyl)carbamoyl]-2-methyl-4-oxo-2,3,4,5-tetrahydro-1H-1,5-benzodiazepin-1-yl}carbonyl)-1,4-diazepane-1-carboxylate;

(2S)-N-(2-cyclopropylethyl)-1-(1,4-diazepan-1-ylcarbonyl)-2-methyl-4-oxo-2,3,4,5-tetrahydro-1H-1,5-benzodiazepine-7-carboxamide;

tert-butyl [1-({(2S)-7-[(2-cyclopropylethyl)carbamoyl]-2-methyl-4-oxo-2,3,4,5-tetrahydro-1H-1,5-benzodiazepin-1-yl}carbonyl)piperidin-4-yl]carbamate;

(2S)- 1-[(4-aminopiperidin-1-yl)carbonyl]-N-(2-cyclopropylethyl)-2-methyl-4-oxo-2,3,4,5-tetrahydro-1H-1,5-benzodiazepine-7-carboxamide;

tert-butyl [(3S)-1-({(2S)-7-[(2-cyclopropylethyl)carbamoyl]-2-methyl-4-oxo-2,3,4,5-tetrahydro-1H-1,5-benzodiazepin-1-yl}carbonyl)pyrrolidin-3-yl]carbamate;

(2S)-1-{[(3S)-3 -aminopyrrolidin-1-yl]carbonyl}-N-(2-cyclopropylethyl)-2-methyl-4-oxo-2,3,4,5-tetrahydro-1H-1,5-benzodiazepine-7-carboxamide hydrochloride;

tert-butyl [(3R)-1-({(2S)-7-[(2-cyclopropylethyl)carbamoyl]-2-methyl-4-oxo-2,3,4,5-tetrahydro-1H-1,5-benzodiazepin-1-yl}carbonyl)pyrrolidin-3-yl]carbamate;

(2S)-1-{[(3R)-3 -aminopyrrolidin-1-yl]carbonyl}-N-(2-cyclopropylethyl)-2-methyl-4-oxo-2,3,4,5-tetrahydro-1H-1,5-benzodiazepine-7-carboxamide hydrochloride;

tert-butyl 4-({(2S)-7-[(2-cyclopropylethyl)carbamoyl]-2-methyl-4-oxo-2,3,4,5-tetrahydro-1H-1,5-benzodiazepin-1-yl}carbonyl)piperazine-1-carboxylate;

(2S)-N-(2-cyclopropylethyl)-2-methyl-4-oxo-1-(piperazin-1-ylcarbonyl)-2,3,4,5-tetrahydro-1H-1,5-benzodiazepine-7-carboxamide;

tert-butyl 4-[({(2S)-7-[(2-cyclopropylethyl)carbamoyl]-2-methyl-4-oxo-2,3,4,5-tetrahydro-1H-1,5-benzodiazepin-1-yl}carbonyl)amino]piperidine-1-carboxylate;

(2S)-N$^7$-(2-cyclopropylethyl)-2-methyl-4-oxo-N$^1$-(piperidin-4-yl)-2,3,4,5-tetrahydro-1H-1,5-benzodiazepine-1,7-dicarboxamide;

tert-butyl 4-[({(2S)-7-[(2-cyclopropylethyl)carbamoyl]-2-methyl-4-oxo-2,3,4,5-tetrahydro-1H-1,5-benzodiazepin-1-yl}carbonyl)(methyl)amino]piperidine-1-carboxylate;

(2S)-N$^7$-(2-cyclopropylethyl)-N$^1$,2-dimethyl-4-oxo-N$^1$-(piperidin-4-yl)-2,3,4,5-tetrahydro-1H-1,5-benzodiazepine-1,7-dicarboxamide;

1-(2-fluorobenzoyl)-2-methyl-4-oxo-N-pentyl-2,3,4,5-tetrahydro-1H-1,5-benzodiazepine-7-carboxamide;

2-methyl-1-(4-methylbenzoyl)-4-oxo-N-pentyl-2,3,4,5-tetrahydro-1H-1,5-benzodiazepine-7-carboxamide;

1-(cyclopentylcarbonyl)-2-methyl-4-oxo-N-pentyl-2,3,4,5-tetrahydro-1H-1,5-benzodiazepine-7-carboxamide;

2-methyl-4-oxo-N-propyl-1-(2-thienylcarbonyl)-2,3,4,5-tetrahydro-1H-1,5-benzodiazepine-7-carboxamide;

N-butyl-1-(cyclopropylcarbonyl)-2-methyl-4-oxo-2,3,4,5-tetrahydro-1H-1,5-benzodiazepine-7-carboxamide;

N-butyl-1-(3-cyclopentylpropanoyl)-2-methyl-4-oxo-2,3,4,5-tetrahydro-1H-1,5-benzodiazepine-7-carboxamide;

N-butyl-1-(3-fluorobenzoyl)-2-methyl-4-oxo-2,3,4,5-tetrahydro-1H-1,5-benzodiazepine-7-carboxamide;

N-butyl-1-(2-fluorobenzoyl)-2-methyl-4-oxo-2,3,4,5-tetrahydro-1H-1,5-benzodiazepine-7-carboxamide;

(2S)-1-(3-azabicyclo[3.1.0]hexane-3-carbonyl)-N-(2-cyclopropylethyl)-N,2-dimethyl-4-oxo-2,3,4,5-tetrahydro-1H-1,5-benzodiazepine-7-carboxamide;

(2R)-1-(3-azabicyclo[3.1.0]hexane-3-carbonyl)-N-(2-cyclopropylethyl)-2-methyl-4-oxo-2,3,4,5-tetrahydro-1H-1,5-benzodiazepine-7-carboxamide; and (2R)-1-(3-azabicyclo[3.1.0]hexane-3-carbonyl)-N-(2-cyclopropylethyl)-N,2-dimethyl-4-oxo-2,3,4,5-tetrahydro-1H-1,5-benzodiazepine-7-carboxamide, or a stereoisomer, a tautomer, or a salt thereof, or a mixture of same.

10. A pharmaceutical composition, comprising a compound according to claim 4 and one or more pharmaceutically acceptable excipients.

11. A pharmaceutical combination comprising:
one or more first active ingredients, wherein the one or more first active ingredients comprises a compound according to claim 4, and
one or more further active ingredients.

12. The pharmaceutical combination according to claim 11, wherein the one or more further active ingredients comprises a cancer agent.

13. The method of claim 5, wherein the compound of formula (I) is selected from the group consisting of:

1-benzoyl-N-(2-cyclopropylethyl)-2-methyl-4-oxo-2,3,4,5-tetrahydro-1H-1,5-benzodiazepine-7-carboxamide;

1-benzoyl-N-(2-cyclopropylethyl)-2,3-dimethyl-4-oxo-2,3,4,5-tetrahydro-1H-1,5-benzodiazepine-7-carboxamide;

1-benzoyl-N-(2-cyclobutylethyl)-2-methyl-4-oxo-2,3,4,5-tetrahydro-1H-1,5-benzodiazepine-7-carboxamide;

1-benzoyl-N-(2-cyclobutylethyl)-2,3-dimethyl-4-oxo-2,3,4,5-tetrahydro-1H-1,5-benzodiazepine-7-carboxamide;

N-(2-cyclopropylethyl)-2-methyl-1-[(3-methyl-1,2-oxazol-4-yl)carbonyl]-4-oxo-2,3,4,5-tetrahydro-1H-1,5-benzodiazepine-7-carboxamide;

N-(2-cyclobutylethyl)-2-methyl-1-[(3-methyl-1,2-oxazol-4-yl)carbonyl]-4-oxo-2,3,4,5-tetrahydro-1H-1,5-benzodiazepine-7-carboxamide;

N-(2-cyclopropylethyl)-2,3-dimethyl-1-[(3-methyl-1,2-oxazol-4-yl)carbonyl]-4-oxo-2,3,4,5-tetrahydro-1H-1,5-benzodiazepine-7-carboxamide;

N-(2-cyclobutylethyl)-2,3-dimethyl-1-[(3-methyl-1,2-oxazol-4-yl)carbonyl]-4-oxo-2,3,4,5-tetrahydro-1H-1,5-benzodiazepine-7-carboxamide;

1-[(4-aminopiperidin-1-yl)carbonyl]-N-(2-cyclopropylethyl)-2-methyl-4-oxo-2,3,4,5-tetrahydro-1H-1,5-benzodiazepine-7-carboxamide;

(2R)-1-[(4-aminopiperidin-1-yl)carbonyl]-N-(2-cyclopropylethyl)-2-methyl-4-oxo-2,3,4,5-tetrahydro-1H-1,5-benzodiazepine-7-carboxamide;

1-[(4-aminopiperidin-1-yl)carbonyl]-N-(2-cyclopropylethyl)-2,3-dimethyl-4-oxo-2,3,4,5-tetrahydro-1H-1,5-benzodiazepine-7-carboxamide;

1-[(4-aminopiperidin-1-yl)carbonyl]-N-(2-cyclobutylethyl)-2,3-dimethyl-4-oxo-2,3,4,5-tetrahydro-1H-1,5-benzodiazepine-7-carboxamide;

(2S)-1-(3-azabicyclo[3.1.0]hex-3-ylcarbonyl)-N-(2-cyclopropylethyl)-2-methyl-4-oxo-2,3,4,5-tetrahydro-1H-1,5-benzodiazepine-7-carboxamide;

(2S)-N-(2-cyclopropylethyl)-1-[(3,3-difluoropyrrolidin-1-yl)carbonyl]-2-methyl-4-oxo-2,3,4,5-tetrahydro-1H-1,5-benzodiazepine-7-carboxamide;

(2S)-N-(2-cyclopropylethyl)-1-[(4,4-difluoropiperidin-1-yl)carbonyl]-2-methyl-4-oxo-2,3,4,5-tetrahydro-1H-1,5-benzodiazepine-7-carboxamide;

(2S)-N-(2-cyclopropylethyl)-1-{[4-(2-hydroxyethyl)piperazin-1-yl]carbonyl}-2-methyl-4-oxo-2,3,4,5-tetrahydro-1H-1,5-benzodiazepine-7-carboxamide;

(2S)-N-(2-cyclopropylethyl)-1-[(4-ethylpiperazin-1-yl)carbonyl]-2-methyl-4-oxo-2,3,4,5-tetrahydro-1H-1,5-benzodiazepine-7-carboxamide;

(2S)-$N^7$-(2-cyclopropylethyl)-$N^1$-(1-ethylpiperidin-4-yl)-$N^1$,2-dimethyl-4-oxo-2,3,4,5-tetrahydro-1H-1,5-benzodiazepine-1,7-dicarboxamide;

(2S)-N-(2-cyclopropylethyl)-2-methyl-4-oxo-1-({4-[(2,2,2-trifluoroethyl)amino]piperidin-1-yl}carbonyl)-2,3,4,5-tetrahydro-1H-1,5-benzodiazepine-7-carboxamide;

(2S)-N-(2-cyclopropylethyl)-2-methyl-4-oxo-1-{[4-(2,2,2-trifluoroethyl)piperazin-1-yl]carbonyl}-2,3,4,5-tetrahydro-1H-1,5-benzodiazepine-7-carboxamide;

(2S)-$N^7$-(2-cyclopropylethyl)-$N^1$,2-dimethyl-4-oxo-$N^1$-[1-(2,2,2-trifluoroethyl)piperidin-4-yl]-2,3,4,5-tetrahydro-1H-1,5-benzodiazepine-1,7-dicarboxamide;

(2S)-N-(2-cyclopropylethyl)-1-(1,4-diazepan-1-ylcarbonyl)-2-methyl-4-oxo-2,3,4,5-tetrahydro-1H-1,5-benzodiazepine-7-carboxamide;

(2S)-1-[(4-aminopiperidin-1-yl)carbonyl]-N-(2-cyclopropylethyl)-2-methyl-4-oxo-2,3,4,5-tetrahydro-1H-1,5-benzodiazepine-7-carboxamide;

(2S)-1-{[(3S)-3-aminopyrrolidin-1-yl]carbonyl}-N-(2-cyclopropylethyl)-2-methyl-4-oxo-2,3,4,5-tetrahydro-1H-1,5-benzodiazepine-7-carboxamide hydrochloride;

(2S)-1-{[(3R)-3-aminopyrrolidin-1-yl]carbonyl}-N-(2-cyclopropylethyl)-2-methyl-4-oxo-2,3,4,5-tetrahydro-1H-1,5-benzodiazepine-7-carboxamide hydrochloride;

(2S)-N-(2-cyclopropylethyl)-2-methyl-4-oxo-1-(piperazin-1-ylcarbonyl)-2,3,4,5-tetrahydro-1H-1,5-benzodiazepine-7-carboxamide;

(2R)-1-(3-azabicyclo[3.1.0]hexane-3-carbonyl)-N-(2-cyclopropylethyl)-2-methyl-4-oxo-2,3,4,5-tetrahydro-1H-1,5-benzodiazepine-7-carboxamide.

\* \* \* \* \*